US006232106B1

(12) United States Patent
Jensen et al.

(10) Patent No.: US 6,232,106 B1
(45) Date of Patent: May 15, 2001

(54) DNA SEQUENCE ENCODING ENZYMES OF CLAVULANIC ACID BIOSYNTHESIS

(75) Inventors: Susan E. Jensen, Edmonton; Kwamena A. Aidoo, Timberlea; Ashish S. Paradkar, Edmonton, all of (CA)

(73) Assignee: The Governors of the University of Alberta, Edmonton (CA)

( * ) Notice: Subject to any disclaimer, the term of this patent is extended or adjusted under 35 U.S.C. 154(b) by 0 days.

(21) Appl. No.: 09/385,028

(22) Filed: Aug. 30, 1999

Related U.S. Application Data

(60) Division of application No. 08/790,462, filed on Jan. 29, 1997, now abandoned, which is a continuation-in-part of application No. 08/567,801, filed on Dec. 6, 1995, now abandoned, which is a continuation of application No. 08/134,018, filed on Oct. 8, 1993, now abandoned.

(51) Int. Cl.$^7$ .............................. C12N 9/00; C07K 14/36
(52) U.S. Cl. ........................................... 435/183; 530/350
(58) Field of Search .............................. 435/183; 530/350

(56) References Cited

FOREIGN PATENT DOCUMENTS 0 349 121 A2   1/1990 (EP).

OTHER PUBLICATIONS

The Sixth Conference on the Genetics and Molecular Biology of Industrial Microorganisms (GMBIM) Oct. 20–24, 1996, Bloomington, In. p. 26, P48 Identification of a Pathway–specific Transcriptional Activator Involved in Clavulanic Acid Biosynthesis in *Streptomyces clavuligerus*, A.S. Paradkar, K.A. Aidoo, S.E. Jensen.
Journal of Bacteriology, vol. 177, Mar., 1995, p. 1307–1314—Functional Analysis of the Gene Encoding the Clavaminate Synthase 2 Isoenzyme Involved in Clavulanic Acid Biosynthesis in *Streptomyces clavuligeru*, Ashish S. Paradkar and Susan E. Jensen.
*Gene*, 147 (1994) 41–46, Cloning, Sequencing and disruption of a gene from *Streptomyces clavuligerus* involved in clavulanic acid biosynthesis—Kwamena A. Aidoo, Annie Wong, Dylan C. Alexander, Randy A.R. Rittammer and Susan E. Jensen.
Industrial Microorganisms: Basic and Applied Molecular Genetics, 1993 American Society for Microbiology, Washington, Chapter 22, pp. 169–176 Extending the β–Lactam Biosynthetic Gene Cluster in *Streptomyces clavuligerus*, Susan E. Jensen, Dylan C. Alexander, Ashish S. Paradkar, and Kwamena A. Aidoo.
Antimicrobial Agents and Chemotherapy, Nov. 1982, vol. 22, p. 753–762, Assay of Amoxicillin and Calvulanic Acid, the Components of Augmentin, in Biological Fluids with High–Performance Liquid Chromatography, Mark Foulstone and Christopher Reading.

Biochemistry 1992, 31, 12648–12657, Two Isozymes of Clavaminate Synthase Central to Clavulanic Acid Formation: Cloning and Sequencing of Both Genes from *Streptomyces clavuligerus*, E. Neil Marsh, Margaret Dah–Tsyr Chang, and Craig A. Townsend.
Journal of Bacteriology, Sep. 1990, vol. 172, p. 4909–4918—Isolation and Characterization of a β–Lactamase–Inhibitory Protein from *Streptomyces clavuligerus* and Cloning and Analysis of the Corresponding Gene, James L. Doran, Brenda K. Leskiw, Sven Aippersbach and Susan E. Jensen.
FEMS Microbiology Letters 110 (1993) 239–242, The biosynthetic genes for clavulanic acid and cephamycin production occur as a "super–cluster" in three Streptomyces, Judith M. Ward and John E. Hodgson.
Journal of Bacteriology, Dec. 1990, vol. 172, p. 7269–7271, Purification and Partial Characterization of δ–(L–α–Aminoadipyl)–L–Cysteinyl–D–Valine Synthetase from *Streptomyces clavuligerus*, Susan E. Jensen, A. Wong, M.J. Rollins and D.W.S. Westlake.
Eur. J. Biochem. 203, 687–694 (1992) Enzymatic characterisation of the multifunctional enzyme δ–(L–α–aminoadipyl)–L–cysteinyl–D–valine synthetase from *Streptomyces clavuligerus*, Torsten Schwecke, Yair Aharonowitz, Harriet Palissa, Hans von Dohren, Horst Kleinkauf and Henk van Liempt.
Biotechnology Letters, vol. 12 No. 9, 649–654 (1990), Purification of ACV Synthetase from *Streptomyces Clavuligerus*, Jinyou Zhang and Arnold L. Demain.
ATCC Catalogue of Bacterial and Phages, American Type Culture Collection, Rockville, Maryland, 1992, pp. 321, 675.
Hunkapiller et al. Meth. Enzymol., 91:227–236 (1983).
Ohtsuka et al, J. Biol. Chem., 260:2605–2608 (1985).
Lathe, J. Mol. Biol., 183:1–12 (1985).
Elson et al, J. Chem. Soc., Chem. Commun., 1993, pp. 1212–1214.
Jensen et al, "Expression of the *Streptomyces clavuligerus* Isopennicillin N Synthase Gene in *Escherichia coli* and *Streptomyces lividans*", Genetics and Molecular Biology of Industrial Microorganisms, 1989, pp. 239–245.
Valentine et al, J. Chem. Soc., Chem. Commun., 1993, pp. 1210–1211.
Jensen et al, Appl. Microbiol. Biotechnol. (1984) 20:155–160.
Madduri et al, Journal of Bacteriology, vol. 173, Feb. 1991, pp. 985–988.
Madduri et al, Journal of Bacteriology, vol. 171, Jan. 1989, pp. 299–302.
Jensen, Journal of Bacteriology, Dec. 1990, pp. 7269–7271.
Elson et al, J. Chem. Soc., Chem. Commun. 1993, pp. 1211–1212.

*Primary Examiner*—Elizabeth Slobodyansky
(74) *Attorney, Agent, or Firm*—Jacobson, Price, Holman & Stern, PLLC

(57) ABSTRACT

DNA sequences are provided which encode the enzymes required for clavulanic acid synthesis. A process is provided for producing clavulanic acid in a transformant of a non-clavulanate-producing host.

7 Claims, 35 Drawing Sheets

| N-terminal amino acid sequence of CLA | Met<br>Tyr | Glu<br>Ala | Arg<br>Gln | Ile<br>Ile | Asp<br>Pro | Ser<br>Thr | His<br>Phe | Val<br>Met | Ser<br>Arg | Pro<br>(Leu) | Arg<br>Pro | His | Asp<br>(Asp) |
|---|---|---|---|---|---|---|---|---|---|---|---|---|---|
| Potential codons (DNA) | TAT<br>C | GCT<br>C<br>A<br>G | CAA<br>G | ATT<br>C<br>A | CCT<br>C<br>A<br>G | ACT<br>C<br>A<br>G | TTT<br>C | ATG | | | | | |
| Probe made = 24-mer oligonucleotide with 8-fold degeneracy | TAC | GCC<br>G | CAG | ATC | CCC<br>G | ACC<br>G | TTC | ATG | | | | | |
| Actual DNA sequence | TAC | GCA | CAG | ATC | CCC | ACC | TTC | ATG | | | | | |

```
       |  10       |  20       |  30       |  40       |  50       |  60
   1 gcggaaccgg ccgccectga gcggggcggc cgggaaggaa acgggccggt cgtccectcg  60
                                                        <--End of ORF 1
  61 ggaggggggcg gccggcccgt ccggtgcgcg cggtgggtgc ggcgcgggTC AGCCGGCCGC 120
 121 GAGGTTGCTG AGGAACTTCG CGGCGACGGG GCCCGCGTCG GCGCCGCCCG ACCCGCCGTC 180
 181 CTCCAGCAGG ACCGACCAGG CGATGTTCCG GTCGCCCTGG TAGCCGATCA TCCAGGCGTG 240
 241 CGTCTTCGGC GGCTTCTCGG TGCCGAACTC GGCGGTACCG GTCTTGGCGT GCGGCTGTCC 300
 301 GCCGAGGCCC CGCAGGGCGT CGCCGGCGCC GTCGGTGACG GTCGAACGCA TCATGGAACG 360
 361 CAGCGAGTCG ACGATGCCCG GGGCCATCCG GGGGGCCTGG TGCGGCTTCT TGACCGCGTC 420
 421 GGGCACCAGC ACGGGCTGCT TGAACTCGCC CTGCTTGACG GTGGCGGCGA TGGAGGCCAT 480
 481 CACCAGGGGC GACGCCTCGA CCCTGGCCTG TCCGATGGTG GACGCGGCCT TGTCGTTCTC 540
 541 GCTGTTGGAG ACGGGGACGC TGCCGTCGAA GGTGGAGGCG CCGACGTCCC AGGTGCCGCC 600
 601 GATGCCGAAG GCTTCGGCGG CCTGCTTCAG GCTGGACTCG GAGAGCTTGC TGCGGGAGTT 660
 661 GACGAAGAAC GTGTTGCAGG AGTGGGCGAA GCTGTCCCGG AAGGTCGAGC CGCGGGCAG 720
 721 CGTGAACTGG TCCTGGTTCT CGAAGCTCTG GCCGTTGACA TGGGCGAACT TCGGGCAGTC 780
 781 GGCCCGCTCC TCCGGGTTCA TCCCCTGCTG GAGCAGGGCC GCGGTGGTGA CCACCTTGAA 840
 841 GGTGGAGCCG GCGGGTAGC GGCCCTCCAG CGCGCGGTTC ATGCCGGAGG GCACGTTCGC 900
 901 GGCGGCCAGG ATGTTGCCGG TGGCGGGGTC GACGGCGACG ATCGCCGCGT TCTTCTTCGA 960
 961 GCCCTCCAGG GCCGCCGCGG CGGCGGACTG GACCCGCGGG TCGATGGTGG TCTTCACCGG 1020
1021 CTTGCCCTCG GTGTCCTTGA GGCCGGTGAG CTTCTTGACC ACCTGGCCGG ACTCACGGTC 1080
1081 CAGGATCACG ACCGAGCGCG CCGCGCCGGA GCCGCCGGTG AGCTGCTTGT CGTAGCGGGA 1140
1141 CTGGAGGCCC GCCGAGCCCT TGCCGGTCCT GGGGTCGACC GCGCCGATGA TGGAGGCGGC 1200
1201 CTGGAGGACA TTGCCGTTGG CGTCGAGGAT GTCCGCGCGC TCCCGCGACT TGAGGGCGAG 1260
1261 GGTCTGCCCC GGAACCATCT GCGGATGGAT CATCTCGGTG TTGAACGCGA CCTTCCACTC 1320
1321 CTTGCCGCCG CCGACGACCT TCGCGGTGGA GTCCAGGCG TACTCCCCGG CCCCGGGGAG 1380
1381 GGTCATTCTG ACGGTGAACG GTATCTCCAC CTCGCCCTCG GGGTTCTTCT CCCCGGTCTT 1440
1441 GGCGGTGATC TCCGTCTTCG TCGGCTTGAG GTTGGTCATG ACGGATTTGA TCAGCGACTC 1500
1501 GGCGTTGTCC GGGGTGTCCG TCAGCCCGGC GGCCGTCGGG GCGTCGCCCT TCTCCCAGGC 1560
```

FIGURE 2B

```
1561 GCCGAGGAAG GTGTCGAACT GTCCGGCCGC CGCCTCCACC TCGGGTCGC CCGAATCCTT 1620
1621 CTCGTCGGCA ACCAGGCTGG TGTAACCCCA ATAGCCGAGC CCCACCGTCA CGGCCAGCCC 1680
1681 GGCGACCACC GCGGTGGCCG CCCGGCCACG GGAGCGGCGC CTGCCCTGCG GCGGGTCATC 1740
     <--Beginning of ORF 1
1741 GCCATAGTTG TCGGAATGCG TCATggggcc aggctatgcg ggcgccctct ttccctcctc 1800
1801 cccggatacc gcgtttcagg acagtcaagg ggccgaacgg agggctggac cagccgctca 1860
1861 gcggcccgtt cccaccccTT ggggggaagc ggcacccgga aggtgaccga ggcaacatcc 1920
1921 atggaaaggg gagcgaatcg gtcgccgagt tcaccgcgat tggagtagac ctctgaaagc 1980
1981 gtgacagcgg ggagtagcga caaaacggtc agaccctga agggaattga ctgaattcga 2040
2041 gtcatcgggt tcggcgacgg atgggcggtt cggccacgca ccgtcactct tcgtccctc 2100
2101 ttcacaagaa ctcccgatac gtggagaaga gagcgtgaag agcgcgtccg gtcagggttg 2160
                                                            Begin-
2161 ccgagaaccg tccaccatga cggagcctgg tactgacgga gtctggagac cgctcATGTC 2220
     ning of ORF 2-->
2221 CCGTGTATCG ACCGCCCCCA GCGGCAAGCC TACCGCCGCT CACGCCCTCC TGTCACGGTT 2280
2281 GCGTGATCAC GGTGTGGGGA AGGTGTTTGG GGTTGTCGGC CGAGAGGCCG CGTCGATTCT 2340
2341 CTTCGACGAG GTCGAGGGGA TCGACTTCGT TCTGACCCGC CACGAGTTCA CCGCGGGTGT 2400
2401 CGCCGCTGAT GTCCTCGCGC GGATCACCGG TCGCCCCAG GCGTGCTGGG CCACCCTGGG 2460
2461 CCCCGGTATG ACCAACCTCT CCACCGGTAT CGCCACGTCC GTCCTGGACC GCTCGCCGGT 2520
2521 CATCGCGCTC GCCGCGCAGT CGGAGTCGCA CGACATCTTC CCGAACGACA CCCACCAGTG 2580
2581 CCTGGACTCG GTGGCGATCG TCGCCCCGAT GTCCAAGTAC GCCGTGGAGC TCCAGCGGCC 2640
2641 CCACGAGATC ACCGACCTCG TCGACTCCGC CGTGAACGCG GCCATGACCG AGCCGGTCGG 2700
2701 GCCCTCCTTC ATCTCCCTCC CGGTGGACCT GCTCGGCTCC TCCGAGGGCA TCGACACCAC 2760
2761 CGTCCCCAAC CCGCCGGCGA ACACCCCGGC GAAACCGGTC GGCGTCGTCG CCGACGGCTG 2820
2821 GCAGAAGGCC GCCGACCAGG CCGCCGCCCT GCTCGCCGAG GCCAAGCACC CGGTGCTCGT 2880
2881 CGTCGGAGCG GCCGCGATCC GCTCGGGCGC CGTCCCGGCG ATCCGCGCCC TGGCCGAGCG 2940
2941 CCTGAACATC CCGGTCATCA CGACCTACAT CGCCAAGGGT GTCCTGCCGG TCGGCCACGA 3000
3001 GCTGAACTAC GGCGCCGTCA CCGGCTACAT GGACGGCATC CTCAACTTCC CGGCGCTCCA 3060
3061 GACCATGTTC GCCCCGGTGG ACCTCGTCCT CACCGTCGGC TACGACTACG CCGAGGACCT 3120
3121 GCGCCCGTCC ATGTGGCAGA AGGGCATCGA GAAGAAGACC GTCCGTATCT CCCCGACGGT 3180
3181 CAACCCGATC CCCCGGGTCT ACCGGCCCGA CGTCGACGTC GTCACCGACG TCCTCGCCTT 3240
```

FIGURE 2C

```
3241 CGTGGAGCAC TTCGAGACCG CGACCGCCTC CTTCGGGGCC AAGCAGCGCC ACGACATCGA 3300

3301 GCCGCTGCGC GCCCGGATCG CGGAGTTCCT GGCCGACCCG GAGACCTACG AGGACGGCAT 3360

3361 GCGCGTCCAC CAGGTCATCG ACTCCATGAA CACCGTCATG GAGGAGGCCG CCGAGCCCGG 3420

3421 CGAGGGCACG ATCGTCTCCG ACATCGGCTT CTTCCGTCAC TACGGTGTGC TCTTCGCCCG 3480

3481 CGCCGACCAG CCCTTCGGCT TCCTCACCTC GGCGGGCTGC TCCAGCTTCG GCTACGGCAT 3540

3541 CCCCGCCGCC ATCGGCGCCC AGATGGCCCG CCCGGACCAG CCGACCTTCC TCATCGCGGG 3600

3601 TGACGGCGGC TTCCACTCCA ACAGCTCCGA CCTGGAGACC ATCGCCCGGC TCAACCTGCC 3660

3661 GATCGTGACC GTCGTCGTCA ACAACGACAC CAACGGCCTG ATCGAGCTGT ACCAGAACAT 3720

3721 CGGTCACCAC CGCAGCCACG ACCCGGCGGT CAAGTTCGGC GGCGTCGACT TCGTCGCGCT 3780

3781 CGCCGAGGCC AACGGTGTCG ACGCCACCCG CGCCACCAAC CGCGAGGAGC TGCTCGCGGC 3840

3841 CCTGCGCAAG GGTGCCGAGC TGGGTCGTCC GTTCCTCATC GAGGTCCCGG TCAACTACGA 3900
                                   End of ORF 2--> Beginning of ORF 3-->
3901 CTTCCAGCCG GGCGGCTTCG GCGCCCTGAG CATCTGAtcA TGGGGCACC GGTTCTTCCG 3960

3961 GCTGCCTTCG GGTTCCTGGC CTCCGCCCGA ACGGGCGGGG GCCGGGCCCC CGGCCCGGTC 4020

4021 TTCGCGACCC GGGGCAGCCA CACCGACATC GACACGCCCC AGGGGGAGCG CTCGCTCGCG 4080

4081 GCGACCCTGG TGCACGCCCC CTCGGTCGCG CCCGACCGCG CGGTGGCGCG CTCCCTCACC 4140

4141 GGCGCGCCCA CCACCGCGGT GCTCGCCGGT GAGATCTACA ACCGGGACGA ACTCCTCTCC 4200

4201 GTGCTGCCCG CCGGACCCGC GCCGGAGGGG GACGCGGAGC TGGTCCTGCG GCTGCTGGAA 4260

4261 CGCTATGACC TGCATGCCTT CCGGCTGGTG AACGGGCGCT TCGCGACCGT GGTGCGGACC 4320

4321 GGGGACCGGG TCCTGCTCGC CACCGACCAC GCCGGTTCGG TGCCGCTGTA CACCTGTGTG 4380

4381 GCGCCGGGCG AGGTCCGGGC GTCCACCGAG GCCAAGGCGC TCGCCGCGCA CCGCGACCCG 4440

4441 AAGGGCTTCC CGCTCGCGGA CGCCCGCCGG GTCGCCGGTC TGACCGGTGT CTACCAGGTG 4500

4501 CCCGCGGGCG CCGTGATGGA CATCGACCTC GGCTCGGGCA CCGCCGTCAC CCACCGCACC 4560

4561 TGGACCCCGG GCCTCTCCCG CCGCATCCTG CCGGAGGGCG AGGCCGTCGC GGCCGTGCGG 4620

4621 GCCGCGCTGG AGAAGGCCGT CGCCCAGCGG GTCACCCCCG GCGACACCCC GTTGGTGGTG 4680

4681 CTCTCCGGCG GAATCGACTC CTCCGGGGTC GCGGCCTGTG CGCACCGGGC GGCCGGGGAA 4740

4741 CTGGACACGG TGTCCATGGG CACCGACACG TCCAACGAGT TCCGCGAGGC CCGGGCGGTC 4800

4801 GTCGACCATC TGCGCACCCG GCACCGGGAG ATCACCATCC CGACCACCGA GCTGCTGGCG 4860
```

FIGURE 2D

```
4861 CAGCTCCCGT ACGCGGTGTG GGCCTCCGAG TCGGTGGACC CGGACATCAT CGAGTACCTG 4920
4921 CTCCCCCTGA CAGCGCTCTA CCGGGCGCTC GACGGGCCGG AGCGCCGCAT CCTCACCGGG 4980
4981 TACGGCGCGG ACATCCCCCT CGGGGGCATG CACCGCGAGG ACCGGCTGCC CGCGCTGGAC 5040
5041 ACCGTTCTCG CGCACGACAT GGCCACCTTC GACGGGCTGA ACGAGATGTC CCCGGTGCTG 5100
5101 TCCACGCTGG CGGGGCACTG GACCACCCAC CCGTACTGGG ACCGGGAGGT CCTCGATCTG 5160
5161 CTGGTCTCGC TGGAGGCCGG GCTCAAGCGG CGGCACGGCC GGGACAAGTG GGTGCTGCGC 5220
5221 GCCGCGATGG CCGACGCCCT CCCGGCGGAG ACCGTCAACC GGCCCAAGCT GGGCGTCCAC 5280
5281 GAGGGCTCGG GCACCACGTC CTCGTTCTCC CGGCTGCTGC TGGACCACGG TGTCGCCGAG 5340
5341 GACCGCGTCC ACGAGGCGAA GCGGCAGGTG GTGCGCGAGC TGTTCGATCT CACGGTCGGG 5400
5401 GGCGGACGGC ACCCCTCCGA GGTGGACACC GACGATGTGG TGCGCTCCGT GGCCGACCGG 5460
                End of ORF 3-->
5461 ACCGCGCGGG GGGCGGCCTA Gtcccgccac ggggagcccg ccggacgccg gacccgcgcg 5520
5521 ggacccgtac ccggggccgc ccgcggactc cggcgcaccg gcacccctgt ccccacccg 5580
5581 ttgacgaccg tcggccctcg gccctcgcgg ccctgacga ccgtcgcccg attcccagga 5640
              Beginning of ORF 4-->
5641 gggagctgaa agcGTGGAGC GCATCGACTC GCACGTTTCA CCCCGCTACG CACAGATCCC 5700
5701 CACCTTCATG CGCCTGCCGC ACGATCCCCA GCCCGCGGC TATGACGTGG TGGTCATCGG 5760
5761 AGCCCCCTAC GACGGGGGCA CCAGCTACCG TCCCGGCGCC CGGTTCGGCC CCCAGGCCAT 5820
5821 CCGCAGTGAG TCGGGCCTCA TCCACGGTGT CGGCATCGAC CGGGGCCCCG GCACGTTCGA 5880
5881 CCTGATCAAC TGTGTCGACG CCGGGGACAT CAATCTGACG CCGTTCGACA TGAACATCGC 5940
5941 GATCGACACG GCGCAGAGCC ATCTGTCGGG CCTGCTGAAG GCCAACGCCG CCTTTCTGAT 6000
6001 GATCGGCGGC GACCACTCGC TGACGGTGGC CGCCCTGCGC GCGGTCGCGG AGCAGCACGG 6060
6061 CCCGCTCGCC GTGGTGCACC TGGACGCGCA CTCCGACACC AACCCGGCCT TCTACGGGGG 6120
6121 CCGGTACCAC CACGGCACCC CCTTCCGGCA CGGGATCGAC GAGAAGCTGA TCGACCCGGC 6180
6181 GGCGATGGTC CAGATCGGCA TCCGGGGCCA CAACCCGAAG CCGGACTCGC TCGACTACGC 6240
6241 CCGGGGCCAC GGCGTCCGGG TGGTCACGGC GGACGAGTTC GGCGAGCTGG GGGTGGGCGG 6300
6301 GACCGCCGAC CTCATCCGCG AGAAGGTCGG CCAGCGGCCC GTGTACGTCT CGGTCGACAT 6360
6361 CGACGTGGTC GACCCCGCCT TCGCCCCCGG TACGGGCACG CCCGCGCCGG GCGGGCTCCT 6420
6421 CTCGCGCGAG GTGCTGGCGC TGCTGCGCTG CGTGGGTGAC CTGAAGCCGG TCGGCTTCGA 6480
6481 CGTGATGGAG GTGTCACCCC TCTACGACCA CGGCGGGATC ACTTCGATCC TGGCCACGGA 6540
```

FIGURE 2E

```
                                                     End of ORF 4-->
6541  GATCGGTGCG GAACTGCTCT ACCAGTACGC CCGAGCCCAC AGAACCCAGT TGTGAaggag 6600
                                       Beginning of ORF 5-->
6601  acatcgtgtc ATGGCCTCTC CGATAGTTGA CTGCACCCCG TACCGCGACG AGCTGCTCGC 6660
6661  GCTCGCCTCC GAGCTTCCCG AGGTGCCGCG CGCGGACCTC CATGGCTTCC TCGACGAGGC 6720
6721  GAAGACGCTG GCCGCCCGTC TCCCGGAGGG GCTGGCCGCC GCTCTCGACA CCTTCAACGC 6780
6781  CGTGGGCAGC GAGGACGGTT ATCTGCTGCT GCGCGGGCTG CCCGTCGACG ACAGCGAGCT 6840
6841  GCCCGAGACG CCGACCTCCA CCCCGGCCCC GCTGGACCGC AAGCGGCTGG TGATGGAGGC 6900
6901  CATGCTCGCG CTGGCCGGCC GCCGGCTCGG TCTGCACACG GGGTACCAGG AGCTGCGCTC 6960
6961  GGGCACGGTC TACCACGACG TGTACCCGTC GCCCGGCGCG CACTACCTGT CCTCGGAGAC 7020
7021  CTCCGAGACG CTGCTGGAGT TCCACACGGA GATGGCGTAC CACATCCTCC AGCCGAACTA 7080
7081  CGTCATGCTG GCCTGCTCCC GCGCGGACCA CGAGAACCGG GCGGAGACGC TGGTCGGCTC 7140
7141  GGTCCGCAAG GCGCTGCCCC TGCTGGACGA GAAGACCCGG GCCCGTCTCT TCGACCGCAA 7200
7201  GGTGCCCTGC TGCGTGGACG TGGCCTTCCG CGGCGGGGTC GACGACCCGG GCGCGATCGC 7260
7261  CAACGTCAAG CCGCTCTACG GGACGCGAA  CGACCCGTTC CTCGGGTACG ACCGCGAGCT 7320
7321  GCTGGCGCCG GAGGACCCCG CGGACAAGGA GGCCGTCGCC CATCTGTCCC AGGCGCTCGA 7380
7381  CGATGTGACC GTCGGGGTGA AGCTCGTCCC CGGTGACGTC CTCATCATCG ACAACTTCCG 7440
7441  CACCACGCAC GCGCGGACGC CGTTCTCGCC CCGCTGGGAC GGGAAGGACC GCTGGCTGCA 7500
7501  CCGCGTCTAC ATCCGCACCG ACCGCAATGG ACAGCTCTCC GGCGGCGAGC GCGCGGGCGA 7560
                          End of ORF 5-->
7561  CACCATCTCG TTCTCGCCGC GCCGCTGAgc ccggctcccc gaggccctgg gccccggcgc 7620
7621  cggaaccggc tcccggtcct gccccctcac ccgccgcgcg ggtgaggggg caggcccctt 7680
7681  tgtgccgggt gccgtgcgtc ctgcgagggt gccggggcgg gggggacggc ggaggtgccc 7740
7741  ggcggccggg tgccgtgcgc cgcccgtggg tgctgtacag cactccgtgt gccgtgcgcc 7800
7801  accccgtgca taaatttgcc actctatggg aaataatgca gagtgcgacg ggtgaggccg 7860
                                                  Beginning of ORF 6-->
7861  tcgccgtgcc ctttccgtga caggagacgc tgacATGTCC GACAGCACAC CGAAGACGCC 7920
7921  CCGGGGATTC GTGGTGCACA CGGCGCCGGT GGGCCTGGCC GACGACGGCC GCGACGACTT 7980
7981  CACCGTCCTC GCCTCCACCG CCCCGGCCAC CGTGAGCGCC GTCTTCACCC GCTCCCGCTT 8040
8041  CGCCGGGCCG AGCGTCGTGC TGTGCCGGGA GGCGGTGGCC GACGGGCAGG CGCGCGGTGT 8100
8101  GGTGGTGCTG GCCCGCAACG CGAATGTCGC GACCGGCCTG GAGGGCGAGG AGAACGCGCG 8160
```

FIGURE 2F

```
8161 CGAGGTGCGC GAGGCCGTCG CCCGGGCCCT CGGGCTGCCG GAGGGCGAGA TGCTGATCGC 8220

8221 CTCCACCGGG GTGATCGGCC GGCAGTACCC GATGGAGAGC ATCCGGGAGC ACCTCAAGAC 8280

8281 GCTGGAGTGG CCCGCCGGGG AGGGCGGCTT CGACCGCGCG GCCCGCGCCA TCATGACGAC 8340

8341 CGACACCCGG CCCAAGGAGG TCCGGGTCAG CGTCGGCGGG GCGACCCTCG TGGGCATCGC 8400

8401 CAAGGGCGTC GGCATGCTGG AGCCCGACAT GGCGACGCTG CTGACCTTCT TCGCCACGGA 8460

8461 CGCCCGGCTG GACCCGGCCG AGCAGGACCG CCTCTTCCGC CGGGTCATGG ACCGCACCTT 8520

8521 CAACGCGGTC AGCATCGACA CCGACACCTC CACCAGCGAC ACGGCGGTGC TGTTCGCCAA 8580

8581 CGGCCTGGCG GGCGAGGTCG ACGCCGGGGA GTTCGAGGAG CGCTGCACA CGGCGGCGCT 8640

8641 GGCCCTGGTC AAGGACATCG CGAGCGACGG CGAGGGCGCG GCCAAGCTGA TCGAGGTCCA 8700

8701 GGTCACCGGC GCCCGCGACG ACGCCCAGGC CAAGCGGGTC GGCAAGACCG TCGTCAACTC 8760

8761 CCCGTTGGTG AAGACCGCCG TGCACGGCTG CGACCCCAAC TGGGGCCGGG TCGCCATGGC 8820

8821 GATCGGCAAG TGCTCGGACG ACACCGACAT CGACCAGGAG CGGGTGACGA TCCGCTTCGG 8880

8881 CGAGGTCGAG GTCTATCCGC CGAAGGCCCG GGGCGACCAG GCCGACGACG CGCTGCGGGC 8940

8941 CGCCGTCGCG GAGCATCTGC GGGGCGACGA GGTGGTCATC GGGATCGACC TCGCCATCGC 9000

9001 GGACGGGGCC TTCACCGTCT ACGGCTGCGA CCTCACCGAG GGCTATGTCC GGCTGAACTC 9060
         End of ORF 6-->
9061 GGAGTACACC ACCTGAtccc cggacaggga acgggccgcc gcccgttcc ctgtccgctc 9120

9121 ccgtccgtg tggttatacc gaccgttccc cggctatgcg cacgggacgg agcggccccc 9180

9181 gccgggcccc gcccggccgc acgatgaggg gcgatgcaag gtgacgaggg caggagggac 9240
         Beginning of ORF 7-->
9241 ATGGAGACCA CTCGGTCGAC GACCGCGGAC GAGGGCTTCG ACGCCGGGGT ACGGGGAGTG 9300

9301 GTCGCGCCGA CCGACGCCCC GGGCGGGACG CTGCGGCTGG TCCGCACGGA CGACTTCGAC 9360

9361 TCGCTCGACC CCGGCAACAC GTACTACGCC TACACCTGGA ACTTCCTCCG GCTCATCGGC 9420

9421 CGGACGCTGG TCACCTTCGA CACCGCGCCG GGCAAGGCGG CCAGCGGCT CGTGCCCGAC 9480

9481 CTCGCCGAGT CGCTGGGCGA GTCCTCCGAG GACGGCCGGG TCTGGACCTA CCGGCTGCGC 9540

9541 GAGGGCCTGC GCTACGAGGA CGGCACGCCG GTCGTCTCGG CCGACATCAA GCACGCCATC 9600

9601 GCCCGCAGCA ACTACGGCAC CGATGTCCTG GGCGCCGGTC CGACCTACTT CCGCCACCTC 9660

9661 CTGGGCACCG AGTACGGCGG CCCCTGGCGG GAGCCGGACG CCGACGGACC GGTGACGCTG 9720

9721 GAGACCCCGG ACGAGCGGAC GCTGGTCTTC CGGCTGCGGG AGCCGTTCGC GGGGATGGAT 9780

9781 CTGCTGGCGA CCATGCCGTC CACCACCCCC GTGCCGCGCG ACCGGGACAC CGGCGCCGAG 9840
```

FIGURE 2G

```
 9841 TACCGGCTGC GGCCCGTGGC GACCGGCCCG TACCGGATCG TCTCGTACAC CCGGGGCGAG  9900
 9901 CTGGCCGTCC TGGAGCCCAA TCCGCACTGG GACCCCGAGA CCGACCCGGT GCGCGTCCAG  9960
 9961 CGCGCCTCCC GGATCGAGGT GCACCTCGGC AAGGACCCGC ACGAGGTGGA CCGCATGCTG 10020
10021 CTGGCGGGCG AGGCCCATGT GGACCTCGCG GGCTTCGGTG TGCAGCCCGC GGCCCAGGAG 10080
10081 CGCATCCTCG CCGAGCCGGA GCTGCGCGCG CACGCGGACA ACCCGCTGAC CGGCTTCACC 10140
10141 TGGATCTACT GCCTGTCGAG CCGGATCGCC CCGTTCGACA ATGTGCACTG CCGGCGGGCC 10200
10201 GTGCAGTTCG CCACCGACAA AGCGGCCATG CAGGAGGCGT ACGGCGGCGC GGTGGGCGGC 10260
10261 GACATCGCGA CCACCCTGCT GCCCCCGACC CTCGACGGCT ACAAGCACTT CGACCGCTAC 10320
10321 CCGGTCGGCC CGAGGGCAC  CGGCGACCTG GAGGCCGCCC GCGCCGAGCT GAAGCTGGCC 10380
10381 GGGATGCCCG ACGGCTTCCG CACCAGGATC GCCGCCCGCA AGGACCGGCT CAAGGAGTAC 10440
10441 CGGGCCGCCG AGGCGCTGGC CGCCGGGCTC GCCCGGGTCG GCATCGAGGC GGAGGTGCTG 10500
10501 GACTTCCCGT CGGGCGACTA CTTCGACCGC TACGGCGGCT GCCCGGAGTA TCTGCGCGAG 10560
10561 CACGGGATCG GGATCATCAT GTTCGGCTGG GGCGCCGACT TCCCCGACGG ATACGGCTTC 10620
10621 CTCCAGCAGA TCACCGACGG GCGCGCGATC AAGGAGCGCG GCAACCAGAA CATGGGCGAG 10680
10681 CTGGACGACC CGGAGATCAA CGCGCTGCTG GACGAGGGGG CGCAGTGCGC CGACCCGGCG 10740
10741 CGGCGCGCGG AGATCTGGCA CCGCATCGAC CAGCTCACGA TGGACCACGC GGTCATCGTT 10800
10801 CCGTATCTGT ACCCGCGGTC CCTGCTCTAC CGGCACCCGG ACACCCGCAA CGCCTTCGTC 10860
                                                End of ORF 7-->
10861 ACCGGCTCCT TCGGGATGTA CGACTACGTG GCGCTCGGCG CGAAGTGAgc acggggtccg 10920
10921 gccccgggac cgtatgtccc ggggccggac cccgcccgtt ccccgcccgg tccggtccgg 10980
                       <--End of ORF 8
10981 acccggtcgc ggcccgcTCA GCCGGACATC CGGGCCCCGG CCGCGACCCC GCGCCGGATC 11040
11041 GGCCAGTGGC CCTGCGCCAG GGGCCGTTCC ACGCTGCGGC AGGCGAGAGC GGCCTCGCGG 11100
11101 AACTCCGCCT CGTACAGCGC GAGCTGGCGC AGGAACTGCC GGGTCGGGCC GGTCAGGCTG 11160
11161 GTCCCCGCG  GGCTGCGCAG CAGCAGCCGG GCGCCGAGGG ACTGCTCCAG CCGGTGAATC 11220
11221 CGGCGGGTGA CGCCGACTG  GCTGATCGAC AGCACCGCCG CGGCCCGGTT GATGCTGCCG 11280
11281 TGCCGGGCCA CGGCCTGGAG CAGATGGAGA TCGTCCACAT CCAGTTTGCG GCCCTCGGCC 11340
11341 TGGCCGGGCA CGGAGCCCTG GTCGGGTCCC GCCCCGAAGC GGCGGGCGTC CGCGCCGGTG 11400
11401 CGCTCCGCGT ACCACTGCGC CCACCAGGGC TCGTCCAGCA GGTCGCGGTG GTGTTCGGCG 11460
11461 AAGCGCCGGA GCTGGACCTC GGCGATCAGC GCGGCCAGCC GTCCCGCCAG CGCCCGGGGC 11520
```

FIGURE 2H

```
11521  ACGATGGTGG GGTCGACGAG CAGACTCGTG GTGCGGCGCG GGCGCTCCGC CAGGGAGCGG  11580
11581  CGCACCAGCG AGGGGTCCTG CACCGCCGGG TGGGTGGGCG AGCCGAGACC TATCGCGTCC  11640
11641  CCGCGGCGCA GGATGCCCCG GGCAACCGAT GCCCCCGTGA TGTGGAGCCG GGTGGGCGCG  11700
11701  GTGAGCCCGG CCAGCTGGAA GACACGTGTC ACCAGGATCT CCGAGCCGGG TCCCGTCTCG  11760
11761  GACACCCAGG TCTCGTCCCG CAGATCGGCG AGCGAGACCT CCCGCCGGGC GGCCAGCGGA  11820
11821  TGGTCCCGGG GCAGGATCAC CCACAGCGGG TCGTCCAGCA CCTCACAGGT GCGCACGGAC  11880
11881  CGCTCCAGGC TGTGCCGGGG GGACTGGAGG CTCCAGGTGT AGGCCGCGTC CACCTGGTAG  11940
11941  CCCGCCAGTT GGGCGGCGAC CTGGTGCGGG GCCTCGTGCC GGACCGACAG CAGCAGGTCC  12000
12001  AGCGAGGCCG CCGCGTCCTC CACCACCTCG TCGAGCAGGG GTTCCGTGGA GACCAGCGAC  12060
12061  AGCACCTCCG GGGCGTCCAC GGCCTCGGAG CCATGGCCGA AGATATGCGT CCGCGCGGCC  12120
12121  AGGTCGACCT GGTGGAAGAA CCGCCGCCCG GCGACGAGGA TGCGGGAGCC CGCGGTGGTC  12180
12181  AGCCGGGCCG TGTGGCGGCT GCGCAGGGTC AGCGGGAGGC CGACGATCCG GTCCAGCCGG  12240
                                                     <--beginning of ORF 8
12241  TCGAGTCTGC GCTCCACGGT GCCGTGCCGG ACACCCGTCC GCCGGGCCAC TTCCATgagg  12300
12301  tctccgcagt gtccaccgc gtccagtaaa gacagatcgc atcggctgac accagcagac  12360
12361  gtcggttctg acccgagaga caatgtcggt tcccttttcc gtcaaggact gtaccgctga  12420
12421  attgtccgaa gtggctcttg aattgcttcg gaatcgatcc taggcagcgc cgctcttcgg  12480
12481  attctcctcg ccgggaagcg gaacgcgccc ggccggatgg cgggcgcgct ccgggcgccg  12540
12541  tcccgggaac ggggggacggg gcacggcacg gccggccacc cggtccgggc gcgcggcgtg  12600
                                   <--end of ORF 9
12601  gacctggtcg gcggacgggt gTCAGACCTG GTCGGTGGGG CGTATGAAGA TCTCGTGGAC  12660
12661  GGTCGCGTGG TGCGGCGCGG TCACGGCGTA GCGGACCGCC TCCGCGATGT CCTGGGCCTG  12720
12721  GAGCTTGCGG ATCTGGCTGA TCCGCTGCTC GTACATCTCC TTGGTGGCGG TGTGGGTGAT  12780
12781  GTGGCCGCGC AGCTCCGTGT CGGTGGTGCC CGGCTCGATG ACGACGACCC GCACCCCGCG  12840
12841  CTCGGTGACC TCCTGGCGCA GCGTCTCGCT GAACGCGTTC ACACCGAACT TCGTGGCCTG  12900
12901  GTAGACGGCC GCGTTGCGGA CGTTCACCCG GCCCGCGATC GAGGACATCT GCACCACGGT  12960
12961  GCCCTTGCTG CGCAGCAGAT GGGGAAGGGC CGCCCGGGTC ATGTACATCA GGCCCAGGAG  13020
13021  ATTGGTGTCG ATCATCCGGG TCCAGTCGGT GGTGTCGGCG TCCTCCACCG GGCCGAGCAG  13080
13081  CATGATCCCG GCGTTGTTGA CGAGGATGTC GAGGCCGCCC AGCGCCTCGA CGGTGGAGGC  13140
13141  GACGGCGGCG TCCACCCCCT GCCGGTCGGC GACGTCGAGT TCGAGGACAT GGACCTTCGC  13200
```

FIGURE 21

```
13201 CCCGGCGGCG GTCAGCTCGT CACCCAGGGC GCGCAGCTTC TCGACCCGGC GCGCGGCGAT 13260

13261 GGCCACGGCG GCGCCCTCGG CGGCCAGGGC GCGGGCCGTG GCCTCGCCGA TGCCCGAGCT 13320
                                   <---beginning of ORF 9
13321 CGCGCCCGTG ATGAGCGCGA CTTTCCCCTG GAGTGCGGAT GGCATcattt cctccacatg 13380

13381 gtgctgcgat cgtggtgagc gtatgaagaa ggggtgagac ctgccgtgcc ggggcgggtt 13440

13441 ccgtacgccg gaccgttgcg gtgggcacgg ccgaccgggt acggatggcc gcagttcccc 13500

13501 ggggagttcc cggggaatgg tgaataccgc ggcgctctcc gatggtcttc ggaggacacc 13560

13561 cggggattca ccgggaatca gcggccggag ttctccccgt ccacggcaga cgctatcagc 13620

13621 gtcgcattcc ccggtgaatt cccttcggtg gaccgggtta tgactgtttc cgccgggtta 13680

13681 tgcgcgccgc cccggcggac cggccacccg cccgggggct gcggcagatt gggcgccacg 13740
                                           Beginning of ORF 10--->
13741 acatggcgcg agcagcgatc ggcggtggAT GATGAACGAG GCAGCGCCTC AGTCCGACCA 13800

13801 GGTGGCACCG GCGTATCCGA TGCACCGGGT CTGCCCGGTC GACCCGCCGC CGCAACTGGC 13860

13861 CGGGCTGCGG TCCCAGAAGG CCGCGAGCCG GGTGACGCTG TGGGACGGCA GCCAGGTGTG 13920

13921 GCTGGTGACC TCGCACGCCG GGGCCCGGGC CGTCCTGGGC GACCGCCGCT TCACCGCGGT 13980

13981 GACGAGCGCG CCCGGCTTCC CGATGCTGAC CCGCACCTCC CAACTGGTGC GCGCCAACCC 14040

14041 GGAGTCGGCG TCGTTCATCC GCATGGACGA CCCGCAGCAC TCCCGGCTGC GCTCGATGCT 14100

14101 CACCCGGGAC TTCCTGGCCC GCCGCGCCGA GGCGCTGCGC CCCGCGGTGC GGGAGCTGCT 14160

14161 GGACGAGATC CTGGGCGGGC TGGTGAAGGG GGAGCGGCCG GTCGACCTGG TCGCCGGACT 14220

14221 GACGATCCCG GTGCCCTCGC GGGTCATCAC CCTGCTCTTC GGCGCCGGTG ACGACCGCCG 14280

14281 GGAGTTCATC GAGGACCGCA GCGCGGTCCT CATCGACCGC GGCTACACCC CGGAGCAGGT 14340

14341 CGCCAAGGCC CGGGACGAAC TCGACGGCTA TCTGCGGGAG CTGGTCGAGG AGCGGATCGA 14400

14401 GAACCCGGGC ACCGACCTGA TCAGCCGGCT CGTCATCGAC CAGGTGCGGC CGGGGCATCT 14460

14461 GCGGGTCGAG GAGATGGTCC CGATGTGCCG GCTGCTGCTG GTGGCCGGTC ACGGCACCAC 14520

14521 CACCAGCCAG GCGAGCCTGA GCCTGCTCAG CCTGCTCACC GACCCGGAGC TGGCCGGGCG 14580

14581 CCTCACCGAG GACCCGGCCC TGCTGCCCAA GGCGGTCGAG GAGCTGCTGC GCTTCCACTC 14640

14641 CATCGTGCAG AACGGGCTGG CCCGTGCCGC GGTGGAGGAC GTCCAGCTCG ACGATGTGCT 14700

14701 CATCCGGGCG GGCGAGGGCG TGGTGCTGTC GCTGTCGGCG GGCAACCGGG ACGAGACGGT 14760

14761 CTTCCCCGAC CCGGACCGGG TGGACGTGGA CCGCGACGCC CGCCGCCATC TCGCCTTCGG 14820

14821 CCACGGCATG CACCAGTGCC TGGGCCAGTG GCTGGCCCGG GTGGAGCTGG AGGAGATCCT 14880
```

FIGURE 2J

```
14881 CGCCGCGGTG CTGCGCTGGA TGCCCGGTGC CCGGCTCGCG GTGCCCTTCG AGGAGCTGGA 14940
                                                    end of ORF 10-->
14941 CTTCCGTCAT GAGGTGTCCA GTTACGGCCT CGGCGCCCTC CCGGTGACCT GGTGAgcggc 15000

15001 gtggagcggc tgaccgtcgt cctcgacgcg tcggcctgct gcgcgatggg gcgctgcgcg 15060

15061 gccacggccc ccgagatct                                              15079
              |    10    |    20    |    30    |    40    |    50    |    60
```

ORF 4 = cla

```
      |   10        |   20        |   30         |   40        |   50        |   60
  1 MTHSDNYGDD PPQGRRRSRG RAATAVVAGL  AVTVGLYWG  YTSLVADEKD SGDPEVEAAA  60
 61 GQFDTFLGAW EKGDAPTAAG LTDTPDNAES LIKSVMTNLK PTKTEITAKT GEKNPEGEVE 120
121 IPFTVRMTLP GAGEYAWDST AKVVGGGKEW KVAFNTEMIH PQMVPGQTLA LKSRERADIL 180
181 DANGNVLQAA SIIGAVDPRT GKGSAGLQSR YDKQLTGGSG AARSVVILDR ESGQVVKKLT 240
241 GLKDTEGKPV KTTIDPRVQS AAAAALEGSK KNAAIVAVDP ATGNILAAAN VPSGMNRALE 300
301 GRYPPGSTFK VVTTAALLQQ GMNPEERADC PKFAHVNGQS FENQDQFTLP AGSTFRDSFA 360
361 HSCNTFFVNS RSKLSESSLK QAAEAFGIGG TWDVGASTFD GSVPVSNSEN DKAASTIGQA 420
421 RVEASPLVMA SIAATVKQGE FKQPVLVPDA VKKPHQAPRM APGIVDSLRS MMRSTVTDGA 480
481 GDALRGLGGQ PHAKTGTAEF GTEKPPKTHA WMIGYQGDRN IAWSVLLEDG GSGGADAGPV 540
541 AAKFLSNLAA GZ                                                      552
      |   10        |   20        |   30         |   40        |   50        |   60
```

FIGURE 9

```
         |   10       |   20       |   30       |   40       |   50       |   60
   1 MSRVSTAPSG KPTAAHALLS RLRDHGVGKV FGVVGREAAS ILFDEVEGID FVLTRHEFTA  60
  61 GVAADVLARI TGRPQACWAT LGPGMTNLST GIATSVLDRS PVIALAAQSE SHDIFPNDTH 120
 121 QCLDSVAIVA PMSKYAVELQ RPHEITDLVD SAVNAAMTEP VGPSFISLPV DLLGSSEGID 180
 181 TTVPNPPANT PAKPVGVVAD GWQKAADQAA ALLAEAKHPV LVVGAAAIRS GAVPAIRALA 240
 241 ERLNIPVITT YIAKGVLPVG HELNYGAVTG YMDGILNFPA LQTMFAPVDL VLTVGYDYAE 300
 301 DLRPSMWQKG IEKKTVRISP TVNPIPRVYR PDVDVVTDVL AFVEHFETAT ASFGAKQRHD 360
 361 IEPLRARIAE FLADPETYED GMRVHQVIDS MNTVMEEAAE PGEGTIVSDI GFFRHYGVLF 420
 421 ARADQPFGFL TSAGCSSFGY GIPAAIGAQM ARPDQPTFLI AGDGGFHSNS SDLETIARLN 480
 481 LPIVTVVVNN DTNGLIELYQ NIGHHRSHDP AVKFGGVDFV ALAEANGVDA TRATNREELL 540
 541 AALRKGAELG RPFLIEVPVN YDFQPGGFGA LSIZ                             574
         |   10       |   20       |   30       |   40       |   50       |   60
```

FIGURE 10

```
            |   10      |   20      |   30      |   40      |   50      |   60
  1   MGAPVLPAAF GFLASARTGG GRAPGPVFAT RGSHTDIDTP QGERSLAATL VHAPSVAPDR  60
 61   AVARSLTGAP TTAVLAGEIY NRDELLSVLP AGPAPEGDAE LVLRLLERYD LHAFRLVNGR 120
121   FATVVRTGDR VLLATDHAGS VPLYTCVAPG EVRASTEAKA LAAHRDPKGF PLADARRVAG 180
181   LTGVYQVPAG AVMDIDLGSG TAVTHRTWTP GLSRRILPEG EAVAAVRAAL EKAVAQRVTP 240
241   GDTPLVVLSG GIDSSGVAAC AHRAAGELDT VSMGTDTSNE FREARAVVDH LRTRHREITI 300
301   PTTELLAQLP YAVWASESVD PDIIEYLLPL TALYRALDGP ERRILTGYGA DIPLGGMHRE 360
361   DRLPALDTVL AHDMATFDGL NEMSPVLSTL AGHWTTHPYW DREVLDLLVS LEAGLKRRHG 420
421   RDKWVLRAAM ADALPAETVN RPKLGVHEGS GTTSSFSRLL LDHGVAEDRV HEAKRQVVRE 480
481   LFDLTVGGGR HPSEVDTDDV VRSVADRTAR GAAZ                             514
            |   10      |   20      |   30      |   40      |   50      |   60
```

FIGURE 11

```
        |  10        |  20        |  30        |  40        |  50        |  60
  1 VERIDSHVSP RYAQIPTFMR LPHDPQPRGY DVVVIGAPYD GGTSYRPGAR FGPQAIRSES  60
 61 GLIHGVGIDR GPGTFDLINC VDAGDINLTP FDMNIAIDTA QSHLSGLLKA NAAFLMIGGD 120
121 HSLTVAALRA VAEQHGPLAV VHLDAHSDTN PAFYGGRYHH GTPFRHGIDE KLIDPAAMVQ 180
181 IGIRGHNPKP DSLDYARGHG VRVVTADEFG ELGVGGTADL IREKVGQRPV YVSVDIDVVD 240
241 PAFAPGTGTP APGGLLSREV LALLRCVGDL KPVGFDVMEV SPLYDHGGIT SILATEIGAE 300
301 LLYQYARAHR TQLZ                                                    314
        |  10        |  20        |  30        |  40        |  50        |  60
```

FIGURE 12

```
          |   10       |   20       |   30       |   40       |   50       |   60
  1 MASPIVDCTP YRDELLALAS ELPEVPRADL HGFLDEAKTL AARLPEGLAA ALDTFNAVGS  60
 61 EDGYLLLRGL PVDDSELPET PTSTPAPLDR KRLVMEAMLA LAGRRLGLHT GYQELRSGTV 120
121 YHDVYPSPGA HYLSSETSET LLEFHTEMAY HILQPNYVML ACSRADHENR AETLVGSVRK 180
181 ALPLLDEKTR ARLFDRKVPC CVDVAFRGGV DDPGAIANVK PLYGDANDPF LGYDRELLAP 240
241 EDPADKEAVA HLSQALDDVT VGVKLVPGDV LIIDNFRTTH ARTPFSPRWD GKDRWLHRVY 300
301 IRTDRNGQLS GGERAGDTIS FSPRRZ                                      326
          |   10       |   20       |   30       |   40       |   50       |   60
```

FIGURE 13

```
         |  10       |  20       |  30        |  40       |  50       |  60
  1  MSDSTPKTPR  GFVVHTAPVG  LADDGRDDFT  VLASTAPATV  SAVFTRSRFA  GPSVVLCREA  60
 61  VADGQARGVV  VLARNANVAT  GLEGEENARE  VREAVARALG  LPEGEMLIAS  TGVIGRQYPM  120
121  ESIREHLKTL  EWPAGEGGFD  RAARAIMTTD  TRPKEVRVSV  GGATLVGIAK  GVGMLEPDMA  180
181  TLLTFFATDA  RLDPAEQDRL  FRRVMDRTFN  AVSIDTDTST  SDTAVLFANG  LAGEVDAGEF  240
241  EEALHTAALA  LVKDIASDGE  GAAKLIEVQV  TGARDDAQAK  RVGKTVVNSP  LVKTAVHGCD  300
301  PNWGRVAMAI  GKCSDDTDID  QERVTIRFGE  VEVYPPKARG  DQADDALRAA  VAEHLRGDEV  360
361  VIGIDLAIAD  GAFTVYGCDL  TEGYVRLNSE  YTTZ                                394
         |  10       |  20       |  30        |  40       |  50       |  60
```

FIGURE 14

```
          |   10       |   20       |   30        |   40       |   50       |   60
    1 METTRSTTAD  EGFDAGVRGV  VAPTDAPGGT   LRLVRTDDFD  SLDPGNTYYA  YTWNFLRLIG  60
   61 RTLVTFDTAP  GKAGQRLVPD  LAESLGESSE   DGRVWTYRLR  EGLRYEDGTP  VVSADIKHAI 120
  121 ARSNYGTDVL  GAGPTYFRHL  LGTEYGGPWR   EPDADGPVTL  ETPDERTLVF  RLREPFAGMD 180
  181 LLATMPSTTP  VPRDRDTGAE  YRLRPVATGP   YRIVSYTRGE  LAVLEPNPHW  DPETDPVRVQ 240
  241 RASRIEVHLG  KDPHEVDRML  LAGEAHVDLA   GFGVQPAAQE  RILAEPELRA  HADNPLTGFT 300
  301 WIYCLSSRIA  PFDNVHCRRA  VQFATDKAAM   QEAYGGAVGG  DIATTLLPPT  LDGYKHFDRY 360
  361 PVGPEGTGDL  EAARAELKLA  GMPDGFRTRI   AARKDRLKEY  RAAEALAAGL  ARVGIEAEVL 420
  421 DFPSGDYFDR  YGGCPEYLRE  HGIGIIMFGW   GADFPDGYGF  LQQITDGRAI  KERGNQNMGE 480
  481 LDDPEINALL  DEGAQCADPA  RRAEIWHRID   QLTMDHAVIV  PYLYPRSLLY  RHPDTRNAFV 540
  541 TGSFGMYDYV  ALGAKZ                                                      556
          |   10       |   20       |   30        |   40       |   50       |   60
```

FIGURE 15

```
      |   10        |   20        |   30        |   40        |   50        |   60
  1 MEVARRTGVR HGTVERRLDR LDRIVGLPLT LRSRHTARLT TAGSRILVAG RRFFHQVDLA  60
 61 ARTHIFGHGS EAVDAPEVLS LVSTEPLLDE VVEDAAASLD LLLSVRHEAP HQVAAQLAGY 120
121 QVDAAYTWSL QSPRHSLERS VRTCEVLDDP LWVILPRDHP LAARREVSLA DLRDETWVSE 180
181 TGPGSEILVT RVFQLAGLTA PTRLHITGAS VARGILRRGD AIGLGSPTHP AVQDPSLVRR 240
241 SLAERPRRTT SLLVDPTIVP RALAGRLAAL IAEVQLRRFA EHHRDLLDEP WWAQWYAERT 300
301 GADARRFGAG PDQGSVPGQA EGRKLDVDDL HLLQAVARHG SINRAAAVLS ISQSALTRRI 360
361 HRLEQSLGAR LLLRSPRGTS LTGPTRQFLR QLALYEAEFR EAALACRSVE RPLAQGHWPI 420
421 RRGVAAGARM SGZ                                                    433
      |   10        |   20        |   30        |   40        |   50        |   60
```

FIGURE 16

```
        |   10       |   20       |   30       |   40       |   50       |   60
  1 MPSALQGKVA LITGASSGIG EATARALAAE GAAVAIAARR VEKLRALGDE LTAAGAKVHV  60
 61 LELDVADRQG VDAAVASTVE ALGGLDILVN NAGIMLLGPV EDADTTDWTR MIDTNLLGLM 120
121 YMTRAALPHL LRSKGTVVQM SSIAGRVNVR NAAVYQATKF GVNAFSETLR QEVTERGVRV 180
181 VVIEPGTTDT ELRGHITHTA TKEMYEQRIS QIRKLQAQDI AEAVRYAVTA PHHATVHEIF 240
241 IRPTDQVZ                                                           248
        |   10       |   20       |   30       |   40       |   50       |   60
```

FIGURE 17

```
          |   10       |   20       |   30       |   40       |   50       |   60
  1 MMNEAAPQSD QVAPAYPMHR VCPVDPPPQL AGLRSQKAAS RVTLWDGSQV WLVTSHAGAR  60
 61 AVLGDRRFTA VTSAPGFPML TRTSQLVRAN PESASFIRMD DPQHSRLRSM LTRDFLARRA 120
121 EALRPAVREL LDEILGGLVK GERPVDLVAG LTIPVPSRVI TLLFGAGDDR REFIEDRSAV 180
181 LIDRGYTPEQ VAKARDELDG YLRELVEERI ENPGTDLISR LVIDQVRPGH LRVEEMVPMC 240
241 RLLLVAGHGT TTSQASLSLL SLLTDPELAG RLTEDPALLP KAVEELLRFH SIVQNGLARA 300
301 AVEDVQLDDV LIRAGEGVVL SLSAGNRDET VFPDPDRVDV DRDARRHLAF GHGMHQCLGQ 360
361 WLARVELEEI LAAVLRWMPG ARLAVPFEEL DFRHEVSSYG LGALPVTWZ             409
          |   10       |   20       |   30       |   40       |   50       |   60
```

FIGURE 18

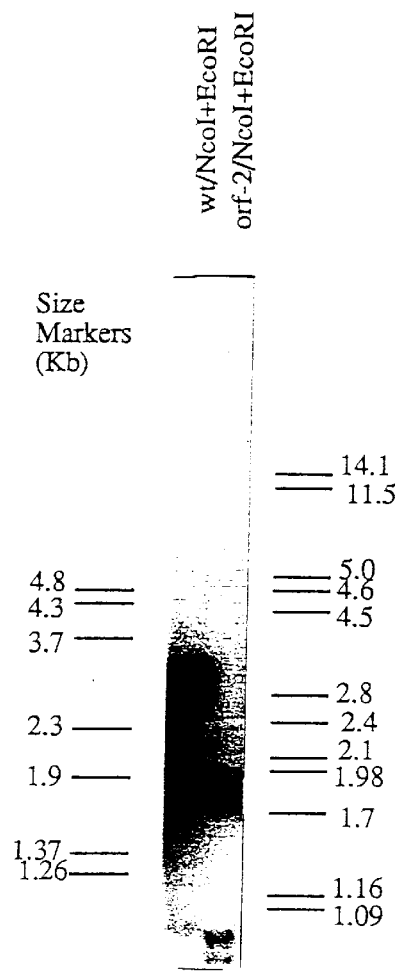
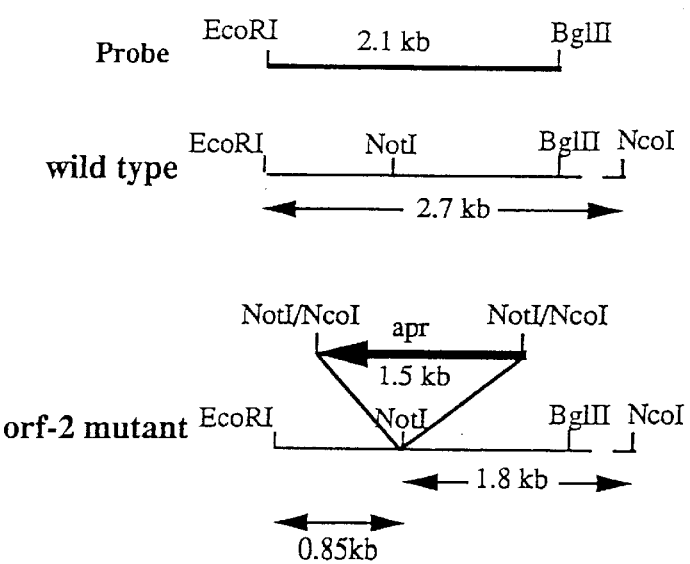
FIGURE 19

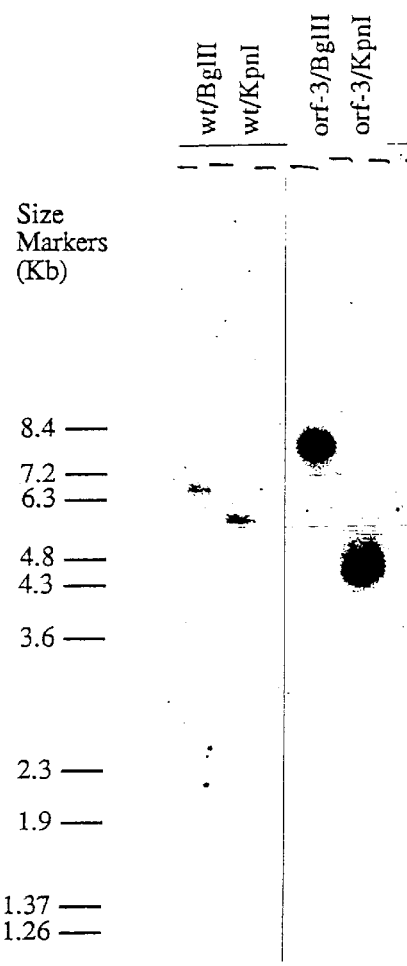
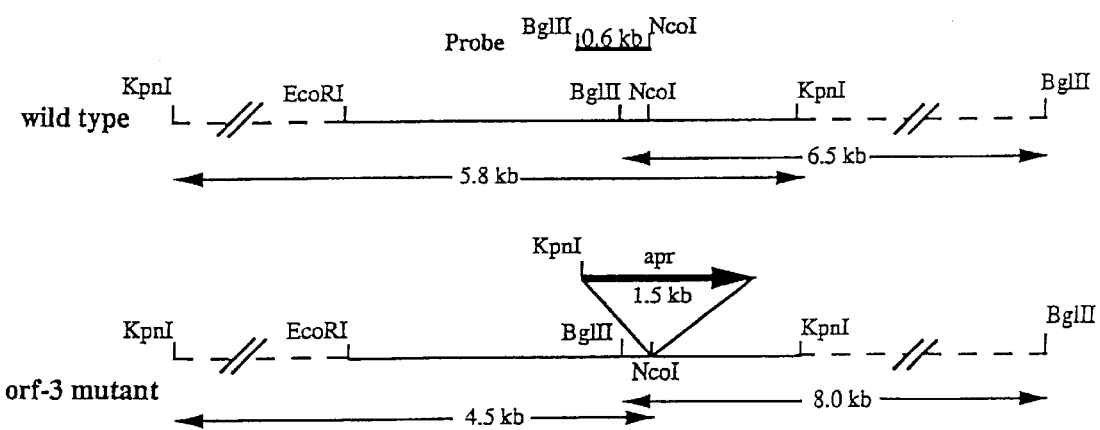
FIGURE 20

DNA SEQUENCE ENCODING ENZYMES OF CLAVULANIC ACID BIOSYNTHESIS

This is a divisional application of application Ser. No. 08/790,462, filed Jan. 29, 1997, now abandoned, which is a continuation-in-part of application Ser. No. 08/567,801, filed Dec. 6, 1995, now abandoned, which is a continuation of application Ser. No. 08/134,018, filed Oct. 8, 1993, now abandoned.

This invention relates to methods for the production of the antibiotic, clavulanic acid.

BACKGROUND OF THE INVENTION

Clavulanic acid is a broad spectrum beta-lactamase inhibitor and is an important antibiotic for the treatment of infectious diseases. It is produced commercially by the gram-positive mycelial prokaryote *Streptomyces clavuligerus*, which also produces the β-lactam antibiotics penicillin N, desacetoxy cephalosphorin C and cephamycin C. Until recently, however, the pathway employed for clavulanic acid biosynthesis was much less well understood than the pathways leading to these other antibiotics.

Without knowledge of the pathway for clavulanic acid biosynthesis, it was not possible to isolate the genes coding for the key enzymes and to manipulate these genes to increase antibiotic yield or permit production of the antibiotic in heterologous systems.

One of the earliest enzymes of the pathway to be purified and characterised was clavaminic acid synthase. Two isozymes have now been identified and characterised (Marsh et al., (1992), Biochem., vol. 31, pp. 12648–657).

European Patent Application 0349121 describes a 6.8 kb Bgl II restriction fragment isolated from *S. clavuligerus* that encodes a portion of the genetic information involved in clavulanic acid synthesis. No further characterization of this fragment was performed nor was the utility of this fragment determined.

Marsh et al (1992, Biochem. vol 31, pp. 12648–657) cloned and sequenced two isozymes of clavaminate synthase cs1 and cs2 separated by 28 kb, however their location relative to the cephamycin and penicillin biosynthetic clusters was not determined. Ward and Hodgson (1993, FEMS Microbiol. Lett. vol 110, pp. 239–242) reported on the occurrence of a biosynthetic gene cluster for clavulanic acid. Aidoo et al (1994, Gene vol 147, pp. 4146) cloned and sequenced cla the gene encoding a protein (possibly proclavaminic acid amidinohydrolase) involved in clavulanic acid production. They reported that this gene was upstream from and adjacent to an ORF with the identical sequence of cs2. Paradkar and Jensen (1995, J Bacteriol, vol 177, pp. 1307–1314) further analyzed a 6.6 kb Bgl II fragment from *S. clavuligerus* comprising cs2 and through gene disruption experiments demonstrated its role in clavulanic acid synthesis.

Until the work of the present inventors, the complete complement of genes required for clavulanic acid synthesis had not been identified.

The present inventors have now isolated, cloned and sequenced a 15 kb DNA fragment from *S. clavuligerus* which encodes 10 ORFs. Within this 15 kb of DNA lies an 11.6 kb EcoRI fragment which codes for eight proteins and enables the production of clavulanic acid by transformants of non-clavulanic-producing organisms. This 11.6 kb fragment includes 8 complete ORFs (ORFs 2 to 9), two of which have been previously characterized (Marsh et al 1992, Paradkar and Jensen 1995). ORF1, which is incomplete, is not involved in clavulanic acid synthesis, ORF4 encodes the CLA protein and ORF5 is cs2, encoding one of the isozymes of clavaminate synthase. The function of the other remaining ORFs within this 11.6 kb fragment or their role in clavulanic acid synthesis is unknown.

SUMMARY OF THE INVENTION

An isolated genomic DNA molecule of 15 kb is provided comprising the nucleotide sequence set out in FIG. 2. This DNA molecule comprises 10 ORFs, eight of which are involved in clavulanic acid synthesis. A process is provided for producing clavulanic acid in a transformant of a non-clavulanate-producing host.

The present invention provides isolated DNA molecules having the nucleotide sequence of SEQ ID NOS: 15, 16, 19, 20, 21 and 22.

Furthermore, the present invention is directed to DNA molecules comprising the nucleotide sequences that encode the amino acid sequence found in FIGS. 11, 12, 15, 16, 17 and 18 which corresponds to SEQ IN NOS: 4, 5, 8, 9, 10 and 11.

This invention also embraces DNA molecules comprising the nucleotide sequences encoding the amino acid sequences of FIGS. 11, 12, 15, 16, 17 and 18. These amino acid sequences correspond to the expression products of ORFs 2, 3, 6, 7, 8 and 9.

This invention is directed to isolated proteins having the amino acid sequence of FIGS. 11, 12, 15, 16, 17 and 18. These amino acid sequences correspond to the expression products of the ORFs 2, 3, 6, 7, 8 and 9 as defined in SEQ ID NOS: 4, 5, 8, 9, 10 and 11.

This invention is also directed to recombinant vectors that comprise DNA molecules as defined above where hosts that have been transformed with these recombinant vectors.

This invention is also directed to the process for producing clavulanic acid in a non-clavulantic acid producing host that comprises transforming the host with a DNA molecule as defined above and culturing the host under suitable conditions to produce clavulanic acid.

Furthermore, this invention is directed to processes for enhancing clavulanic acid production in a clavulanic acid producing host comprising transforming the host with a DNA molecule as defined above.

DESCRIPTION OF DRAWINGS

The invention, as exemplified by a preferred embodiment, is described with reference to the accompanying drawings in which:

FIG. 1 shows the N terminal amino acid sequence of CLA (amino acid residues 1–25 of SEQ ID NO: 6), the potential codon corresponding with this sequence (SEQ ID NO: 24), and the nucleotide sequence of a probe (SEQ ID NO: 25) directed to the underlined region of the sequence. The nucleotide sequence of the actual DNA sequence is defined in SEQ ID NO: 1, specifically nucleotides 5687–5710 of SEQ ID NO: 1, 3665–3678 of SEQ ID NO: 13, or 34–57 of SEQ ID NO: 17.

FIG. 2 (2-1 to 2-10) shows the nucleotide sequence (Sequence ID No.:1) of a 15 kb genomnic DNA fragment from *S. clavuligerus*. The sequences of the ten ORFs within the fragment are shown in upper case letters and the intergenic regions are shown in lower case letters. The locations of the beginning and end of each ORF are also indicated directly above the nucleotide sequence. Asterisks above the sequence indicate the EcoRl sites which mark the beginning and end of the portion of the DNA sequence which contains all the genetic information for clavulanic acid synthesis.

FIG. 9 shows the deduced amino acid sequence (Sequence ID No.:3) of ORF1 of FIG. 2.

FIG. 10 shows the deduced amino acid sequence (Sequence ID No.:4) of ORF2 of FIG. 2.

FIG. 11 shows the deduced amino acid sequence (Sequence ID No.:5) of ORF3 of FIG. 2.

FIG. 12 shows the deduced amino acid sequence (Sequence ID No.:6) of ORF4 of FIG. 2.

FIG. 13 shows the deduced amino acid sequence (Sequence ID No.:7) of ORF5 of FIG. 2.

FIG. 14 shows the deduced amino acid sequence (Sequence ID No.:8) of ORF6 of FIG. 2.

FIG. 15 shows the deduced amino acid sequence (Sequence ID No.:9) of ORF7 of FIG. 2.

FIG. 16 shows the deduced amino acid sequence (Sequence ID No.:10) of ORF8 of FIG. 2.

FIG. 17 shows the deduced amino acid sequence (Sequence ID No.:11) of ORF9 of FIG. 2.

FIG. 18 shows the deduced amino acid sequence (Sequence ID No.:12) of ORF10 of FIG. 2.

FIGS. 19 to 23. The upper panel shows the results of Southern hybridizations using the probes and gene fragments as set forth in the restriction maps of the lower panel.

FIG. 19 shows the construction of the orf-2 mutant.

FIG. 20 shows the construction of the orf-3 mutant.

FIG. 21 shows the construction of the orf-6 mutant.

FIG. 22 shows the construction of the orf-8 mutant.

FIG. 23 shows the construction of the orf-9 mutant.

DETAILED DESCRIPTION OF THE INVENTION

Figure 3:
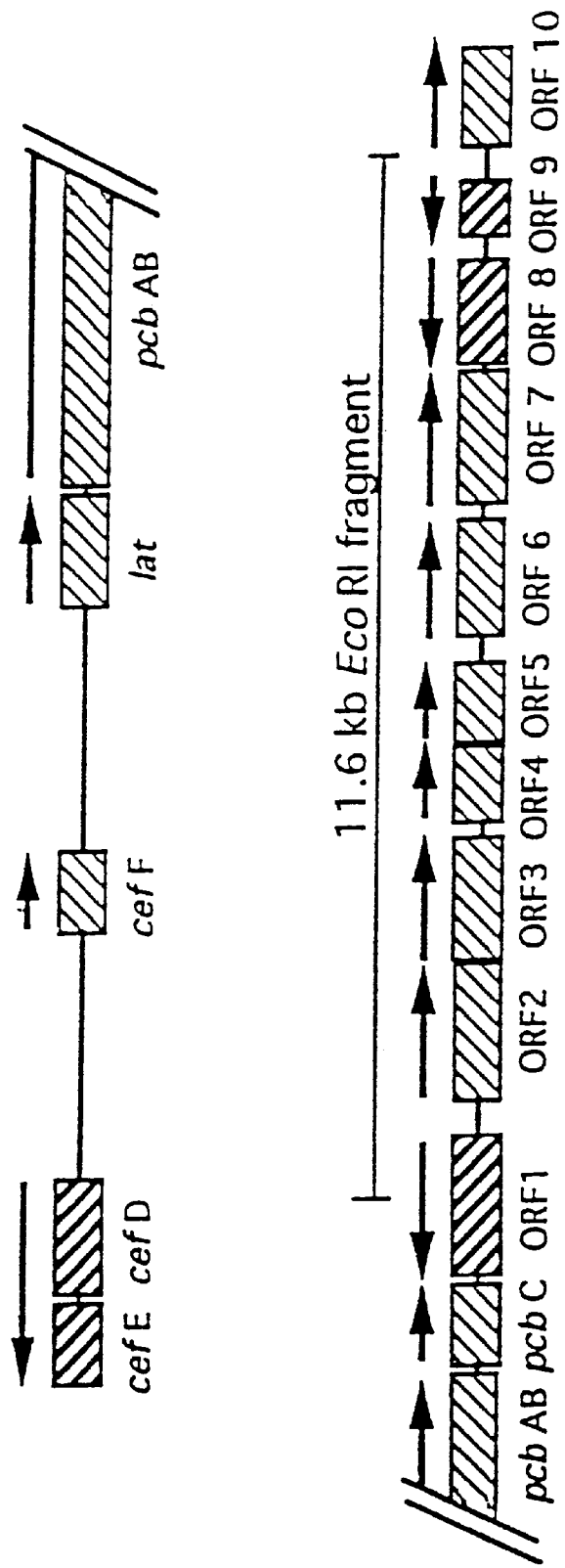
FIG. 3 shows the location of the open reading frames downstream from pcbC.
Figure 4:
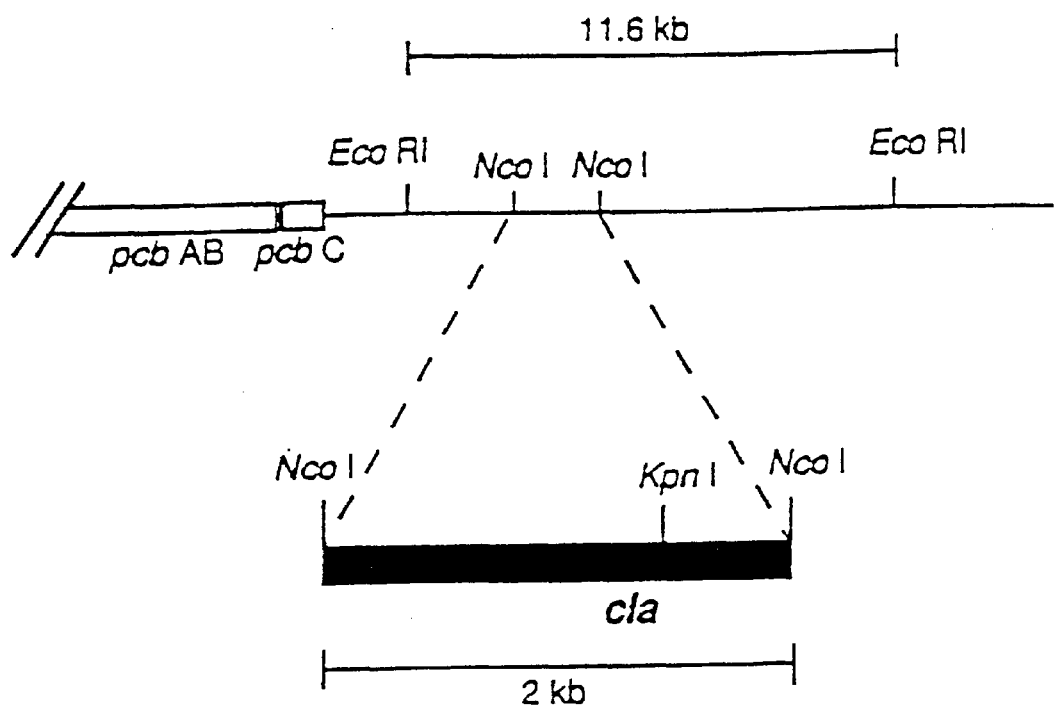
FIG. 4 shows a partial restriction map of the DNA sequence of FIG. 2 in the region surrounding cla (ORF4).
Figure 5:
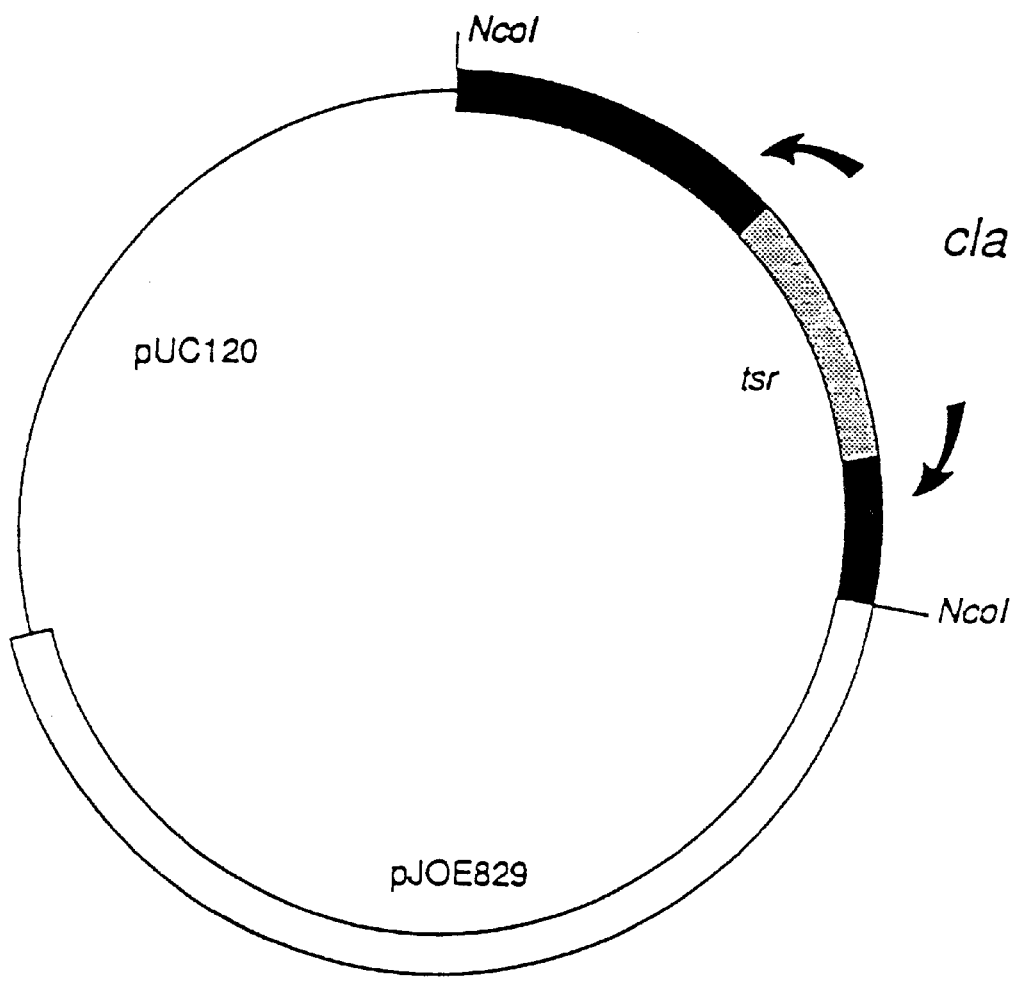
FIG. 5 shows a shuttle vector used for disruption of the cla gene.

Production of penicillin and cephamycin antibiotics in S. clavuligerus starts with the conversion of lysine to α-aminoadipic acid (Madduri et al., (1989), J. Bacteriol., v. 171, pp. 299–302; (1991), J. Bacteriol., v. 173, pp. 985–988). α-Aminoadipic acid then condenses with cysteine and valine to give δ-(L-α-aminoadipyl)-L cysteinyl-D-valine (ACV) by the action of aminoadipyl cysteinyl-valine synthetase (ACVS). ACV is converted by isopenicillin N synthase (IPNS) to isopenicillin N, and, through a series of reactions, to desacetoxycephalosporin C and ultimately to cephamycin C (Jensen et al., (1984), Appl. Microbiol. Biotechnol., v. 20, pp 155–160).

The ACVS of S. clavuligerus has been purified and partially characterized by three separate groups, and estimates of its molecular weight vary from 350,000 to 500,000 Da (Jensen et al., (1990) J. Bacteriol., v. 172, pp. 7269–7271; Schwecke et al., (1992), Eur. J. Biochem., v. 205, pp. 687–694; Zhang and Demain, (1990), Biotech Lett., v. 12, pp. 649–654). During their purification, Jensen et al. observed a 32,000 Da protein which co-purified with ACVS despite procedures which should remove small molecular weight components. It has now been found that this protein is not related to ACVS but rather to clavulanic acid biosynthesis. It has been designated CLA .

In accordance with one embodiment of the invention, the present inventors have identified, cloned and sequenced the gene (cla) encoding this protein.

In accordance with a further embodiment of the invention, the inventors have cloned and sequenced a 15 kb stretch of genomic DNA from S. clavuligerus which includes the cla gene. Within this 15 kb sequence, the inventors have identified an 11.6 kb DNA fragment which, when introduced into the non-clavulanate producer S. lividans as described in Example 4, enabled that species to produce clavulanic acid. This indicates that the 11.6 kb fragment contains all the genetic information required for clavulanate production.

As will be understood by those skilled in the art, the identification of the DNA sequence encoding the enzymes required for clavulanate synthesis will permit genetic manipulations to modify or enhance clavulanate production. For example, clavulanate production by S. clavuligerus may be modified by introduction of extra copies of the gene or genes for rate limiting enzymes or by alteration of the regulatory components controlling expression of the genes for the clavulanate pathway.

Heterologous organisms which do not normally produce clavulanate may also be enabled to produce clavulanate by introduction, for example, of the 11.6 kb DNA sequence of the invention by techniques which are well known in the art, as exemplified herein by the production of S. lividans strains capable of clavulanate synthesis. Such heterologous production of clavulanic acid provides a means of producing clavulanic acid free of other contaminating clavams which are produced by S. clavuligerus.

Suitable vectors and hosts will be known to those skilled in the art; suitable vectors include pIJ702, pJOE829 and pIJ922 and suitable hosts include S. lividans, S. parvulus, S. griseofulvus, S. antibioticus and S. lipmanii.

Additionally, the DNA sequences of the invention enable the production of one or more of the enzymes of the clavulanate pathway by expression of the relevant gene or genes in a heterologous expression system.

The DNA sequences coding for one or more of the pathway enzymes may be introduced into suitable vectors and hosts by conventional techniques known to those skilled in the art. Suitable vectors include pUC118/119 and pET-11 and suitable hosts include many organisms, including *E. coli* strains such as MV1193 and BL21(DE3).

An oligonucleotide probe (SEQ ID NO: 25) based on the N-terminal amino acid sequence of CLA (amino acid residues 1–25 of SEQ ID NO: 6); was constructed as shown in FIG. 1 and was used to isolate the gene coding for the protein from *S. clavuligerus*, as described in Example 1.

The gene was found to be located in the *S. clavuligerus* chromosome about 5.7 kb downstream of pcbC, the gene which encodes isopenicillin N synthase. The gene contains a 933 bp open reading frame (ORF), encoding a protein of molecular weight 33,368. The deduced amino acid sequence was compared to database sequences and showed greatest similarity to enzymes associated with arginine metabolism, notably agmatine, ureohydrolase and arginases.

When an internal fragment of the cla gene was labelled and used to probe restriction endonuclease digests of genomic DNA from a variety of other Streptomyces and related species, evidence of homologous sequences was seen only in other clavulanic acid or clavam metabolite producers, including *Streptomyces jumonjinensis, Streptomyces lipmanii* and *Streptomyces antibioticus*. No cross reactivity was seen to the β-lactam producing species *Nocardia lactamdurans, Streptomyces griseus* or *Streptomyces cattleya*, nor to any of a variety of other Streptomyces species which do not produce β-lactam compounds, including *S. fradiae* ATCC 19609, *S. venezuelae* 13s and *S. griseofulvus* NRRL B-5429.

Disruption of the cla gene, as described in Example 3, led to loss of the ability to synthesise clavulanic acid.

A 15 kb DNA sequence extending downstream from pcbC was cloned and sequenced as described in Example 5. The nucleotide sequence is shown in FIG. 2. When this SEQ ID No.: 1 sequence information was analysed for percent G+C as a function of codon position (Bibb et al., (1984), Gene, v. 30, pp. 157–166), ten complete ORFs were evident, as shown in FIG. 3. ORF 4 corresponds to cla. ORF 1, 7 & 8 are oriented in the opposite direction to pcbC. ORFs 2–6 and ORF 10 are all oriented in the same direction as pcbC. ORFs 2 and 3, and ORFs 4 and 5 are separated by very short intergenic regions suggesting the possibility of transcriptional and translational coupling. Table 1 summarises the nucleotide sequences and lengths of ORFs 1–10.

TABLE 1

| ORF# | Start Location (bp) | End Location (bp) | Length (bp) | Size of ORF (aa residues) | SEQ ID NO. |
|---|---|---|---|---|---|
| 1* | 1764 | 109 | 1656 | 552 | 14 |
| 2 | 2216 | 3937 | 1722 | 574 | 15 |
| 3 | 3940 | 5481 | 1542 | 514 | 16 |
| 4 | 5654 | 6595 | 942 | 314 | 17 |
| 5 | 6611 | 7588 | 978 | 326 | 18 |
| 6 | 7895 | 9076 | 1182 | 394 | 19 |
| 7 | 9241 | 10908 | 1668 | 556 | 20 |
| 8* | 12296 | 10998 | 1299 | 433 | 21 |
| 9 | 13365 | 12622 | 744 | 248 | 22 |
| 10 | 13769 | 14995 | 1227 | 409 | 23 |

*ORFs which are oriented in the opposition direction.

When the predicted amino acid sequences of proteins encoded by ORFs 1–10 were compared to protein sequence databases, some similarities were noted in addition to the already mentioned similarity between CLA and enzymes of arginine metabolism. ORF 1 (SEQ ID No.: 14) showed a low level of similarity to penicillin binding proteins from several different microorganisms which are notable for their resistance to β-lactam compounds.

An EcoRI fragment of the 15 kb DNA sequence, containing 11.6 kb DNA, was cloned into a high copy number shuttle vector and introduced into *S. lividans*, as described in Example 4. Of seventeen transformants examined, two were able to produce clavulanic acid, indicating that the 11.6 kb fragment contains all the necessary genetic information for clavulanic acid production.

This 11.6 kb fragment encompasses ORF 2 to ORF 9 of the 15 kb DNA sequence.

ORF 2 (SEQ ID No.: 15) shows a high degree of similarity to acetohydroxyacid synthase (AHAS) enzymes from various sources. AHAS catalyses an essential step in the biosynthesis of branched chain amino acids. Since valine is a precursor of penicillin and cephamycin antibiotics, and valine production is often subject to feedback regulation, it is possible that a deregulated form of AHAS is produced to provide valine during the antibiotic production phase. Alternatively, an AHAS-like activity may be involved in clavulanic acid production. While the presently recognized intermediates in the clavulanic acid biosynthetic pathway do not indicate a role for AHAS, the final step in the biosynthetic pathway, conversion of clavaminic acid to clavulanic acid, requires NADPH, and either pyruvate or α-ketobutyrate as well as other cofactors (Elson et al., (1987), J. Chem. Soc. Chem. Commun., pp. 1739–1740). It is striking that these same substrates and cofactors are required for AHAS activity. Perhaps the conversion of clavaminate to clavulanate actually involves several steps, one of which is catalyzed by an AHAS-like activity. ORFs 3 (SEQ ID No.: 16) and does not show a significant similarity to any proteins in the data bases. ORF 6 (SEQ ID No.: 19) shows similarity to ornithine acetyltransferase. Ornithine has been suggested to be the immediate precursor of a 5-C fragment of the clavulanic acid skeleton, but the details of the reaction required for the incorporation of ornithine are unknown. ORF 7 (SEQ ID No.: 20) shows weak similarity to protein XP55 from *S. lividans*, and a lower level of similarity to oligopeptide binding proteins from various other species. Similarly, ORF 8 (SEQ ID No. 21) shows weak similarity to several transcription activator proteins, and ORF 9 (SEQ ID No.: 22) shows weak similarity to ribitol 5 $PO_4$ dehydrogenase-type enzymes. ORF 10 (SEQ ID NO: 23) shows a high similarity to cytochrome P450 type enzymes from other Strepomyces species.

ORF5 has now been identified as the gene for clavaminate synthase II (Marsh (1993) supra).

Figure 6:
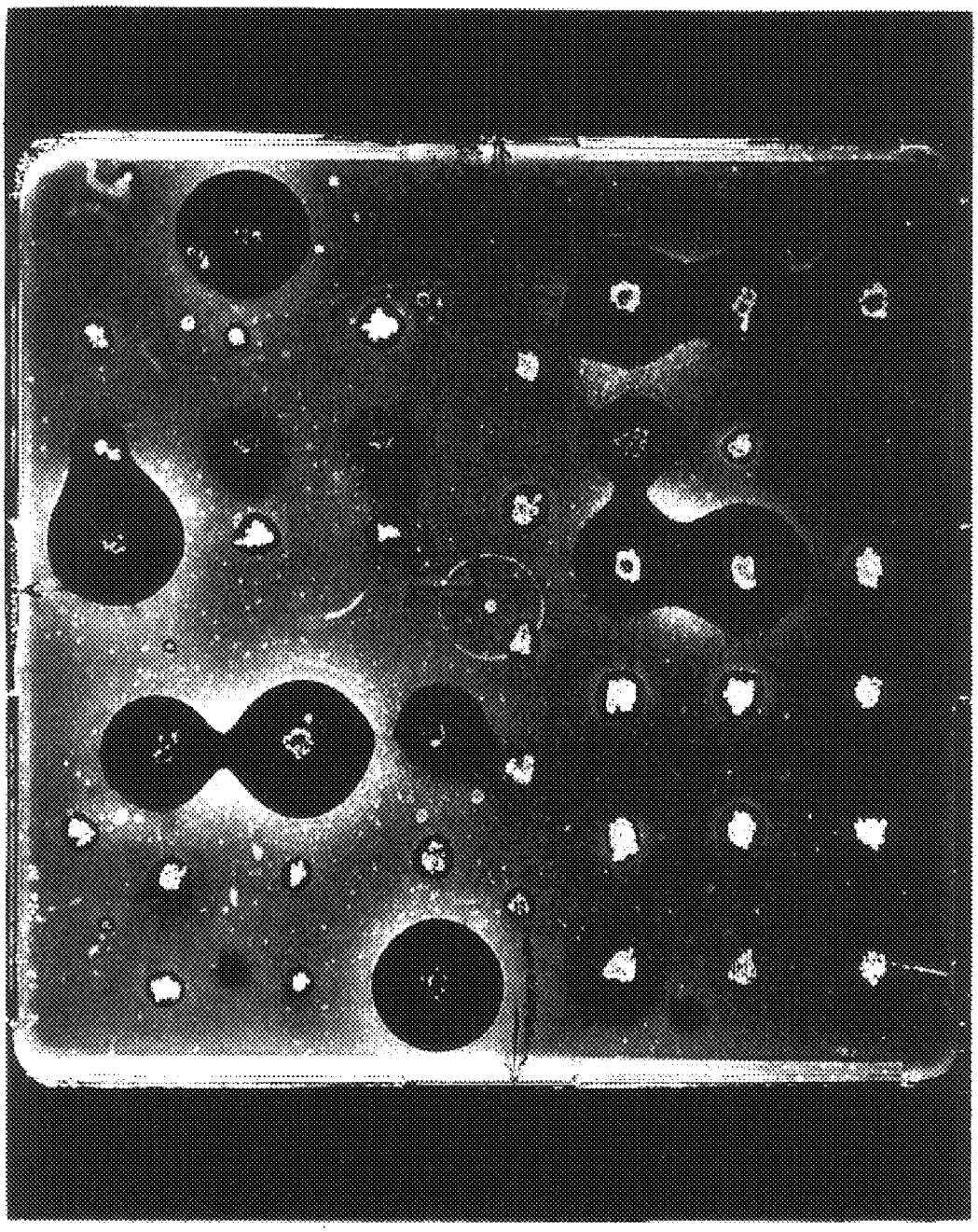
FIG. 6 shows a photograph of an agar plate bearing cultures of S. lividans transformants.

When a plasmid isolated from one of the two clavulanic acid-producing transformants was retransformed into *S. lividans*, about 40–45% of the resulting colonies were able to produce clavulanic acid, as shown in FIG. 6.

EXAMPLES

Example 1

Bacterial Strains, Vectors and Growth Conditions.

*Streptomyces clavuligerus* NRRL 3585, *Stretomyces jumonjinenisis* NRRL 5741, *Streptomyces lipmanii* NRRL 3584, *Streptomyces griseus* NRRL 3851, *Nocardia lactamdurans* NRRL 3802 and *Streptomyces cattleya* NRRL 3841 were provided by the Northern Regional Research Laboratories, Peoria, Ill. *Streptomyces antibioticus* ATCC 8663 and *Streptomyces fradiae* ATCC 19609 were obtained from the American Type Culture Collection, Manassas, Va. *Streptomyces lividans* strains 1326 and TK24 were provided by D. A. Hopwood (John lnnes Institute, Norwich, U.K.), *Streptomyces venezuelae* 13s and *Streptomyces griseofuscus* NRRL B-5429 were obtained from L. C. Vining (Department of Biology, Dalhousie University, Halifax, N.S.). Cultures were maintained on either MYM (Stuttard (1982) J. Gen. Microbiol., v. 128, pp. 115–121) or on a modified R5 medium (Hopwood et al. (1985) in "Genetic Manipulation of Streptomyces: a laboratory manual", John Innes Foundation, U.K.) containing maltose instead of glucose and lacking sucrose (R5-S). *Escherichia coli* MV1193 (Zoller and Smith (1987) Methods in Enzymology, v. 154, pp. 329–349), used as recipient for all of the cloning and subcloning experiments, was grown in Luria Broth (LB; Sambrook et al. (1989) in "Molecular Cloning: a laboratory manual", Cold Spring Harbour, N.Y.) or on LB agar (1.5%) plates containing ampicillin (50 µg/mL) or tetracycline (10 µg/mL). The cloning vectors pUC118 and pUC119 (Vieira and Messing (1987) Methods in Enzymology, v. 153, pp. 3–11) were provided by J. Vieira (Waksman Institute of Microbiology, Rutgers University, Piscataway, N.J.). The plasmid vector pJOE829 was generously provided by J. Altenbuchner (University of Stuttgart, Stuttgart, Germany). The plasmid pIJ702 was obtained from the American Type Culture Collection, Manassas, Va. Restriction enzymes were purchased from Boehringer Mannheim, and used according to the manufacturers' specifications.

Separation of CLA from ACVS

CLA was previously characterized as a 32,000 Da molecular weight protein present in preparations of highly purified ACVS (Jensen et al. (1990), supra). The small size of CLA suggested that its co-purification with ACVS resulted from a physical association between the two proteins.

ACVS and CLA were resolved by applying a 0.2 ml sample of purified ACVS containing CLA onto a Superose 6 HR 10/30 (Pharmacia), which was equilibrated and eluted in 0.1 M MOPS buffer, pH 7.5 containing 0.05 M KCl, 1 mM dithiothreitol, and 20% glycerol, at a flow rate of 0.25 ml/min.

Comparison of the CLA retention time with those of molecular weight standards indicated that the native molecular weight of CLA was in excess of 270 kDa. The difference in molecular weight between native and denatured forms of CLA suggests that the native protein exists as an oligomer of eight identical subunits.

Isolation of Gene (cla) for CLA

N-terminal amino acid sequence information for CLA was obtained by electrophoretically transferring the protein from SDS polyacrylamide gels onto Immobilon membranes (Millipore Ltd.,) and submitting the material to the Protein Microsequencing Laboratory (University of Victoria,) for analysis. Information obtained for 25 amino acids at the N-terminus (amino acid residues 1–25 of SEQ ID NO: 6) was used to prepare a 24 mer oligonucleotide probe (SEQ ID NO: 25) with 8-fold degeneracy to the amino acid sequence underlined in FIG. 1. The amino acids in brackets indicate ambiguities in the N terminal sequence. The actual DNA sequence from the cloned fragment is indicated in FIG. 2 and SEQ ID No: 1.

The probe was designed as an 8-fold degenerate mixture of oligonucleotides to take into consideration the biased codon usage of streptomyces Wright and Bibb (1992), Gene, v. 113, pp. 55–65).). End-labelled probe was then used to screen a cosmid library of *S. clavuligerus* genomic DNA fragments.

A library of *S. clavuligerus* genomic DNA fragments (15–22 kb size fractionated fragments) was constructed as previously described (Doran et al. (1990), J. Bacteriol, v. 172, pp. 4909–4918). Using the cosmid vector pLAFR3. A collection of 1084 isolated *E. coli* colonies contained recombinant cosmids was screened for the presence of cla using the 24-mer mixed oligonucleotide probe (FIG. 1) which had been end-labelled with [$\gamma$-$^{32}$P]dATP and polynucleotide kinase (Boehringer Mannheim). Colony hybridization and subsequent washing was performed as described by Sambrook et al., (1989), at 55° C. with a final wash in 0.2×SSC (I×SSC, 0.15M NaCl and 0.015M sodium citrate) and 0.1% SDS.

Five colonies which gave strong hybridization signals were isolated from the panel of 1084 clones, and restriction analysis showed that the positive clones contained overlapping fragments of DNA. Two clones, K6L2 and K8L2, with sequences that spanned about 40 kb of the *S. clavuligerus* genome, were chosen for further analysis. Clone K8L2 contained about 22 kb of *S. clavuligerus* genomic DNA and included a portion of cla and all of the pcbC gene which encodes IPNS in the penicillin/cephamycin biosynthetic pathway. A restriction map of K6L2 is shown in FIG. 9. Within the approximately 27 kb of DNA contained in K6L2, the oligonucleotide probe hybridized to a 2.0 kb NcoI fragment which was subsequently found to contain the entire cla gene. Hybridization studies, restriction mapping and DNA sequence analysis revealed that cla was situated 5.67 kb downstream of the pcbC gene of *S. clavuligerus* (FIG. 9).

DNA Sequencing and Analysis

Ordered sets of deletions were generated (Henikoff, 1984) extending across the cla region of the 2.0 kb NcoI fragment (FIG. 9C). The deletion generated fragments were sequenced in both orientations by the dideoxynucleotide chain termination method of (Sanger et al. (1977), P.N.A.S., v. 74, pp. 5463–5467) using Sequenase (version 2.0) DNA polymerase (United States Biochemical Corporation). Areas of compression in the sequence band pattern were relieved by carrying out reactions using 7-deaza-dGTP in place of dGTP. The nested deletion fragments resided either in pUC118 or pUC119, and were sequenced using the commercially available universal primers.

The nucleotide sequence data were analyzed for the presence of restriction sites, open reading frames (ORFs) and codon usage by the PC-Gene programme (Intelligenetics Corp.). Similarly searches were accomplished with the FASTA program searching the GenPept database (release number 71) available through GenBank (Pearson and Lipman (1988), P.N.A.S., v. 85, pp. 2444–2448).

Figure 7:
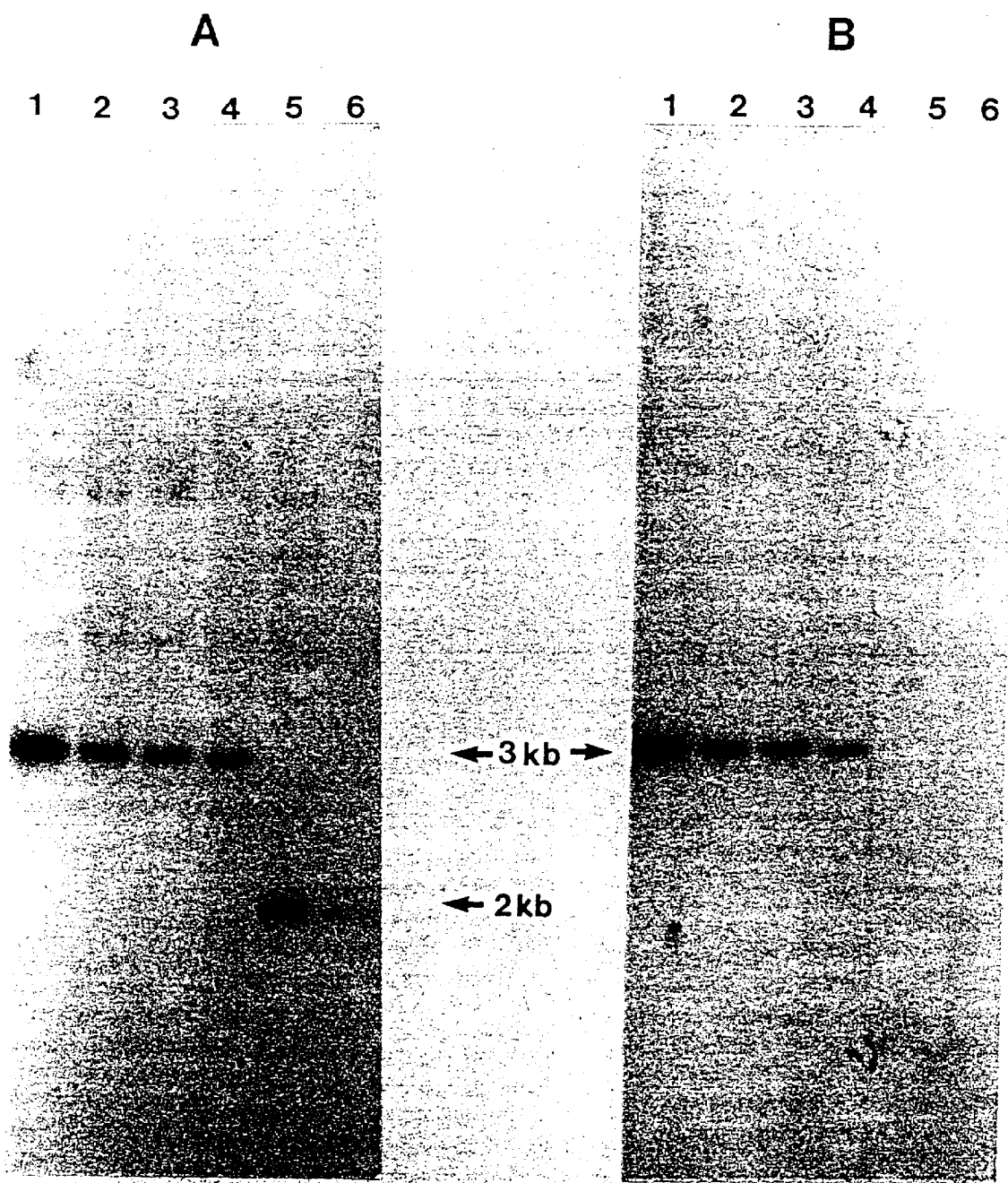
FIG. 7 shows a Southern blot of NcoI digests of genomic DNA from five presumptive mutants (lanes 1–5) and from wild-type S. clavuligerus (lane 6). Panel A: membranes probed with cla-specific probe. Panel B: membranes probed with tsr-specific probe.
Figure 8:
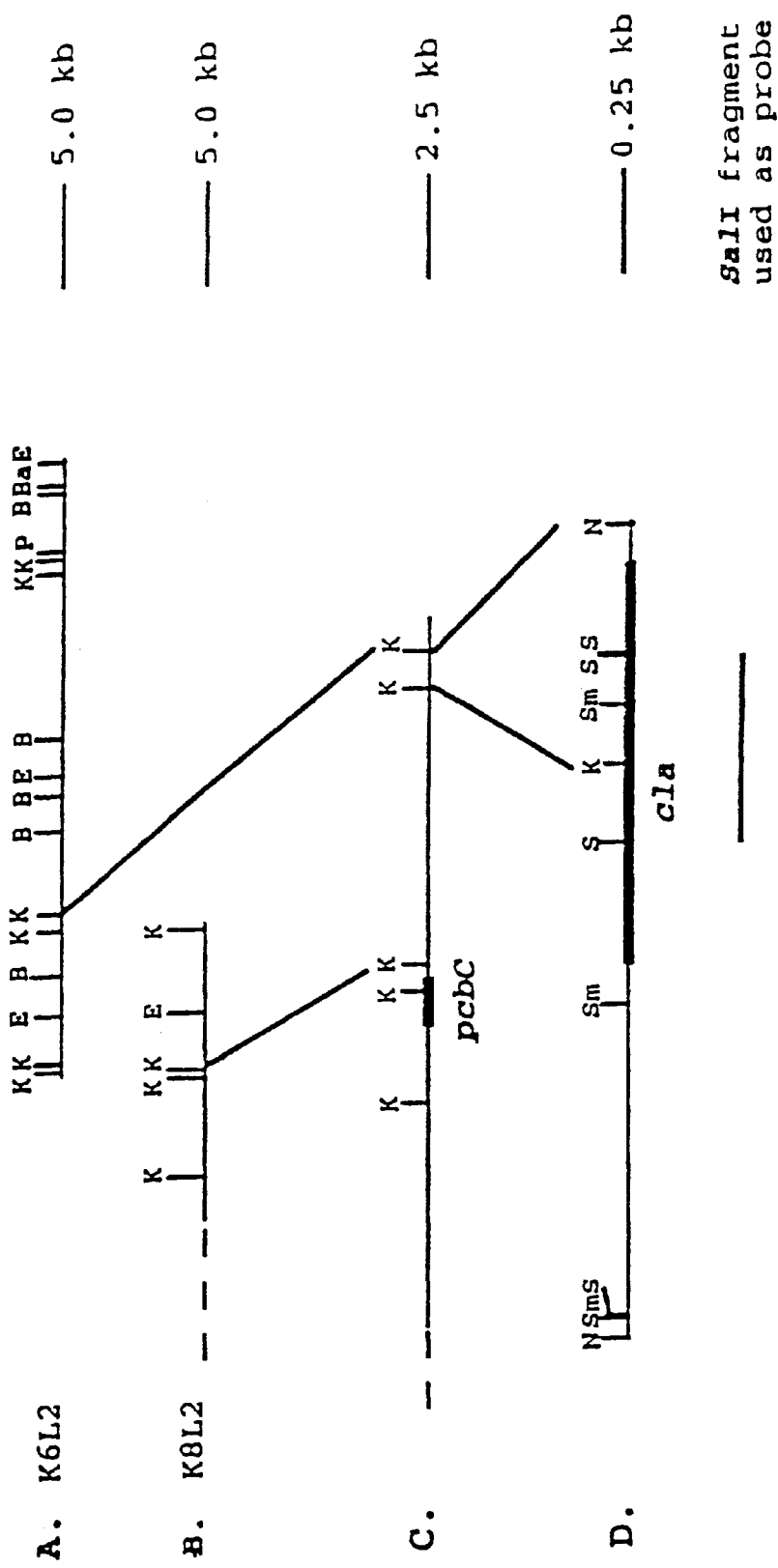
FIG. 8 shows restriction enzyme maps of S. clavuligerus DNA inserts in cosmids. A. Restriction enzyme map of cosmid K6L2. B. Partial restriction enzyme map of cosmid K8L2. C. Restriction map of cosmids K6L2 and K8L2 indicating location of pcbC gene in relation to cla. D. The 2.0 kb NcoI fragment encompassing the cla gene used in generating nested deletions for sequencing. Abbreviations: Ba, BamHI; B,BGlII; E,EcoR1; K,KpnI; N, NcoI; S,SalI; and Sm,SmaI.

An ORF at 939 bp with a potential ribosome site 9 bp from the GTG start codon was found which encoded a putative protein with a molecular weight of 33,368 Da. This value is in close agreement to the molecular weight estimated for CLA by SDS-PAGE (Jensen et al., 1990). The analysis of percent G+C as a function of codon position (FRAME analysis), using the algorithm of Bibb et al., (1984), indicated the presence of a typical streptomycete ORF (data not shown) with a G+C content of 70%. Computer aided data base searches for sequences similar to cla revealed a high degree of similarity to agmatine ureohydrolase (40.5% identity over 291 amino acids) and somewhat lower similarity to arginases (29.6% identity over 135 amino acids to arginases from yeast and rat) as shown in FIG. 7. The *S. clavuligerus* CLA sequence was aligned with the *E. coli* AUH sequence by the FASTA program described above. The AUH sequence had previously been aligned with the three ARG sequences (Szumanski & Boyle (1990), J. Bacteriol., v. 172, pp. 538–547). Identical matches in two or more sequences are indicated with upper case letters.

Example 2

DNA Hybridization

Genomic DNA preparations from various Streptomyces species were isolated as described by Hopwood et al. (1985). For interspecies DNA hybridization analysis, 2.0 µg amounts of genomic DNA preparations were digested with NcoI for 16 h, and electrophoresed in 1.0% agarose gels. The separated DNA fragments were then transferred onto nylon membranes (Hybond-N, Amersham) and hybridized with a cla specific probe prepared by labelling an internal 459 bp SalI fragment (FIG. 1) with $[\alpha^{32}P]DAPT$ by nick translation. Hybridization was done as decribed by Sambrook et al., (1989). Hybridization membranes were washed twice for 30 min in 2×SSC; 0.1% SDS and once for 30 min in 0.1×SSC; 0.1% SDS at 65° C.

Sequences Homologous to cla in Other Streptomycetes

Three of six producers of β-lactam antibiotics, S. clavuligerus, S. lipmanii and S. jumonjinesis showed positive hybridization signals whereas S. cattleya, S. griseus, and N. lactamdurans did not (data not shown). None of the nonproducing strains examined, S. venezuelae, S. lividans, S. fradiae, S. antibioticus and S. griseofuscus gave any signal. All of the streptomycetes that gave positive signals were producers of clam-type metabolites (Elson et al., 1987).

Example 3

Disruption of the Genomic cla Gene

A 2.0 kb NcoI fragment that contained the entire cla gene was digested at its unique KpnI site and the ends made blunt by treatment with the Klenow fragment of E. coli DNA polymerase I. A thiostrepton resistance gene (tsr), isolated as a 1085 bp BclI fragment from pIJ702 and cloned into the BamHI site of pUC118 was excised as a SmaI/XbaI fragment and the ends made blunt as above and ligated into the KpnI site of cla. The ligation mixture was introduced into E. coli MV1193 and the transformants screened for the presence of the tsr gene by colony hybridization (Sambrook et al., 1989).

Replacement of the chromosomal cla gene by a copy disrupted by the insertion of tsr, at an internal KpnI site, was achieved by double recombination. Successful gene replacement was apparent when the 2.0 kb NcoI fragment which carries cla in the wild type organism was replaced by a 3.0 kb NcoI fragment due to the insertion of the 1.0 kb tsr gene in the mutants. Pour of the five mutants tested showed the expected increase in the size of the NcoI fragments, and the larger NcoI fragments also hybridized with a tsr specific probe. The fifth mutant was apparently a spontaneous theostrepton resistant mutant.

Antibiotic Assay

The agar diffusion assay was used for determining both penicillin/cephamycin and clavulanic acid production. S. clavuligerus strains to be assayed were grown in 10 ml. amounts of Trypticase Soy Broth (TSB; Baltimore Biological Laboratories) medium with 1.0% starch for 48 h. The cultures were washed twice with 10.3% sucrose and once with MM (Jensen et al. (1982), J. Antibiot., v. 35, pp. 483–490) and the mycelium resuspended in 10.0 mL of MM. Two milliliters of washed cell suspension was inoculated into 100 mL of MM and incubated at 28° C. for 48 h. The cultures were harvested by centrifugation, and the supernatants were assayed for both penicillin/cephamycin and clavulanic acid using bioassay procedures described previously (Jensen et al. (1982), supra).

All of the resulting colonies with disrupted cla genes grew equally well on minimal medium and complex media and produced as much penicillin and cephamycin as did the wild-type, but produced no clavulanic acid (data not shown). HPLC analysis of cell supernatants confirmed the inability of the disrupted cla mutants to synthesize any clavulanic acid (data not shown).

Example 4

Protoplast Formation and Transformation

E. coli competent cell preparation and transformation were as described by Sambrook et al., (1989). Protoplasts of S. clavuligerus were, prepared, transformed and regenerated as described by Bailey et al. (1984), Bio/Technology, v. 2, pp. 808–811, with the following modifications. Dextrin and arginine in the regeneration medium were replaced by starch and sodium glutamate respectively. Protoplasts were heat shocked at 43° C. for 5 min prior to the addition of DNA. Standard procedures were used for protoplasting and transformation of S. lividans (Hopwood et al. (1985)).

The 11.6 kb EcoR1 fragment from K6L2 (FIG. 9) was cloned into the EcoR1 site of pCAT-119. pCAT-119 is derivative of pUC119 which was prepared by insertionally inactivating the ampicillin resistance gene of pUC119 by the insertion of a chloramphenicol acetyltransferase gene (Jensen et al. (1989), Genetics & Molec. Biol. of Ind. Microorg., pp. 239–245 Ed. Hershberger, Amer. Soc. Microbiol). The PCAT-119 plasmid carrying the 11.6 kb fragment was then digested with PstI and ligated to the Streptomyces plasmid pIJ702, which had also been digested with PstI. The resulting bifunctional plasmid carrying the 11.6 kb insert was capable of replicating in either E. coli (with selection for chloramphenicol resistance) or in S. lividans (with selection for thiostrepton resistance). The ligation mixture was transformed to E. coli. Plasmid DNA was isolated from several of the chloramphenicol resistant transformants and analyzed by agarose gel electrophoresis to ensure that the proper plasmid construct was obtained. This isolated plasmid material from E. coli was then transformed into S. lividans as described by Hopwood and transformants were selected by plating onto R2YE medium containing thiostrepton at a concentration of 50 µg/ml.

Thiostrepton resistant S. lividans transformants carrying the bifunctional plasmid with the 11.6 kb insert were patched onto MYM agar plates and allowed to incubate for 48 h at 28° C. before they were overlayered with molten soft nutrient agar containing penicillin G at a concentration of 1 µg/ml and inoculated with Staphylococcus aureus N-2 as indicator organism (Jensen, 1982). (S. aureus N-2 was obtained form the Department of Microbiology Culture Collection, University of Alberta. Any organism which produces a β-lactamase sensitive to clavulanic acid may be used as indicator organism.) Zones of inhibition which appeared around the S. lividans colonies upon incubation overnight at 30° C. were evidence of clavulanic acid production. Clavulanic acid-producing colonies were found amongst these initial S. lividans transformants at a frequency of about 12%. When plasmid DNA was isolated from one of these clavulanic acid-producing transformants and re-introduced into S. lividans, the frequency of clavulanic acid production in these 2nd round transformants was about 40–45%. FIG. 6 shows a photograph of an agar plate bearing 2nd. round transformants. Zones of inhibition are seen as clear areas in the agar; these appear on the photograph as dark circular areas.

Example 5
Sequencing of 15 kb DNA Fragment

Ordered sets of deletions were generated as described in Example 1 using fragments of the DNA insert from the cosmid clone K6L2 (FIG. 9) and subcloned into the E. coli plasmids pUC118 and pUC119. Overlapping fragments were chosen which extended from the end of the pcbC gene downstream for a distance of about 15 kb ending at the BglII site. The deletion generated fragments were sequenced in both orientations as described in Example 1. The sequence is shown in FIG. 2 and SEQ ID NO: 1.

Example 6
Gene Disruption of the 12 kb Fragment

Gene disruption experiments were conducted on the various open reading frames (ORF) to determine if a particular ORF was involved in clavulanic acid production or not. In order to determine the role of the various ORFs in clavulanic acid biosynthesis, mutants disrupted in one of the ORFs were constructed by a gene replacement procedure based on that described in Paradkar and Jensen (*Journal of Bacteriology*, March 1995, Vol. 177, no. 5, pages 1307 to 1314).

In all cases, the apramycin-resistance gene cassette (apr) was used to disrupt the genes encoded within the 12-kb DNA fragment. Before use, unless otherwise indicated, the apr-cassette was modified by adding NcoI restriction sites to both ends. This modification of the apr-cassette has been described in Paradkar and Jensen (*Journal of Bacteriology*, March 1995, Vol. 177, no. 5, pages 1307 to 1314). Since four NcoI sites are present within the 12 kb fragment and present within ORFs 3, 5, 6, and 8, respectively, insertion of the apr-cassette within the NcoI sites created a series of plasmids (called pCATL2) with disruptions in ORFs 3, 5, 6, or 8. The plasmids containing these fragments are referred to as pCATL2orf3, pCATL2orf5, pCATL2orf6, and pCATL2orf8, respectively. The construction of pCATL2orf5 has been previously disclosed (Paradkar and Jensen, *Journal of Bacteriology*, March 1995, Vol. 177, no. 5, pages 1307 to 1314). From each of these plasmids, a smaller fragment carrying only the disrupted gene and some flanking sequence (see details below) was subcloned and finally inserted into the Streptomyces vector pIJ486 (obtained from David A Hopwood, John Innes Institute) for transformation into *S. clavuligerus*. All routine manipulations involved in subcloning were done in *Escherichia coli* using standard cloning vectors, such as pUC119, pBluescript SK+ etc. Since ORF2 and ORF9 do not contain NcoI sites, the disruptions of these ORFs were done in a slightly different manner. The preparation of ORF2, ORF3, ORF6, ORF8 and ORF9 are described in more detail below.

Construction of the Insertional Mutants

1. ORF2 Mutant

NotI-NcoI linker oligonucleotides were added to both ends of the apr gene cassette, and then this modified apr gene fragment was inserted into the NotI site within ORF2 carried on a 2.1-kb EcoRI-BglII fragment. Subsequently, the EcoRI-BglII fragment carrying the disrupted ORF2 was inserted into pIJ486.

Genomic DNA isolated from the wild type (wt) and from an ORF2 mutant was digested with EcoRI and NcoI, and then probed with a 2.1-kb EcoRI-BglII fragment (FIG. 20). The 2.7 kb hybridizing fragment present in the wild type has been replaced with a 1.8 kb fragment in the mutant. A 0.85 kb fragment is also expected to hybridize to the probe in the mutant, but owing to the conditions of electrophoresis under which the gel was that smaller fragment was not retained on the gel. The sizes of the remaining hybridizing fragments are consistent with the replacement of the wild type ORF2 with the apr-disrupted ORF2.

2. ORF3 Mutant

The apr cassette (with NcoI sites on each end) was inserted into the NcoI site within ORF3 carried on a 4 kb EcoRI-KpnI fragment. The fragment carrying the disrupted ORF3 was then subcloned into pIJ486.

Figure 21:
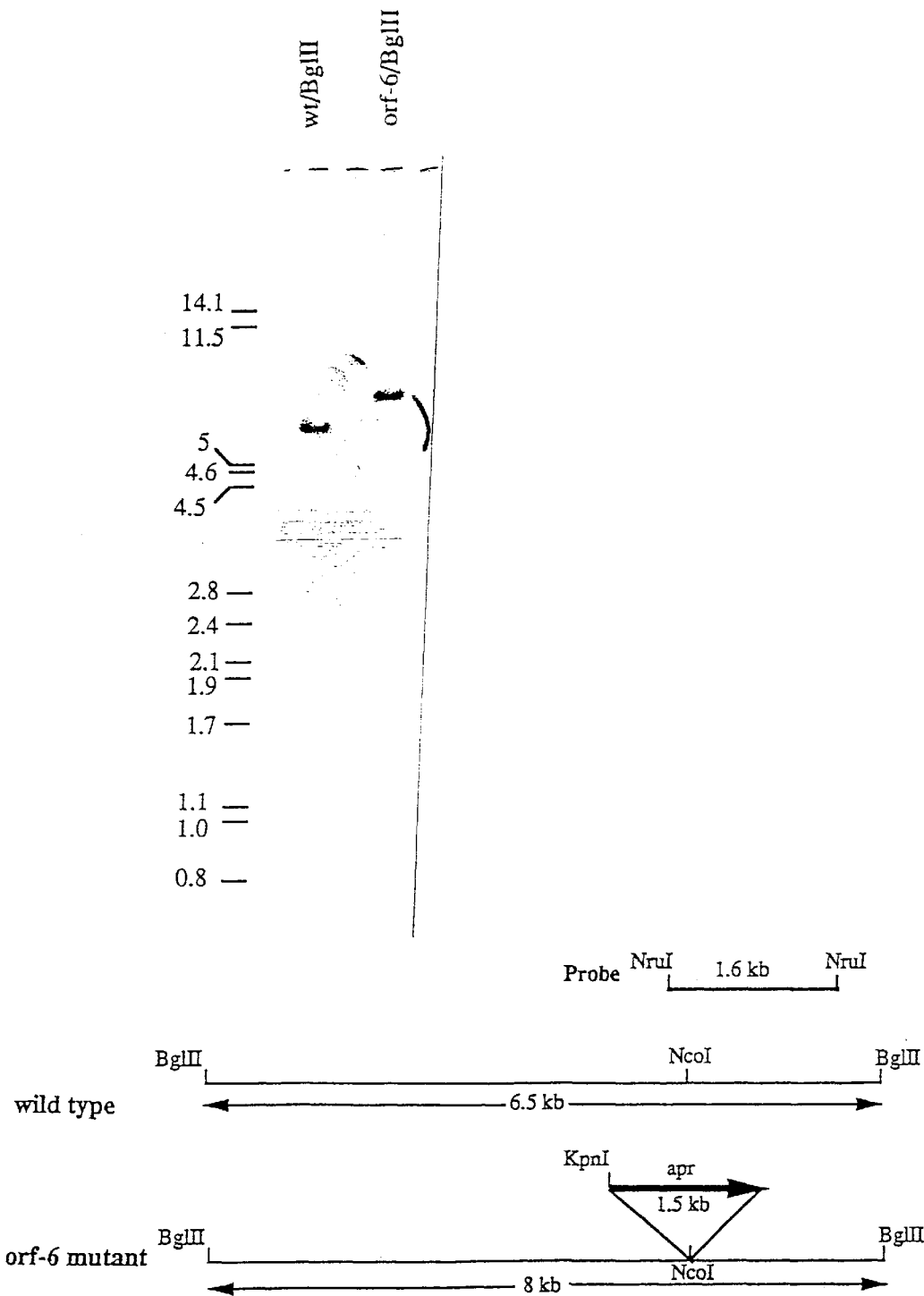

Genomic DNA from the wild type (wt) and from an ORF3 mutant was digested separately with BglII, and with KpnI, and probed with a 0.6-kb BglII-NcoI fragment (FIG. 21). In the BglII digests, the 6.5 kb hybridizing fragment present in the wild type has been replaced with 8 kb fragment in the mutant, while in the KpnI digests, the 5.8 kb fragment has been replaced with a 4.5 kb fragment. The sizes of these hybridizing fragments are consistent with the replacement of the wild type ORF3 with the apr-disrupted ORF3.

3. ORF6 Mutant

An 8-kb BglII fragment carrying the disrupted ORF6 was subcloned from pCATL2orf6 into pIJ486.

Figure 22:
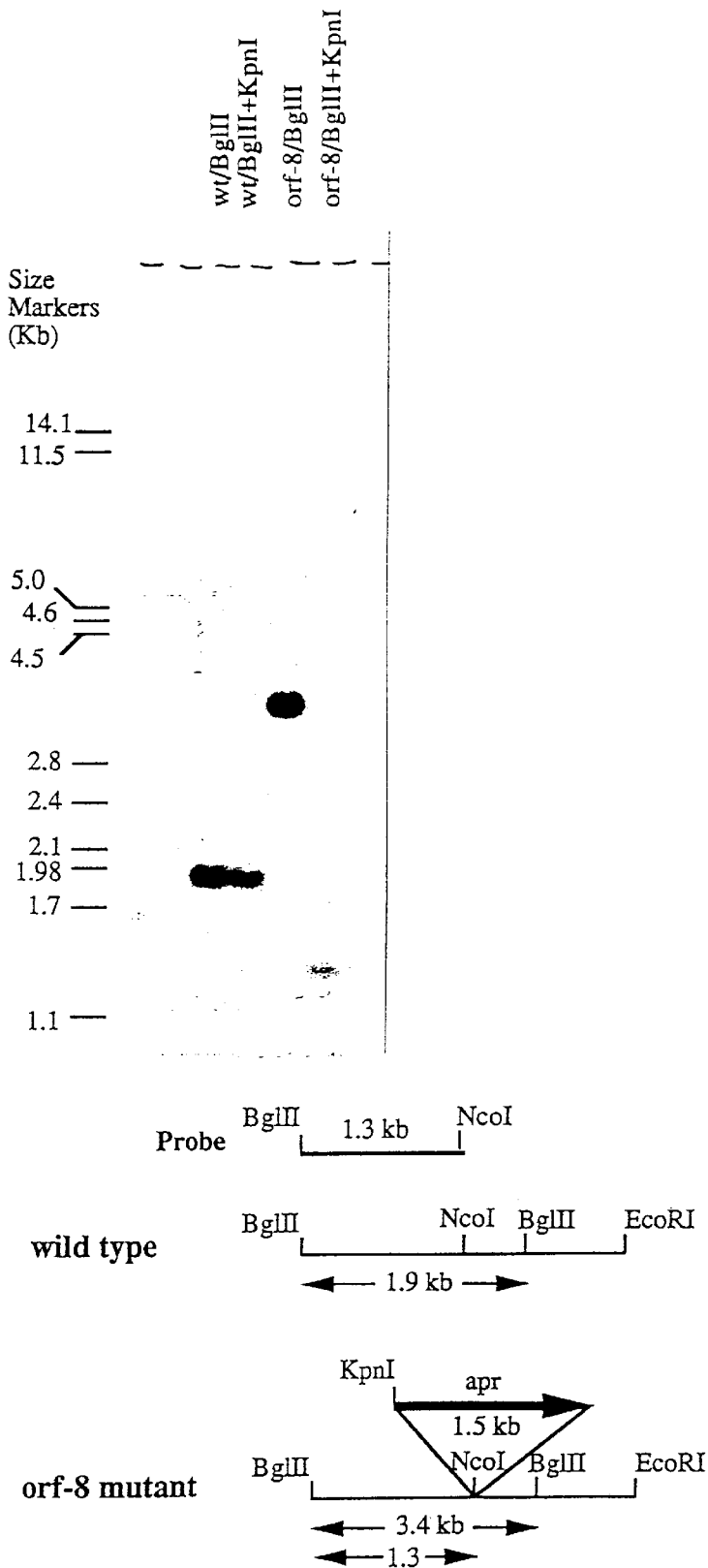

Genomic DNA from the wild type (wt) and from an ORF6 mutant was digested with BglII, and probed with a 1.6-kb NruI fragment (FIG. 22). The 6.5 kb hybridizing fragment present in the wild type has been replaced with an 8 kb fragment in the mutant. The sizes of these hybridizing fragments are consistent with the replacement of the wild type ORF6 with the apr-disrupted ORF6.

4. ORF8 Mutant

A 2.9 kb BglII-EcoRI fragment carrying the disrupted ORF8 was subcloned from pCATL2orf8 into pIJ486.

Figure 23:
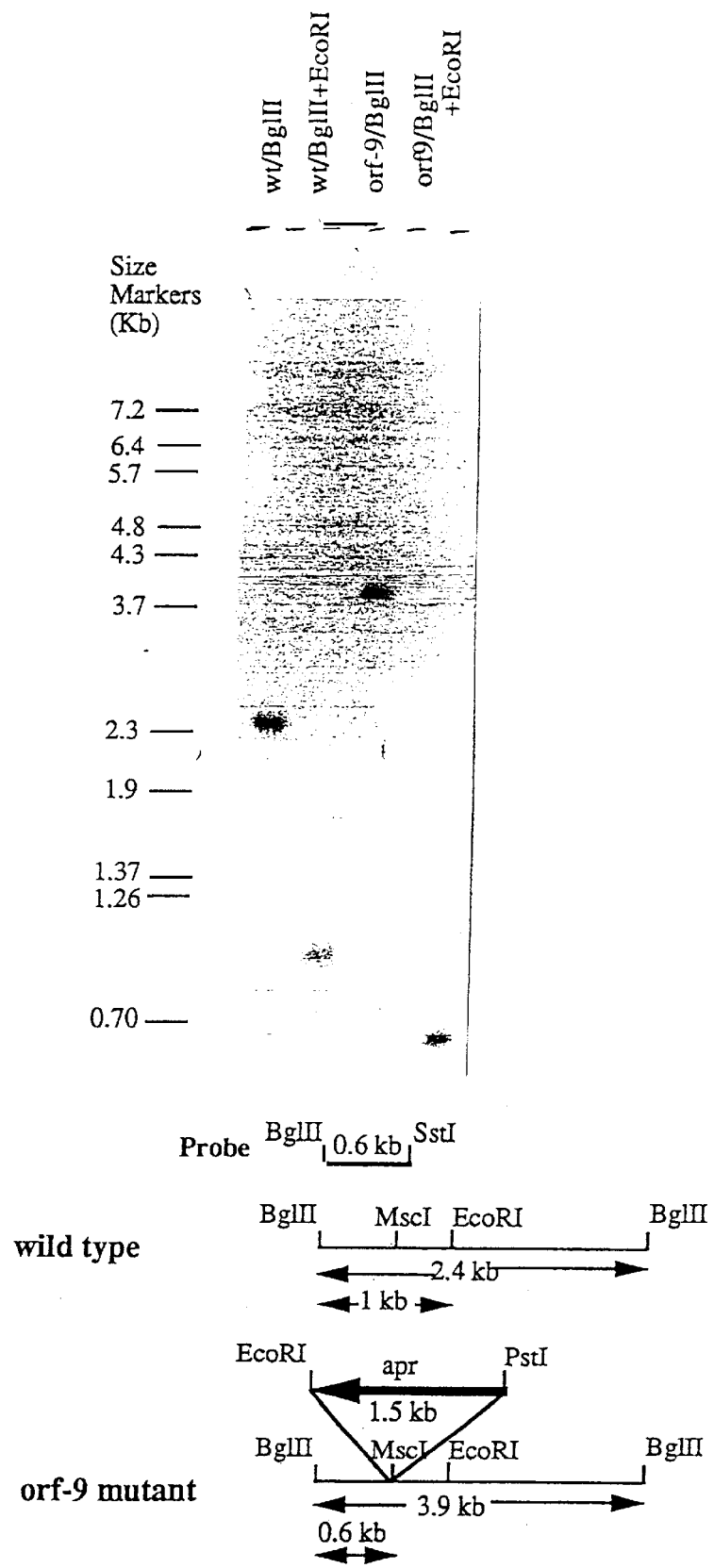

Genomic DNA from the wild type (wt) and from an ORF8 mutant was digested with BglII, and also with both BglII and KpnI, and probed with a 1.3 kb BglII-NcoI fragment (FIG. 23). In the BglII digests, the 1.9 kb hybridizing fragment present in the wild type has been replaced with a 3.4 kb fragment in the mutant, while in the BglII/KpnI digests, the 1.9-kb fragment has been replaced with a 1.3 kb fragment. The sizes of these hybridizing fragments are consistent with the replacement of the wild type ORF8 with the apr-disrupted ORF8.

5. ORF9 Mutant

The apr gene cassette was first cloned as an EcoRI-PstI fragment into the *E. coli* vector Pbluescript, and re-isolated as an EcoRV-SmaI fragment. This fragment was then inserted into the MscI site present in ORF9 contained within a 2.4 kb BglII fragment. Subsequently, the 4 kb fragment carrying the disrupted ORF9 was inserted into pIJ486.

Figure 24A:
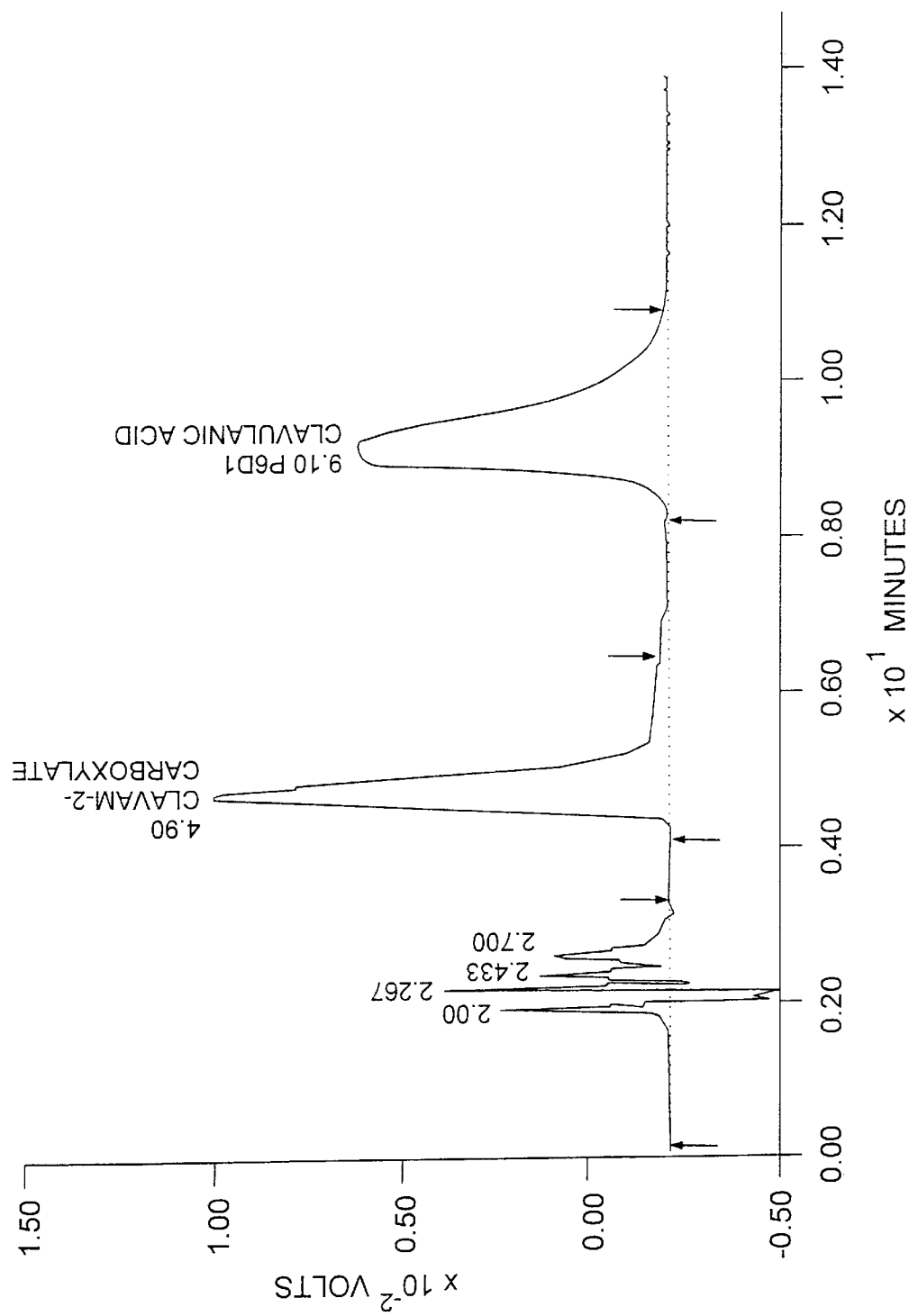
FIGS. 24(A), (B) and (C), high pressure liquid chromatography (HPLC) analysis of clavulanic acid in culture supernatants. Culture supernatants from 96 hour Starch-Asparagine medium-grown cultures of either wild type S. clavuligerus, or one of the gene disruption mutants were analyzed by HPLC. (A)Retemion time of a clavulanic acids standard; (B) Wild type culture supernatant showing a peak due to clavulanic acid eluting with a retention time of 6.5 min. (C) Gene disruption mutant culture supernatant (ORF8 mutant). The same HPLC profile was seen for all of the other disruption mutants, including ORF2, ORF3, or ORF9, indicating that none of the mutants produced clavulanic acid under these culture conditions.
Figure 24B:
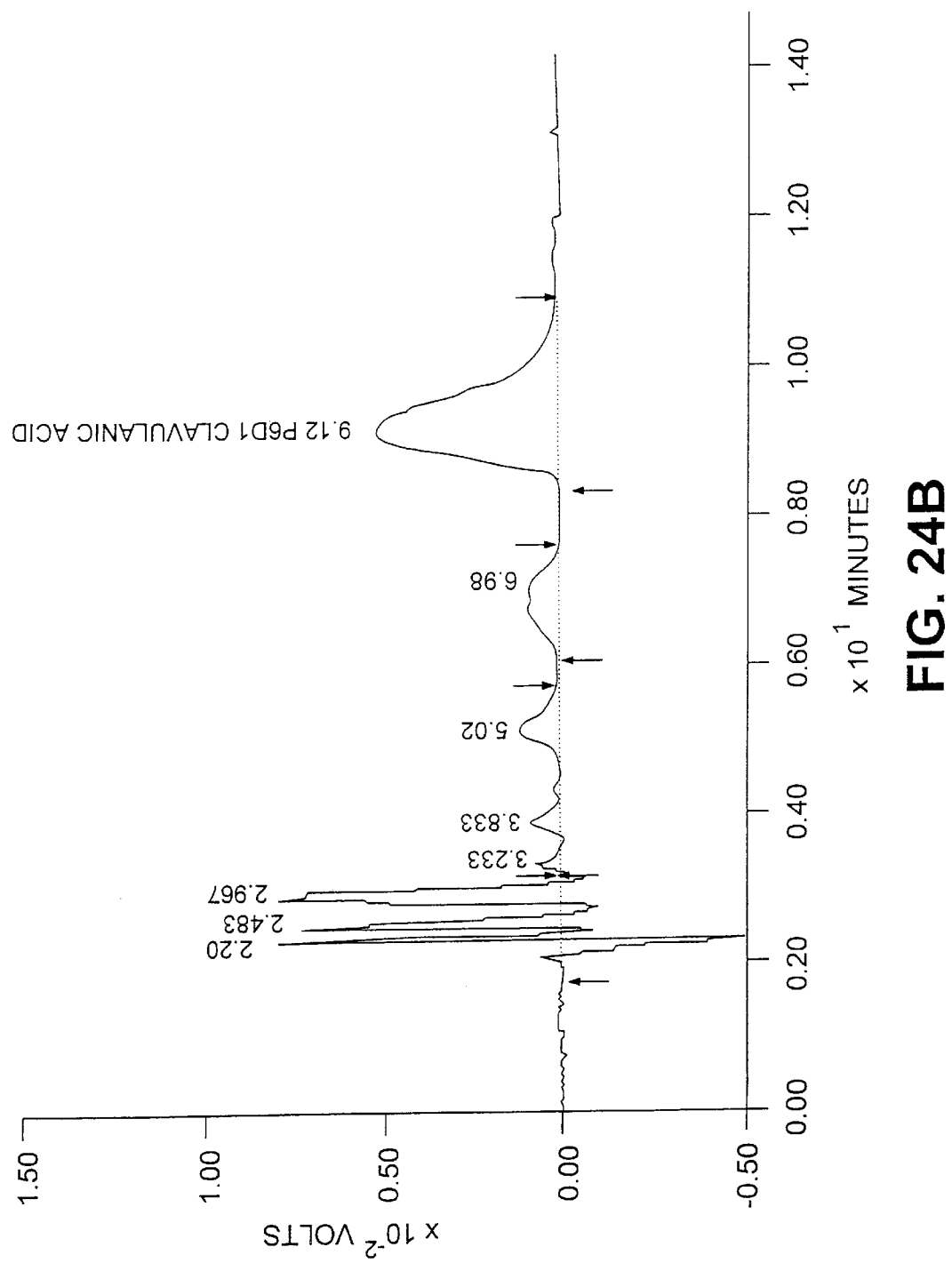
Figure 24C:
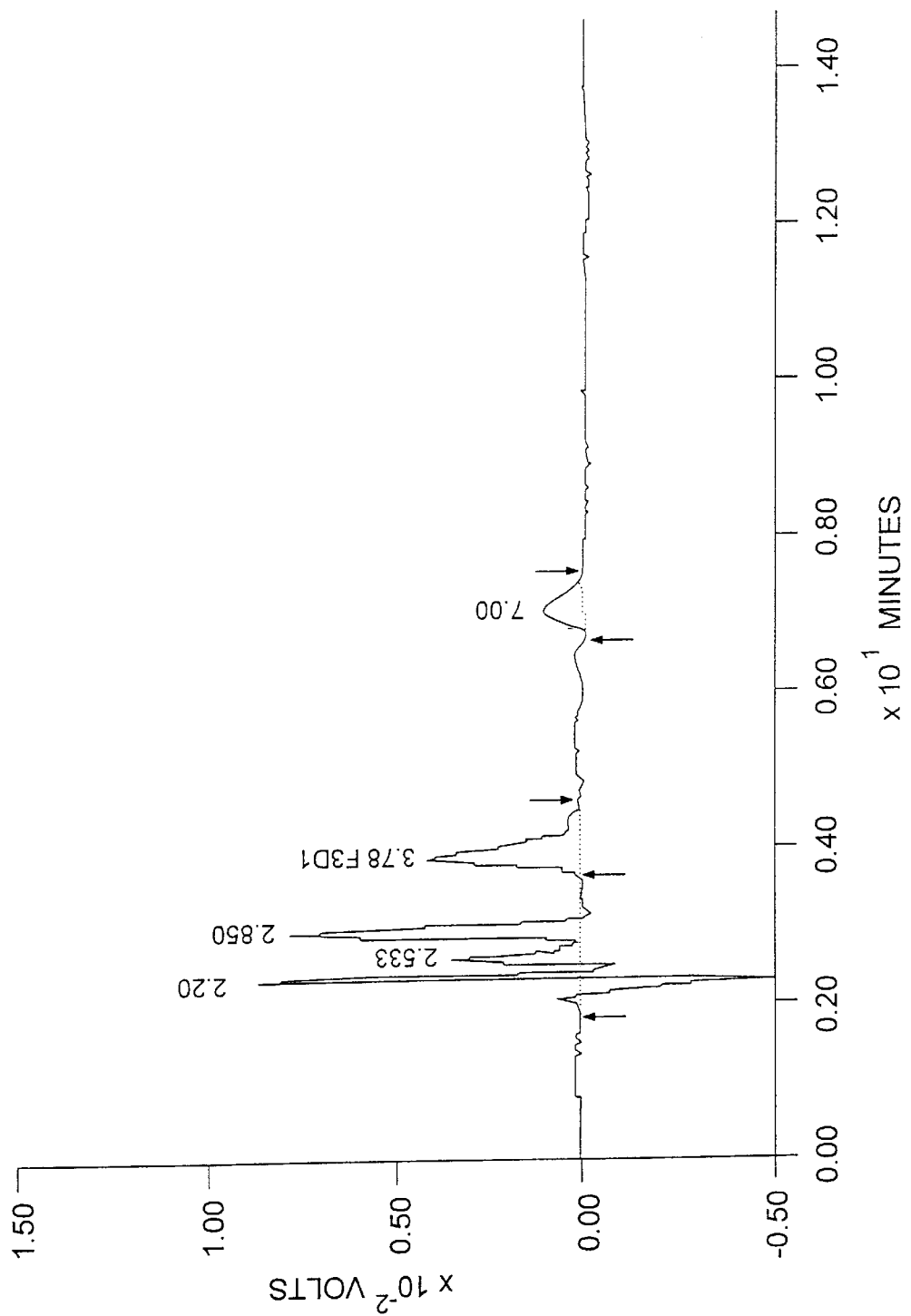

Genomic DNA from the wild type (wt) and an ORF9 mutant was digested with BglII, and with both BglII and EcoRI, and probed with a 0.6-kb BglII-SstI fragment (FIG. 24). In the BglII digests, the 2.4 kb hybridizing fragment present in the wild type has been replaced with a 3.9 kb fragment in the mutant, while in the BglII-EcoRI digests, the 1-kb fragment has been replaced with a 0.6 kb fragment. In BglII-EcoRI digests of the ORF9 mutant genomic DNA another 3.3-kb EcoRI-BglII fragment might have been expected to hybridize to the probe, but failure to see this fragment can be attributed to the fact that the probe has only approximately 50 bp of sequence homologous to the expected fragment. Since the post-hybridization washes were carried out under stringent conditions this small amount of homology might not be sufficient to give a hybridizing band. Nevertheless, the sizes of other hybridizing fragments are consistent with the replacement of the wild type ORF9 with the apr disrupted ORF9.

The Effect of Mutations Within the ORF's of the 12 kb Fragment on Clavulanic Acid Synthesis 1. Bioassay Clavulanic acid production in *S. lividans* transformants was bioassayed by the method of Jensen et al., (Industrial Microorganisms:Basic and Applied Molecular Genetics, 1993, Chapter 22, Edited by R. H. Baltz, G. D. Hegemam, P. L. Skatrud, Published by The American Society for Microbiology, Washington, D.C.). Basically the method involves patching select transformants onto agriplates, and after a 48 hours incubation period at 28° C., overlayering these organisms with a β-lactamase-producing indicator organism, together with penicillin G, at a concentration of 1 $\mu$/ml. The results are summarized below:

TABLE II

| Strain | No Penicillin | Penicillin G (1 $\mu$/ml) |
| --- | --- | --- |
| wild type | 0 mm | 28 mm |
| ORF2 | 0 mm | 0 mm |
| ORF3 | 0 mm | 0 mm |
| ORF6 | 0 mm | 0 mm |
| ORF8 | 0 mm | 0 mm |
| ORF9 | 0 mm | 0 mm |

If a zone of inhibition is obtained in the presence of penicillin but not in the absence thereof or if the size of the zones in the presence of penicillin is greater than the zones without penicillin, it is indicative of a β-lactamase inhibitory activity of clavulanic acid. The bioassay thus showed that transformants containing mutants with insertion in any one of the ORF2, ORF3, ORF6, ORF8 or ORF9 failed to produce β-lactamase inhibitory activity of clavulanic acid, thus indicating that each of these ORFs are involved in the production of clavulanic acid.

2. HPLC Analysis

The amount of clavulanic acid produced by each transformant was also quantitated in each sample by HPLC. This assay was done to confirm the presence or absence of clavulanic acid production, within the cultured supernatants produced from each gene disruption mutant.

Culture Conditions for the Growth of Wild Type and the Mutants for Clavulanic Acid Production Spores of transformants containing insertional mutations within either ORF2, ORF3, ORF6, ORF8 or ORF9 were first inoculated into 20 mL Trypticase Soy Broth containing 1% starch, and the culture was grown shaking for 48 hours at 28° C. which served as a seed culture. The seed culture was then used at 1% inoculum to inoculate 20 ml Starch Asparagine medium the composition of which has been described earlier (Paradkar and Jensen (1995), J Bacteriol Vol. 177, pp. 1307–1314), and the culture was grown in the same conditions as the seed culture. Supernatants (0.1 mL) were obtained from 96 hour cultures, and derivatized with 25 $\mu$L of imidazole reagent. Subsequently, a 50 $\mu$L aliquot of the derivatized sample was analyzed by HPLC.

The high pressure liquid chromatography assay was conducted as described in Foulstone and Reading (1982, Antimicrob. Agents Chemother. 22:753–762).

Analysis was performed with a model M-45 pump, model 712 WISP automated sample injector, and model 480 variable-wavelength UV detector, all from Millipore Waters (Mississauga, Ontario, Canada). Samples (100 $\mu$l) were mixed with imidazole reagent (25 $\mu$l) and incubated at room temperature for 15 min to form imidazole-derivatized clavulanic acid. Derivatized samples (50 $\mu$l) were analyzed on a reverse-phase column ($\mu$Bondapak-C18) with an isocratic buffer system consisting of 0.1 M $KH_2PO_4$-6% methanol, PH 3.2 (adjusted with $H_3PO_4$). Under these conditions, authentic clavulanic acid has a retention time of 6.5 min.

The HPLC chromatograms of culture supernatants from transformants containing an insertional mutation within ORF2, ORF3, ORF6, ORF8 or ORF9 and of the wild type were obtained. An example of these results is illustrated in FIG. 25, which represents the HPLC profile of wild type (B) or the ORF8 insertion mutant (C). As can be seen from FIG. 25, clavulanic acid was detected in the supernatant of the wild type as a peak, at a retention time of 9.1 minutes. An authentic sample of clavulanic acid also gave a retention time of approximately 9.1 minutes (FIG. 25 (A). The amount of clavulanic acid produced by the wild type was determined by integrating the clavulanic acid peak in the wild type supernatant.

The present invention is not limited to the features of the embodiments described herein, but includes all variations and modifications within the scope of the claims.

We claim:

1. An isolated protein having an amino acid sequence selected from the group consisting of SEQ ID NOS: 4, 5, 8, 9, 10 and 11.

2. The isolated protein of claim 1 having the amino acid sequence of SEQ ID NO:4.

3. The isolated protein of claim 1 having the amino acid sequence of SEQ ID NO:5.

4. The isolated protein of claim 1 having the amino acid sequence of SEQ ID NO:8.

5. The isolated protein of claim 1 having the amino acid sequence of SEQ ID NO:9.

6. The isolated protein of claim 1 having the amino acid sequence of SEQ ID NO:10.

7. The isolated protein of claim 1 having the amino acid sequence of SEQ ID NO: 11.

* * * * *

SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
      (A) LENGTH: 15079 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Streptomyces clavuligerus (xi) SEQUENCE DESCRIPTION: SEQ ID NO: 1:

```
GCGGAACCGG CCGCCCCTGA GCGGGCGGC CGGGAAGGAA ACGGGCCGGT CGTCCCCTCG        60

GGAGGGGGCG GCCGGCCCGT CCGGTGCGCG CGGTGGGTGC GGCGCGGGTC AGCCGGCCGC       120

GAGGTTGCTG AGGAACTTCG CGGCGACGGG GCCCGCGTCG GCGCCGCCCG ACCCGCCGTC       180

CTCCAGCAGG ACCGACCAGG CGATGTTCCG GTCGCCCTGG TAGCCGATCA TCCAGGCGTG       240

CGTCTTCGGC GGCTTCTCGG TGCCGAACTC GGCGGTACCG GTCTTGGCGT GCGGCTGTCC       300

GCCGAGGCCC CGCAGGGCGT CGCCGGCGCC GTCGGTGACG GTCGAACGCA TCATGGAACG       360

CAGCGAGTCG ACGATGCCCG GGGCCATCCG GGGGCCTGG TGCGGCTTCT TGACCGCGTC        420

GGGCACCAGC ACGGGCTGCT TGAACTCGCC CTGCTTGACG GTGGCGGCGA TGGAGGCCAT       480

CACCAGGGGC GACGCCTCGA CCCTGGCCTG TCCGATGGTG GACGCGGCCT TGTCGTTCTC       540

GCTGTTGGAG ACGGGACGC TGCCGTCGAA GGTGGAGGCG CCGACGTCCC AGGTGCCGCC        600

GATGCCGAAG GCTTCGGCGG CCTGCTTCAG GCTGGACTCG GAGAGCTTGC TGCGGGAGTT      660

GACGAAGAAC GTGTTGCAGG AGTGGGCGAA GCTGTCCCGG AAGGTCGAGC CCGCGGGCAG       720

CGTGAACTGG TCCTGGTTCT CGAAGCTCTG GCCGTTGACA TGGGCGAACT TCGGGCAGTC       780

GGCCCGCTCC TCCGGGTTCA TCCCCTGCTG GAGCAGGGCC GCGGTGGTGA CCACCTTGAA       840

GGTGGAGCCG GGCGGGTAGC GGCCCTCCAG CGCGCGGTTC ATGCCGGAGG GCACGTTCGC       900

GGCGGCCAGG ATGTTGCCGG TGGCGGGGTC GACGGCGACG ATCGCCGCGT TCTTCTTCGA       960

GCCCTCCAGG GCCGCCGCGG CGGCGGACTG GACCCGCGGG TCGATGGTGG TCTTCACCGG      1020

CTTGCCCTCG GTGTCCTTGA GGCCGGTGAG CTTCTTGACC ACCTGGCCGG ACTCACGGTC      1080

CAGGATCACG ACCGAGCGCG CCGCGCCGGA GCCGCCGGTG AGCTGCTTGT CGTAGCGGGA      1140

CTGGAGGCCC GCCGAGCCCT TGCCGGTCCT GGGGTCGACC GCGCCGATGA TGGAGGCGGC      1200

CTGGAGGACA TTGCCGTTGG CGTCGAGGAT GTCCGCGCGC TCCCGCGACT TGAGGGCGAG      1260

GGTCTGCCCC GGAACCATCT GCGGATGGAT CATCTCGGTG TTGAACGCGA CCTTCCACTC      1320

CTTGCCGCCG CCGACGACCT TCGCGGTGGA GTCCAGGCG TACTCCCCGG CCCCGGGGAG       1380

GGTCATTCTG ACGGTGAACG GTATCTCCAC CTCGCCCTCG GGGTTCTTCT CCCCGGTCTT      1440

GGCGGTGATC TCCGTCTTCG TCGGCTTGAG GTTGGTCATG ACGGATTTGA TCAGCGACTC      1500

GGCGTTGTCC GGGGTGTCCG TCAGCCCGGC GGCCGTCGGG GCGTCGCCCT TCTCCCAGGC      1560

GCCGAGGAAG GTGTCGAACT GTCCGGCCGC CGCCTCCACC TCGGGGTCGC CCGAATCCTT      1620

CTCGTCGGCA ACCAGGCTGG TGTAACCCCA ATAGCCGAGC CCCACCGTCA CGGCCAGCCC      1680

GGCGACCACC GCGGTGGCCG CCCGGCCACG GGAGCGGCGC CTGCCCTGCG GCGGGTCATC      1740

GCCATAGTTG TCGGAATGCG TCATGGGGCC AGGCTATGCG GGCGCCCTCT TTCCCTCCTC      1800

CCCGGATACC GCGTTTCAGG ACAGTCAAGG GGCCGAACGG AGGGCTGGAC CAGCCGCTCA      1860

GCGGCCCGTT CCCACCCCTT GGGGGAAGC GGCACCCGGA AGGTGACCGA GCAACATCC        1920

ATGGAAAGGG GAGCGAATCG GTCGCCGAGT TCACCGCGAT GGAGTAGAC CTCTGAAAGC       1980

GTGACAGCGG GGAGTAGCGA CAAAACGGTC AGACCCCTGA AGGGAATTGA CTGAATTCGA      2040

GTCATCGGGT TCGGCGACGG ATGGGCGGTT CGGCCACGCA CCGTCACTCT TCGTCCCCTC      2100

TTCACAAGAA CTCCCGATAC GTGGAGAAGA GAGCGTGAAG AGCGCGTCCG GTCAGGGTTG      2160

CCGAGAACCG TCCACCATGA CGGAGCCTGG TACTGACGGA GTCTGGAGAC CGCTCATGTC      2220

CCGTGTATCG ACCGCCCCCA GCGGCAAGCC TACCGCCGCT CACGCCCTCC TGTCACGGTT      2280

GCGTGATCAC GGTGTGGGA AGGTGTTTGG GGTTGTCGGC CGAGAGGCCG CGTCGATTCT       2340
```

```
CTTCGACGAG GTCGAGGGGA TCGACTTCGT TCTGACCCGC CACGAGTTCA CCGCGGGTGT   2400

CGCCGCTGAT GTCCTCGCGC GGATCACCGG TCGCCCCCAG GCGTGCTGGG CCACCCTGGG   2460

CCCCGGTATG ACCAACCTCT CCACCGGTAT CGCCACGTCC GTCCTGGACC GCTCGCCGGT   2520

CATCGCGCTC GCCGCGCAGT CGGAGTCGCA CGACATCTTC CCGAACGACA CCCACCAGTG   2580

CCTGGACTCG GTGGCGATCG TCGCCCCGAT GTCCAAGTAC GCCGTGGAGC TCCAGCGGCC   2640

CCACGAGATC ACCGACCTCG TCGACTCCGC CGTGAACGCG GCCATGACCG AGCCGGTCGG   2700

GCCCTCCTTC ATCTCCCTCC CGGTGGACCT GCTCGGCTCC TCCGAGGGCA TCGACACCAC   2760

CGTCCCCAAC CCGCCGGCGA ACACCCCGGC GAAACCGGTC GGCGTCGTCG CCGACGGCTG   2820

GCAGAAGGCC GCCGACCAGG CCGCCGCCCT GCTCGCCGAG GCCAAGCACC CGGTGCTCGT   2880

CGTCGGAGCG GCCGCGATCC GCTCGGGCGC CGTCCCGGCG ATCCGCGCCC TGGCCGAGCG   2940

CCTGAACATC CCGGTCATCA CGACCTACAT CGCCAAGGGT GTCCTGCCGG TCGGCCACGA   3000

GCTGAACTAC GGCGCCGTCA CCGGCTACAT GGACGGCATC CTCAACTTCC CGGCGCTCCA   3060

GACCATGTTC GCCCCGGTGG ACCTCGTCCT CACCGTCGGC TACGACTACG CCGAGGACCT   3120

GCGCCCGTCC ATGTGGCAGA AGGGCATCGA GAAGAAGACC GTCCGTATCT CCCCGACGGT   3180

CAACCCGATC CCCCGGGTCT ACCGGCCCGA CGTCGACGTC GTCACCGACG TCCTCGCCTT   3240

CGTGGAGCAC TTCGAGACCG CGACCGCCTC CTTCGGGGCC AAGCAGCGCC ACGACATCGA   3300

GCCGCTGCGC GCCCGGATCG CGGAGTTCCT GGCCGACCCG GAGACCTACG AGGACGGCAT   3360

GCGCGTCCAC CAGGTCATCG ACTCCATGAA CACCGTCATG GAGGAGGCCG CCGAGCCCGG   3420

CGAGGGCACG ATCGTCTCCG ACATCGGCTT CTTCCGTCAC TACGGTGTGC TCTTCGCCCG   3480

CGCCGACCAG CCCTTCGGCT TCCTCACCTC GGCGGGCTGC TCCAGCTTCG GCTACGGCAT   3540

CCCCGCCGCC ATCGGCGCCC AGATGGCCCG CCCGGACCAG CCGACCTTCC TCATCGCGGG   3600

TGACGGCGGC TTCCACTCCA ACAGCTCCGA CCTGGAGACC ATCGCCCGGC TCAACCTGCC   3660

GATCGTGACC GTCGTCGTCA ACAACGACAC CAACGGCCTG ATCGAGCTGT ACCAGAACAT   3720

CGGTCACCAC CGCAGCCACG ACCCGGCGGT CAAGTTCGGC GGCGTCGACT TCGTCGCGCT   3780

CGCCGAGGCC AACGGTGTCG ACGCCACCCG CGCCACCAAC CGCGAGGAGC TGCTCGCGGC   3840

CCTGCGCAAG GGTGCCGAGC TGGGTCGTCC GTTCCTCATC GAGGTCCCGG TCAACTACGA   3900

CTTCCAGCCG GGCGGCTTCG CGCCCTGAG CATCTGATCA TGGGGCACC GGTTCTTCCG    3960

GCTGCCTTCG GGTTCCTGGC CTCCGCCCGA ACGGGCGGGG GCCGGGCCCC CGGCCCGGTC   4020

TTCGCGACCC GGGGCAGCCA CACCGACATC GACACGCCCC AGGGGGAGCG CTCGCTCGCG   4080

GCGACCCTGG TGCACGCCCC CTCGGTCGCG CCCGACCGCG CGGTGGCGCG CTCCCTCACC   4140

GGCGCGCCCA CCACCGCGGT GCTCGCCGGT GAGATCTACA ACCGGGACGA ACTCCTCTCC   4200

GTGCTGCCCG CCGGACCCGC GCCGGAGGGG GACGCGGAGC TGGTCCTGCG GCTGCTGGAA   4260

CGCTATGACC TGCATGCCTT CCGGCTGGTG AACGGGCGCT TCGCGACCGT GGTGCGGACC   4320

GGGGACCGGG TCCTGCTCGC CACCGACCAC GCCGGTTCGG TGCCGCTGTA CACCTGTGTG   4380

GCGCCGGGCG AGGTCCGGGC GTCCACCGAG GCCAAGGCGC TCGCCGCGCA CCGCGACCCG   4440

AAGGGCTTCC CGCTCGCGGA CGCCCGCCGG GTCGCCGGTC TGACCGGTGT CTACCAGGTG   4500

CCCGCGGGCG CCGTGATGGA CATCGACCTC GGCTCGGGCA CCGCCGTCAC CCACCGCACC   4560

TGGACCCCGG GCCTCTCCCG CCGCATCCTG CCGGAGGGCG AGGCCGTCGC GGCCGTGCGG   4620

GCCGCGCTGG AGAAGGCCGT CGCCCAGCGG GTCACCCCCG GCGACACCCC GTTGGTGGTG   4680

CTCTCCGGCG GAATCGACTC CTCCGGGGTC GCGGCCTGTG CGCACCGGGC GGCCGGGGAA   4740
```

```
CTGGACACGG TGTCCATGGG CACCGACACG TCCAACGAGT TCCGCGAGGC CCGGGCGGTC    4800

GTCGACCATC TGCGCACCCG GCACCGGAG ATCACCATCC CGACCACCGA GCTGCTGGCG    4860

CAGCTCCCGT ACGCGGTGTG GGCCTCCGAG TCGGTGGACC CGGACATCAT CGAGTACCTG    4920

CTCCCCCTGA CAGCGCTCTA CCGGGCGCTC GACGGGCCGG AGCGCCGCAT CCTCACCGGG    4980

TACGGCGCGG ACATCCCCCT CGGGGGCATG CACCGCGAGG ACCGGCTGCC CGCGCTGGAC    5040

ACCGTTCTCG CGCACGACAT GGCCACCTTC GACGGGCTGA ACGAGATGTC CCCGGTGCTG    5100

TCCACGCTGG CGGGGCACTG GACCACCCAC CCGTACTGGG ACCGGGAGGT CCTCGATCTG    5160

CTGGTCTCGC TGGAGGCCGG GCTCAAGCGG CGGCACGGCC GGGACAAGTG GGTGCTGCGC    5220

GCCGCGATGG CCGACGCCCT CCCGGCGGAG ACCGTCAACC GGCCCAAGCT GGGCGTCCAC    5280

GAGGGCTCGG GCACCACGTC CTCGTTCTCC CGGCTGCTGC TGGACCACGG TGTCGCCGAG    5340

GACCGCGTCC ACGAGGCGAA GCGGCAGGTG GTGCGCGAGC TGTTCGATCT CACGGTCGGG    5400

GGCGGACGGC ACCCCTCCGA GGTGGACACC GACGATGTGG TGCGCTCCGT GGCCGACCGG    5460

ACCGCGCGGG GGCGGCCTA GTCCCGCCAC GGGGAGCCCG CCGGACGCCG ACCCGCGCG    5520

GGACCCGTAC CCGGGGCCGC CCGCGGACTC CGGCGCACCG GCACCCCTGT CCCCCACCCG    5580

TTGACGACCG TCGGCCCTCG GCCCTCGCGG CCCCTGACGA CCGTCGCCCG ATTCCCAGGA    5640

GGGAGCTGAA AGCGTGGAGC GCATCGACTC GCACGTTTCA CCCCGCTACG CACAGATCCC    5700

CACCTTCATG CGCCTGCCGC ACGATCCCCA GCCCCGCGGC TATGACGTGG TGGTCATCGG    5760

AGCCCCCTAC GACGGGGGCA CCAGCTACCG TCCCGGCGCC CGGTTCGGCC CCCAGGCCAT    5820

CCGCAGTGAG TCGGGCCTCA TCCACGGTGT CGGCATCGAC CGGGGCCCCG GCACGTTCGA    5880

CCTGATCAAC TGTGTCGACG CCGGGGACAT CAATCTGACG CCGTTCGACA TGAACATCGC    5940

GATCGACACG GCGCAGAGCC ATCTGTCGGG CCTGCTGAAG GCCAACGCCG CCTTTCTGAT    6000

GATCGGCGGC GACCACTCGC TGACGGTGGC CGCCCTGCGC GCGGTCGCGG AGCAGCACGG    6060

CCCGCTCGCC GTGGTGCACC TGGACGCGCA CTCCGACACC AACCCGGCCT TCTACGGGGG    6120

CCGGTACCAC CACGGCACCC CCTTCCGGCA CGGGATCGAC GAGAAGCTGA TCGACCCGGC    6180

GGCGATGGTC CAGATCGGCA TCCGGGGCCA CAACCCGAAG CCGGACTCGC TCGACTACGC    6240

CCGGGGCCAC GGCGTCCGGG TGGTCACGGC GGACGAGTTC GGCGAGCTGG GGGTGGGCGG    6300

GACCGCCGAC CTCATCCGCG AGAAGGTCGG CCAGCGGCCC GTGTACGTCT CGGTCGACAT    6360

CGACGTGGTC GACCCCGCCT TCGCCCCCGG TACGGGCACG CCCGCGCCGG GCGGGCTCCT    6420

CTCGCGCGAG GTGCTGGCGC TGCTGCGCTG CGTGGGTGAC CTGAAGCCGG TCGGCTTCGA    6480

CGTGATGGAG GTGTCACCCC TCTACGACCA CGGCGGGATC ACTTCGATCC TGGCCACGGA    6540

GATCGGTGCG GAACTGCTCT ACCAGTACGC CCGAGCCCAC AGAACCCAGT TGTGAAGGAG    6600

ACATCGTGTC ATGGCCTCTC CGATAGTTGA CTGCACCCCG TACCGCGACG AGCTGCTCGC    6660

GCTCGCCTCC GAGCTTCCCG AGGTGCCGCG CGCGGACCTC CATGGCTTCC TCGACGAGGC    6720

GAAGACGCTG GCCGCCCGTC TCCCGGAGGG GCTGGCCGCC GCTCTCGACA CCTTCAACGC    6780

CGTGGGCAGC GAGGACGGTT ATCTGCTGCT GCGCGGGCTG CCCGTCGACG ACAGCGAGCT    6840

GCCCGAGACG CCGACCTCCA CCCCGGCCCC GCTGGACCGC AAGCGGCTGG TGATGGAGGC    6900

CATGCTCGCG CTGGCCGGCC GCCGGCTCGG TCTGCACACG GGGTACCAGG AGCTGCGCTC    6960

GGGCACGGTC TACCACGACG TGTACCCGTC GCCCGGCGCG CACTACCTGT CCTCGGAGAC    7020

CTCCGAGACG CTGCTGGAGT TCCACACGGA GATGGCGTAC CACATCCTCC AGCCGAACTA    7080

CGTCATGCTG GCCTGCTCCC GCGCGGACCA CGAGAACCGG GCGGAGACGC TGGTCGGCTC    7140
```

```
GGTCCGCAAG GCGCTGCCCC TGCTGGACGA GAAGACCCGG GCCCGTCTCT TCGACCGCAA    7200

GGTGCCCTGC TGCGTGGACG TGGCCTTCCG CGGCGGGGTC GACGACCCGG GCGCGATCGC    7260

CAACGTCAAG CCGCTCTACG GGACGCGAA CGACCCGTTC CTCGGGTACG ACCGCGAGCT    7320

GCTGGCGCCG GAGGACCCCG CGGACAAGGA GGCCGTCGCC CATCTGTCCC AGGCGCTCGA    7380

CGATGTGACC GTCGGGGTGA AGCTCGTCCC CGGTGACGTC CTCATCATCG ACAACTTCCG    7440

CACCACGCAC GCGCGGACGC CGTTCTCGCC CCGCTGGGAC GGGAAGGACC GCTGGCTGCA    7500

CCGCGTCTAC ATCCGCACCG ACCGCAATGG ACAGCTCTCC GGCGGCGAGC GCGCGGGCGA    7560

CACCATCTCG TTCTCGCCGC GCCGCTGAGC CCGGCTCCCC GAGGCCCTGG GCCCCGGCGC    7620

CGGAACCGGC TCCCGGTCCT GCCCCCTCAC CCGCCGCGCG GGTGAGGGGG CAGGCCCCTT    7680

TGTGCCGGGT GCCGTGCGTC CTGCGAGGGT GCCGGGCGG GGGGACGGC GGAGGTGCCC    7740

GGCGGCCGGG TGCCGTGCGC CGCCCGTGGG TGCTGTACAG CACTCCGTGT GCCGTGCGCC    7800

ACCCCGTGCA TAAATTTGCC ACTCTATGGG AAATAATGCA GAGTGCGACG GGTGAGGCCG    7860

TCGCCGTGCC CTTTCCGTGA CAGGAGACGC TGACATGTCC GACAGCACAC CGAAGACGCC    7920

CCGGGGATTC GTGGTGCACA CGGCGCCGGT GGGCCTGGCC GACGACGGCC GCGACGACTT    7980

CACCGTCCTC GCCTCCACCG CCCCGGCCAC CGTGAGCGCC GTCTTCACCC GCTCCCGCTT    8040

CGCCGGGCCG AGCGTCGTGC TGTGCCGGGA GGCGGTGGCC GACGGGCAGG CGCGCGGTGT    8100

GGTGGTGCTG GCCCGCAACG CGAATGTCGC GACCGGCCTG GAGGGCGAGG AGAACGCGCG    8160

CGAGGTGCGC GAGGCCGTCG CCCGGGCCCT CGGGCTGCCG GAGGGCGAGA TGCTGATCGC    8220

CTCCACCGGG GTGATCGGCC GGCAGTACCC GATGGAGAGC ATCCGGGAGC ACCTCAAGAC    8280

GCTGGAGTGG CCCGCCGGGG AGGGCGGCTT CGACCGCGCG GCCCGCGCCA TCATGACGAC    8340

CGACACCCGG CCCAAGGAGG TCCGGGTCAG CGTCGGCGGG GCGACCCTCG TGGGCATCGC    8400

CAAGGGCGTC GGCATGCTGG AGCCCGACAT GGCGACGCTG CTGACCTTCT TCGCCACGGA    8460

CGCCCGGCTG GACCCGGCCG AGCAGGACCG CCTCTTCCGC CGGGTCATGG ACCGCACCTT    8520

CAACGCGGTC AGCATCGACA CCGACACCTC CACCAGCGAC ACGGCGGTGC TGTTCGCCAA    8580

CGGCCTGGCG GGCGAGGTCG ACGCCGGGGA GTTCGAGGAG CGCTGCACA CGGCGGCGCT    8640

GGCCCTGGTC AAGGACATCG CGAGCGACG CGAGGGCGCG GCCAAGCTGA TCGAGGTCCA    8700

GGTCACCGGC GCCCGCGACG ACGCCCAGGC CAAGCGGGTC GGCAAGACCG TCGTCAACTC    8760

CCCGTTGGTG AAGACCGCCG TGCACGGCTG CGACCCCAAC TGGGGCCGGG TCGCCATGGC    8820

GATCGGCAAG TGCTCGGACG ACACCGACAT CGACCAGGAG CGGGTGACGA TCCGCTTCGG    8880

CGAGGTCGAG GTCTATCCGC CGAAGGCCCG GGCGACCAG GCCGACGACG CGCTGCGGGC    8940

CGCCGTCGCG GAGCATCTGC GGGGCGACGA GGTGGTCATC GGGATCGACC TCGCCATCGC    9000

GGACGGGGCC TTCACCGTCT ACGGCTGCGA CCTCACCGAG GGCTATGTCC GGCTGAACTC    9060

GGAGTACACC ACCTGATCCC CGGACAGGGA ACGGGCCGCC GCCCCGTTCC CTGTCCGCTC    9120

CCGTCCCGTG TGGTTATACC GACCGTTCCC CGGCTATGCG CACGGGACGG AGCGGCCCCC    9180

GCCGGGCCCC GCCCGGCCGC ACGATGAGGG GCGATGCAAG GTGACGAGGG CAGGAGGGAC    9240

ATGGAGACCA CTCGGTCGAC GACCGCGGAC GAGGGCTTCG ACGCCGGGGT ACGGGGAGTG    9300

GTCGCGCCGA CCGACGCCCC GGGCGGGACG CTGCGGCTGG TCCGCACGGA CGACTTCGAC    9360

TCGCTCGACC CCGGCAACAC GTACTACGCC TACACCTGGA ACTTCCTCCG GCTCATCGGC    9420

CGGACGCTGG TCACCTTCGA CACCGCGCCG GGCAAGGCG GCCAGCGGCT CGTGCCCGAC    9480

CTCGCCGAGT CGCTGGGCGA GTCCTCCGAG GACGGCCGGG TCTGGACCTA CCGGCTGCGC    9540
```

```
                                                        -continued

GAGGGCCTGC GCTACGAGGA CGGCACGCCG GTCGTCTCGG CCGACATCAA GCACGCCATC    9600

GCCCGCAGCA ACTACGGCAC CGATGTCCTG GGCGCCGGTC CGACCTACTT CCGCCACCTC    9660

CTGGGCACCG AGTACGGCGG CCCCTGGCGG GAGCCGGACG CCGACGGACC GGTGACGCTG    9720

GAGACCCCGG ACGAGCGGAC GCTGGTCTTC CGGCTGCGGG AGCCGTTCGC GGGGATGGAT    9780

CTGCTGGCGA CCATGCCGTC CACCACCCCC GTGCCGCGCG ACCGGGACAC CGGCGCCGAG    9840

TACCGGCTGC GGCCCGTGGC GACCGGCCCG TACCGGATCG TCTCGTACAC CCGGGGCGAG    9900

CTGGCCGTCC TGGAGCCCAA TCCGCACTGG GACCCCGAGA CCGACCCGGT GCGCGTCCAG    9960

CGCGCCTCCC GGATCGAGGT GCACCTCGGC AAGGACCCGC ACGAGGTGGA CCGCATGCTG   10020

CTGGCGGGCG AGGCCCATGT GGACCTCGCG GGCTTCGGTG TGCAGCCCGC GGCCCAGGAG   10080

CGCATCCTCG CCGAGCCGGA GCTGCGCGCG CACGCGGACA ACCCGCTGAC CGGCTTCACC   10140

TGGATCTACT GCCTGTCGAG CCGGATCGCC CCGTTCGACA ATGTGCACTG CCGGCGGGCC   10200

GTGCAGTTCG CCACCGACAA AGCGGCCATG CAGGAGGCGT ACGGCGGCGC GGTGGGCGGC   10260

GACATCGCGA CCACCCTGCT GCCCCCGACC CTCGACGGCT ACAAGCACTT CGACCGCTAC   10320

CCGGTCGGCC CCGAGGGCAC CGGCGACCTG GAGGCCGCCC GCGCCGAGCT GAAGCTGGCC   10380

GGGATGCCCG ACGGCTTCCG CACCAGGATC GCCGCCCGCA AGGACCGGCT CAAGGAGTAC   10440

CGGGCCGCCG AGGCGCTGGC CGCCGGGCTC GCCCGGGTCG GCATCGAGGC GGAGGTGCTG   10500

GACTTCCCGT CGGGCGACTA CTTCGACCGC TACGGCGGCT GCCCGGAGTA TCTGCGCGAG   10560

CACGGGATCG GGATCATCAT GTTCGGCTGG GGCGCCGACT TCCCCGACGG ATACGGCTTC   10620

CTCCAGCAGA TCACCGACGG GCGCGCGATC AAGGAGCGCG GCAACCAGAA CATGGGCGAG   10680

CTGGACGACC CGGAGATCAA CGCGCTGCTG GACGAGGGGG CGCAGTGCGC CGACCCGGCG   10740

CGGCGCGCGG AGATCTGGCA CCGCATCGAC CAGCTCACGA TGGACCACGC GGTCATCGTT   10800

CCGTATCTGT ACCCGCGGTC CCTGCTCTAC CGGCACCCGG ACACCCGCAA CGCCTTCGTC   10860

ACCGGCTCCT TCGGGATGTA CGACTACGTG GCGCTCGGCG CGAAGTGAGC ACGGGGTCCG   10920

GCCCCGGGAC CGTATGTCCC GGGGCCGGAC CCCGCCCGTT CCCCGCCCGG TCCGGTCCGG   10980

ACCCGGTCGC GGCCCGCTCA GCCGGACATC CGGGCCCCGG CCGCGACCCC GCGCCGGATC   11040

GGCCAGTGGC CCTGCGCCAG GGGCCGTTCC ACGCTGCGGC AGGCGAGAGC GGCCTCGCGG   11100

AACTCCGCCT CGTACAGCGC GAGCTGGCGC AGGAACTGCC GGGTCGGGCC GGTCAGGCTG   11160

GTCCCCGCGG GGCTGCGCAG CAGCAGCCGG GCGCCGAGGG ACTGCTCCAG CCGGTGAATC   11220

CGGCGGGTGA GCGCCGACTG GCTGATCGAC AGCACCGCCG CGGCCCGGTT GATGCTGCCG   11280

TGCCGGGCCA CGGCCTGGAG CAGATGGAGA TCGTCCACAT CCAGTTTGCG GCCCTCGGCC   11340

TGGCCGGGCA CGGAGCCCTG GTCGGGTCCC GCCCCGAAGC GGCGGGCGTC CGCGCCGGTG   11400

CGCTCCGCGT ACCACTGCGC CCACCAGGGC TCGTCCAGCA GGTCGCGGTG GTGTTCGGCG   11460

AAGCGCCGGA GCTGGACCTC GGCGATCAGC GCGGCCAGCC GTCCCGCCAG CGCCCGGGGC   11520

ACGATGGTGG GGTCGACGAG CAGACTCGTG GTGCGGCGCG GGCGCTCCGC CAGGGAGCGG   11580

CGCACCAGCG AGGGGTCCTG CACCGCCGGG TGGGTGGGCG AGCCGAGACC TATCGCGTCC   11640

CCGCGGCGCA GGATGCCCCG GGCAACCGAT GCCCCGTGA TGTGGAGCCG GGTGGGCGCG    11700

GTGAGCCCGG CCAGCTGGAA GACACGTGTC ACCAGGATCT CCGAGCCGGG TCCCGTCTCG   11760

GACACCCAGG TCTCGTCCCG CAGATCGGCG AGCGAGACCT CCCGCGGGC GGCCAGCGGA    11820

TGGTCCCGGG GCAGGATCAC CCACAGCGGG TCGTCCAGCA CCTCACAGGT GCGCACGGAC   11880

CGCTCCAGGC TGTGCCGGGG GGACTGGAGG CTCCAGGTGT AGGCCGCGTC CACCTGGTAG   11940
```

```
CCCGCCAGTT GGGCGGCGAC CTGGTGCGGG GCCTCGTGCC GGACCGACAG CAGCAGGTCC  12000
AGCGAGGCCG CCGCGTCCTC CACCACCTCG TCGAGCAGGG GTTCCGTGGA GACCAGCGAC  12060
AGCACCTCCG GGGCGTCCAC GGCCTCGGAG CCATGGCCGA AGATATGCGT CCGCGCGGCC  12120
AGGTCGACCT GGTGGAAGAA CCGCCGCCCG GCGACGAGGA TGCGGGAGCC CGCGGTGGTC  12180
AGCCGGGCCG TGTGGCGGCT CGCAGGGTC AGCGGGAGGC CGACGATCCG GTCCAGCCGG  12240
TCGAGTCTGC GCTCCACGGT GCCGTGCCGG ACACCCGTCC GCCGGGCCAC TTCCATGAGG  12300
TCTCCGCAGT GTCCCACCGC GTCCAGTAAA GACAGATCGC ATCGGCTGAC ACCAGCAGAC  12360
GTCGGTTCTG ACCCGAGAGA CAATGTCGGT TCCCTTTTCC GTCAAGGACT GTACCGCTGA  12420
ATTGTCCGAA GTGGCTCTTG AATTGCTTCG GAATCGATCC TAGGCAGCGC CGCTCTTCGG  12480
ATTCTCCTCG CCGGGAAGCG GAACGCGCCC GGCCGGATGG CGGGCGCGCT CCGGGCGCCG  12540
TCCCGGGAAC GGGGGACGGG GCACGGCACG GCCGGCCACC CGGTCCGGGC GCGCGGCGTG  12600
GACCTGGTCG GCGGACGGGT GTCAGACCTG GTCGGTGGGG CGTATGAAGA TCTCGTGGAC  12660
GGTCGCGTGG TGCGGCGCGG TCACGGCGTA GCGGACCGCC TCCGCGATGT CCTGGGCCTG  12720
GAGCTTGCGG ATCGGCTGA TCCGCTGCTC GTACATCTCC TTGGTGGCGG TGTGGGTGAT  12780
GTGGCCGCGC AGCTCCGTGT CGGTGGTGCC CGGCTCGATG ACGACGACCC GCACCCCGCG  12840
CTCGGTGACC TCCTGGCGCA GCGTCTCGCT GAACGCGTTC ACACCGAACT TCGTGGCCTG  12900
GTAGACGGCC GCGTTGCGGA CGTTCACCCG GCCCGCGATC GAGGACATCT GCACCACGGT  12960
GCCCTTGCTG CGCAGCAGAT GGGGAAGGGC CGCCCGGGTC ATGTACATCA GGCCCAGGAG  13020
ATTGGTGTCG ATCATCCGGG TCCAGTCGGT GGTGTCGGCG TCCTCCACCG GCCGAGCAG   13080
CATGATCCCG GCGTTGTTGA CGAGGATGTC GAGGCCGCCC AGCGCCTCGA CGGTGGAGGC  13140
GACGGCGGCG TCCACCCCCT GCCGGTCGGC GACGTCGAGT TCGAGGACAT GGACCTTCGC  13200
CCCGGCGGCG GTCAGCTCGT CACCCAGGGC GCGCAGCTTC TCGACCCGGC GCGCGGCGAT  13260
GGCCACGGCG GCGCCCTCGG CGGCCAGGGC GCGGGCCGTG GCCTCGCCGA TGCCCGAGCT  13320
CGCGCCCGTG ATGAGCGCGA CTTTCCCCTG GAGTGCGGAT GGCATCATTT CCTCCACATG  13380
GTGCTGCGAT CGTGGTGAGC GTATGAAGAA GGGGTGAGAC CTGCCGTGCC GGGGCGGGTT  13440
CCGTACGCCG GACCGTTGCG GTGGGCACGG CCGACCGGGT ACGGATGGCC GCAGTTCCCC  13500
GGGGAGTTCC CGGGGAATGG TGAATACCGC GGCGCTCTCC GATGGTCTTC GGAGGACACC  13560
CGGGGATTCA CCGGGAATCA GCGGCCGGAG TTCTCCCCGT CCACGGCAGA CGCTATCAGC  13620
GTCGCATTCC CCGGTGAATT CCCTTCGGTG GACCGGGTTA TGACTGTTTC CGCCGGGTTA  13680
TGCGCGCCGC CCCGGCGGAC CGGCCACCCG CCCGGGGGCT GCGGCAGATT GGGCGCCACG  13740
ACATGGCGCG AGCAGCGATC GGCGGTGGAT GATGAACGAG GCAGCGCCTC AGTCCGACCA  13800
GGTGGCACCG GCGTATCCGA TGCACCGGGT CTGCCCGGTC GACCCGCCGC CGCAACTGGC  13860
CGGGCTGCGG TCCAGAAGG CCGCGAGCCG GGTGACGCTG TGGGACGGCA GCCAGGTGTG   13920
GCTGGTGACC TCGCACGCCG GGCCCGGGC CGTCCTGGGC GACCGCCGCT TCACCGCGGT   13980
GACGAGCGCG CCCGGCTTCC CGATGCTGAC CCGCACCTCC CAACTGGTGC GCGCCAACCC  14040
GGAGTCGGCG TCGTTCATCC GCATGGACGA CCCGCAGCAC TCCCGGCTGC GCTCGATGCT  14100
CACCCGGGAC TTCCTGGCCC GCCGCGCCGA GGCGCTGCGC CCCGCGGTGC GGGAGCTGCT  14160
GGACGAGATC CTGGGCGGGC TGGTGAAGGG GGAGCGGCCG GTCGACCTGG TCGCCGGACT  14220
GACGATCCCG GTGCCCTCGC GGGTCATCAC CCTGCTCTTC GGCGCCGGTG ACGACCGCCG  14280
GGAGTTCATC GAGGACCGCA GCGCGGTCCT CATCGACCGC GGCTACACCC CGGAGCAGGT  14340
```

```
CGCCAAGGCC CGGGACGAAC TCGACGGCTA TCTGCGGGAG CTGGTCGAGG AGCGGATCGA    14400

GAACCCGGGC ACCGACCTGA TCAGCCGGCT CGTCATCGAC CAGGTGCGGC CGGGGCATCT    14460

GCGGGTCGAG GAGATGGTCC CGATGTGCCG GCTGCTGCTG GTGGCCGGTC ACGGCACCAC    14520

CACCAGCCAG GCGAGCCTGA GCCTGCTCAG CCTGCTCACC GACCCGGAGC TGGCCGGGCG    14580

CCTCACCGAG GACCCGGCCC TGCTGCCCAA GGCGGTCGAG GAGCTGCTGC GCTTCCACTC    14640

CATCGTGCAG AACGGGCTGG CCCGTGCCGC GGTGGAGGAC GTCCAGCTCG ACGATGTGCT    14700

CATCCGGGCG GGCGAGGGCG TGGTGCTGTC GCTGTCGGCG GGCAACCGGG ACGAGACGGT    14760

CTTCCCCGAC CCGGACCGGG TGGACGTGGA CCGCGACGCC CGCCGCCATC TCGCCTTCGG    14820

CCACGGCATG CACCAGTGCC TGGGCCAGTG GCTGGCCCGG GTGGAGCTGG AGGAGATCCT    14880

CGCCGCGGTG CTGCGCTGGA TGCCCGGTGC CCGGCTCGCG GTGCCCTTCG AGGAGCTGGA    14940

CTTCCGTCAT GAGGTGTCCA GTTACGGCCT CGGCGCCCTC CCGGTGACCT GGTGAGCGGC    15000

GTGGAGCGGC TGACCGTCGT CCTCGACGCG TCGGCCTGCT GCGCGATGGG GCGCTGCGCG    15060

GCCACGGCCC CCGAGATCT                                                15079
```

(2) INFORMATION FOR SEQ ID NO: 2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO: 2:

```
TACGCCCAGA TCCCCACCTT CATG                                                24
```

(2) INFORMATION FOR SEQ ID NO: 3:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 3:

```
Met Thr His Ser Asp Asn Tyr Gly Asp Asp Pro Gln Gly Arg Arg
 1               5                  10                  15

Arg Ser Arg Gly Arg Ala Ala Thr Ala Val Val Ala Gly Leu Ala Val
                20                  25                  30

Thr Val Gly Leu Gly Tyr Trp Gly Tyr Thr Ser Leu Val Ala Asp Glu
            35                  40                  45

Lys Asp Ser Gly Asp Pro Glu Val Glu Ala Ala Gly Gln Phe Asp
 50                  55                  60

Thr Phe Leu Gly Ala Trp Glu Lys Gly Asp Ala Pro Thr Ala Ala Gly
 65                  70                  75                  80

Leu Thr Asp Thr Pro Asp Asn Ala Glu Ser Leu Ile Lys Ser Val Met
                85                  90                  95

Thr Asn Leu Lys Pro Thr Lys Thr Glu Ile Thr Ala Lys Thr Gly Glu
               100                 105                 110

Lys Asn Pro Glu Gly Glu Val Glu Ile Pro Phe Thr Val Arg Met Thr
           115                 120                 125
```

-continued

```
Leu Pro Gly Ala Gly Glu Tyr Ala Trp Asp Ser Thr Ala Lys Val Val
    130                 135                 140
Gly Gly Gly Lys Glu Trp Lys Val Ala Phe Asn Thr Glu Met Ile His
145                 150                 155                 160
Pro Gln Met Val Pro Gly Gln Thr Leu Ala Leu Lys Ser Arg Glu Arg
                165                 170                 175
Ala Asp Ile Leu Asp Ala Asn Gly Asn Val Leu Gln Ala Ala Ser Ile
            180                 185                 190
Ile Gly Ala Val Asp Pro Arg Thr Gly Lys Gly Ser Ala Gly Leu Gln
        195                 200                 205
Ser Arg Tyr Asp Lys Gln Leu Thr Gly Gly Ser Gly Ala Ala Arg Ser
    210                 215                 220
Val Val Ile Leu Asp Arg Glu Ser Gly Gln Val Val Lys Lys Leu Thr
225                 230                 235                 240
Gly Leu Lys Asp Thr Glu Gly Lys Pro Val Lys Thr Thr Ile Asp Pro
                245                 250                 255
Arg Val Gln Ser Ala Ala Ala Ala Leu Glu Gly Ser Lys Lys Asn
            260                 265                 270
Ala Ala Ile Val Ala Val Asp Pro Ala Thr Gly Asn Ile Leu Ala Ala
        275                 280                 285
Ala Asn Val Pro Ser Gly Met Asn Arg Ala Leu Glu Gly Arg Tyr Pro
    290                 295                 300
Pro Gly Ser Thr Phe Lys Val Val Thr Thr Ala Ala Leu Leu Gln Gln
305                 310                 315                 320
Gly Met Asn Pro Glu Glu Arg Ala Asp Cys Pro Lys Phe Ala His Val
                325                 330                 335
Asn Gly Gln Ser Phe Glu Asn Gln Asp Gln Phe Thr Leu Pro Ala Gly
            340                 345                 350
Ser Thr Phe Arg Asp Ser Phe Ala His Ser Cys Asn Thr Phe Phe Val
        355                 360                 365
Asn Ser Arg Ser Lys Leu Ser Glu Ser Ser Leu Lys Gln Ala Ala Glu
    370                 375                 380
Ala Phe Gly Ile Gly Gly Thr Trp Asp Val Gly Ala Ser Thr Phe Asp
385                 390                 395                 400
Gly Ser Val Pro Val Ser Asn Ser Glu Asn Asp Lys Ala Ala Ser Thr
                405                 410                 415
Ile Gly Gln Ala Arg Val Glu Ala Ser Pro Leu Val Met Ala Ser Ile
            420                 425                 430
Ala Ala Thr Val Lys Gln Gly Glu Phe Lys Gln Pro Val Leu Val Pro
        435                 440                 445
Asp Ala Val Lys Lys Pro His Gln Ala Pro Arg Met Ala Pro Gly Ile
    450                 455                 460
Val Asp Ser Leu Arg Ser Met Met Arg Ser Thr Val Thr Asp Gly Ala
465                 470                 475                 480
Gly Asp Ala Leu Arg Gly Leu Gly Gly Gln Pro His Ala Lys Thr Gly
                485                 490                 495
Thr Ala Glu Phe Gly Thr Glu Lys Pro Pro Lys Thr His Ala Trp Met
            500                 505                 510
Ile Gly Tyr Gln Gly Asp Arg Asn Ile Ala Trp Ser Val Leu Leu Glu
        515                 520                 525
```

```
Asp Gly Gly Ser Gly Gly Ala Asp Ala Gly Pro Val Ala Ala Lys Phe
    530                 535                 540

Leu Ser Asn Leu Ala Ala Gly Glx
545                 550

(2) INFORMATION FOR SEQ ID NO: 4:

(i) SEQUENCE CHARACTERISTICS:
        (A) LENGTH: 574 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4:

Met Ser Arg Val Ser Thr Ala Pro Ser Gly Lys Pro Thr Ala Ala His
1               5                   10                  15

Ala Leu Leu Ser Arg Leu Arg Asp His Gly Val Gly Lys Val Phe Gly
                20                  25                  30

Val Val Gly Arg Glu Ala Ala Ser Ile Leu Phe Asp Glu Val Glu Gly
            35                  40                  45

Ile Asp Phe Val Leu Thr Arg His Glu Phe Thr Ala Gly Val Ala Ala
    50                  55                  60

Asp Val Leu Ala Arg Ile Thr Gly Arg Pro Gln Ala Cys Trp Ala Thr
65                  70                  75                  80

Leu Gly Pro Gly Met Thr Asn Leu Ser Thr Gly Ile Ala Thr Ser Val
                85                  90                  95

Leu Asp Arg Ser Pro Val Ile Ala Leu Ala Ala Gln Ser Glu Ser His
                100                 105                 110

Asp Ile Phe Pro Asn Asp Thr His Gln Cys Leu Asp Ser Val Ala Ile
            115                 120                 125

Val Ala Pro Met Ser Lys Tyr Ala Val Glu Leu Gln Arg Pro His Glu
        130                 135                 140

Ile Thr Asp Leu Val Asp Ser Ala Val Asn Ala Ala Met Thr Glu Pro
145                 150                 155                 160

Val Gly Pro Ser Phe Ile Ser Leu Pro Val Asp Leu Leu Gly Ser Ser
                165                 170                 175

Glu Gly Ile Asp Thr Thr Val Pro Asn Pro Ala Asn Thr Pro Ala
                180                 185                 190

Lys Pro Val Gly Val Val Ala Asp Gly Trp Gln Lys Ala Ala Asp Gln
            195                 200                 205

Ala Ala Ala Leu Leu Ala Glu Ala Lys His Pro Val Leu Val Val Gly
        210                 215                 220

Ala Ala Ile Arg Ser Gly Ala Val Pro Ala Ile Arg Ala Ile Ala
225                 230                 235                 240

Glu Arg Leu Asn Ile Pro Val Ile Thr Thr Tyr Ile Ala Lys Gly Val
                245                 250                 255

Leu Pro Val Gly His Glu Leu Asn Tyr Gly Ala Val Thr Gly Tyr Met
                260                 265                 270

Asp Gly Ile Leu Asn Phe Pro Ala Leu Gln Thr Met Phe Ala Pro Val
            275                 280                 285

Asp Leu Val Leu Thr Val Gly Tyr Asp Tyr Ala Glu Asp Leu Arg Pro
        290                 295                 300

Ser Met Trp Gln Lys Gly Ile Glu Lys Thr Val Arg Ile Ser Pro
305                 310                 315                 320
```

```
Thr Val Asn Pro Ile Pro Arg Val Tyr Arg Pro Asp Val Asp Val Val
                325                 330                 335

Thr Asp Val Leu Ala Phe Val Glu His Phe Glu Thr Ala Thr Ala Ser
            340                 345                 350

Phe Gly Ala Lys Gln Arg His Asp Ile Glu Pro Leu Arg Ala Arg Ile
        355                 360                 365

Ala Glu Phe Leu Ala Asp Pro Glu Thr Tyr Glu Asp Gly Met Arg Val
    370                 375                 380

His Gln Val Ile Asp Ser Met Asn Thr Val Met Glu Glu Ala Ala Glu
385                 390                 395                 400

Pro Gly Glu Gly Thr Ile Val Ser Asp Ile Gly Phe Arg His Tyr
                405                 410                 415

Gly Val Leu Phe Ala Arg Ala Asp Gln Pro Phe Gly Phe Leu Thr Ser
            420                 425                 430

Ala Gly Cys Ser Ser Phe Gly Tyr Gly Ile Pro Ala Ala Ile Gly Ala
        435                 440                 445

Gln Met Ala Arg Pro Asp Gln Pro Thr Phe Leu Ile Ala Gly Asp Gly
    450                 455                 460

Gly Phe His Ser Asn Ser Ser Asp Leu Glu Thr Ile Ala Arg Leu Asn
465                 470                 475                 480

Leu Pro Ile Val Thr Val Val Asn Asn Asp Thr Asn Gly Leu Ile
                485                 490                 495

Glu Leu Tyr Gln Asn Ile Gly His His Arg Ser His Asp Pro Ala Val
            500                 505                 510

Lys Phe Gly Gly Val Asp Phe Val Ala Leu Ala Glu Ala Asn Gly Val
        515                 520                 525

Asp Ala Thr Arg Ala Thr Asn Arg Glu Glu Leu Leu Ala Ala Leu Arg
    530                 535                 540

Lys Gly Ala Glu Leu Gly Arg Pro Phe Leu Ile Glu Val Pro Val Asn
545                 550                 555                 560

Tyr Asp Phe Gln Pro Gly Gly Phe Gly Ala Leu Ser Ile Glx
                565                 570
```

(2) INFORMATION FOR SEQ ID NO: 5:

(i) SEQUENCE CHARACTERISTICS:
        (A) LENGTH: 514 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 5:

```
Met Gly Ala Pro Val Leu Pro Ala Ala Phe Gly Phe Leu Ala Ser Ala
1               5                   10                  15

Arg Thr Gly Gly Gly Arg Ala Pro Gly Pro Val Phe Ala Thr Arg Gly
            20                  25                  30

Ser His Thr Asp Ile Asp Thr Pro Gln Gly Glu Arg Ser Leu Ala Ala
        35                  40                  45

Thr Leu Val His Ala Pro Ser Val Ala Pro Asp Arg Ala Val Ala Arg
    50                  55                  60

Ser Leu Thr Gly Ala Pro Thr Thr Ala Val Leu Ala Gly Glu Ile Tyr
65                  70                  75                  80

Asn Arg Asp Glu Leu Leu Ser Val Leu Pro Ala Gly Pro Ala Pro Glu
                85                  90                  95
```

```
Gly Asp Ala Glu Leu Val Leu Arg Leu Leu Glu Arg Tyr Asp Leu His
            100                 105                 110
Ala Phe Arg Leu Val Asn Gly Arg Phe Ala Thr Val Val Arg Thr Gly
        115                 120                 125
Asp Arg Val Leu Leu Ala Thr Asp His Ala Gly Ser Val Pro Leu Tyr
    130                 135                 140
Thr Cys Val Ala Pro Gly Glu Val Arg Ala Ser Thr Glu Ala Lys Ala
145                 150                 155                 160
Leu Ala Ala His Arg Asp Pro Lys Gly Phe Pro Leu Ala Asp Ala Arg
                165                 170                 175
Arg Val Ala Gly Leu Thr Gly Val Tyr Gln Val Pro Ala Gly Ala Val
            180                 185                 190
Met Asp Ile Asp Leu Gly Ser Gly Thr Ala Val Thr His Arg Thr Trp
        195                 200                 205
Thr Pro Gly Leu Ser Arg Arg Ile Leu Pro Glu Gly Glu Ala Val Ala
    210                 215                 220
Ala Val Arg Ala Ala Leu Glu Lys Ala Val Ala Gln Arg Val Thr Pro
225                 230                 235                 240
Gly Asp Thr Pro Leu Val Val Leu Ser Gly Gly Ile Asp Ser Ser Gly
                245                 250                 255
Val Ala Ala Cys Ala His Arg Ala Ala Gly Glu Leu Asp Thr Val Ser
            260                 265                 270
Met Gly Thr Asp Thr Ser Asn Glu Phe Arg Glu Ala Arg Ala Val Val
        275                 280                 285
Asp His Leu Arg Thr Arg His Arg Glu Ile Thr Ile Pro Thr Thr Glu
    290                 295                 300
Leu Leu Ala Gln Leu Pro Tyr Ala Val Trp Ala Ser Glu Ser Val Asp
305                 310                 315                 320
Pro Asp Ile Ile Glu Tyr Leu Leu Pro Leu Thr Ala Leu Tyr Arg Ala
                325                 330                 335
Leu Asp Gly Pro Glu Arg Arg Ile Leu Thr Gly Tyr Gly Ala Asp Ile
            340                 345                 350
Pro Leu Gly Gly Met His Arg Glu Asp Arg Leu Pro Ala Leu Asp Thr
        355                 360                 365
Val Leu Ala His Asp Met Ala Thr Phe Asp Gly Leu Asn Glu Met Ser
    370                 375                 380
Pro Val Leu Ser Thr Leu Ala Gly His Trp Thr Thr His Pro Tyr Trp
385                 390                 395                 400
Asp Arg Glu Val Leu Asp Leu Val Ser Leu Glu Ala Gly Leu Lys
                405                 410                 415
Arg Arg His Gly Arg Asp Lys Trp Val Leu Arg Ala Ala Met Ala Asp
            420                 425                 430
Ala Leu Pro Ala Glu Thr Val Asn Arg Pro Lys Leu Gly Val His Glu
        435                 440                 445
Gly Ser Gly Thr Thr Ser Ser Phe Ser Arg Leu Leu Leu Asp His Gly
    450                 455                 460
Val Ala Glu Asp Arg Val His Glu Ala Lys Arg Gln Val Val Arg Glu
465                 470                 475                 480
Leu Phe Asp Leu Thr Val Gly Gly Arg His Pro Ser Glu Val Asp
                485                 490                 495
Thr Asp Asp Val Val Arg Ser Val Ala Asp Arg Thr Ala Arg Gly Ala
            500                 505                 510
Ala Glx
```

(2) INFORMATION FOR SEQ ID NO: 6:

(i) SEQUENCE CHARACTERISTICS:
        (A) LENGTH: 314 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6:

```
Val Glu Arg Ile Asp Ser His Val Ser Pro Arg Tyr Ala Gln Ile Pro
 1               5                  10                  15

Thr Phe Met Arg Leu Pro His Asp Pro Gln Pro Arg Gly Tyr Asp Val
             20                  25                  30

Val Val Ile Gly Ala Pro Tyr Asp Gly Gly Thr Ser Tyr Arg Pro Gly
         35                  40                  45

Ala Arg Phe Gly Pro Gln Ala Ile Arg Ser Glu Ser Gly Leu Ile His
     50                  55                  60

Gly Val Gly Ile Asp Arg Gly Pro Gly Thr Phe Asp Leu Ile Asn Cys
 65                  70                  75                  80

Val Asp Ala Gly Asp Ile Asn Leu Thr Pro Phe Asp Met Asn Ile Ala
                 85                  90                  95

Ile Asp Thr Ala Gln Ser His Leu Ser Gly Leu Leu Lys Ala Asn Ala
            100                 105                 110

Ala Phe Leu Met Ile Gly Gly Asp His Ser Leu Thr Val Ala Ala Leu
        115                 120                 125

Arg Ala Val Ala Glu Gln His Gly Pro Leu Ala Val Val His Leu Asp
130                 135                 140

Ala His Ser Asp Thr Asn Pro Ala Phe Tyr Gly Gly Arg Tyr His His
145                 150                 155                 160

Gly Thr Pro Phe Arg His Gly Ile Asp Glu Lys Leu Ile Asp Pro Ala
                165                 170                 175

Ala Met Val Gln Ile Gly Ile Arg Gly His Asn Pro Lys Pro Asp Ser
            180                 185                 190

Leu Asp Tyr Ala Arg Gly His Gly Val Arg Val Thr Ala Asp Glu
        195                 200                 205

Phe Gly Glu Leu Gly Val Gly Gly Thr Ala Asp Leu Ile Arg Glu Lys
    210                 215                 220

Val Gly Gln Arg Pro Val Tyr Val Ser Val Asp Ile Asp Val Val Asp
225                 230                 235                 240

Pro Ala Phe Ala Pro Gly Thr Gly Thr Pro Ala Pro Gly Gly Leu Leu
                245                 250                 255

Ser Arg Glu Val Leu Ala Leu Leu Arg Cys Val Gly Asp Leu Lys Pro
            260                 265                 270

Val Gly Phe Asp Val Met Glu Val Ser Pro Leu Tyr Asp His Gly Gly
        275                 280                 285

Ile Thr Ser Ile Leu Ala Thr Glu Ile Gly Ala Glu Leu Leu Tyr Gln
    290                 295                 300

Tyr Ala Arg Ala His Arg Thr Gln Leu Glx
305                 310
```

(2) INFORMATION FOR SEQ ID NO: 7:

(i) SEQUENCE CHARACTERISTICS:
        (A) LENGTH: 326 amino acids
        (B) TYPE: amino acid (C) STRANDEDNESS: single
            (D) TOPOLOGY: linear (ii) MOLECULE TYPE: protein (xi) SEQUENCE DESCRIPTION: SEQ ID NO: 7:

Met Ala Ser Pro Ile Val Asp Cys Thr Pro Tyr Arg Asp Glu Leu Leu
1               5                  10                  15

Ala Leu Ala Ser Glu Leu Pro Glu Val Pro Arg Ala Asp Leu His Gly
            20                  25                  30

Phe Leu Asp Glu Ala Lys Thr Leu Ala Ala Arg Leu Pro Glu Gly Leu
        35                  40                  45

Ala Ala Ala Leu Asp Thr Phe Asn Ala Val Gly Ser Glu Asp Gly Tyr
50                  55                  60

Leu Leu Leu Arg Gly Leu Pro Val Asp Asp Ser Glu Leu Pro Glu Thr
65                  70                  75                  80

Pro Thr Ser Thr Pro Ala Pro Leu Asp Arg Lys Arg Leu Val Met Glu
                85                  90                  95

Ala Met Leu Ala Leu Ala Gly Arg Arg Leu Gly Leu His Thr Gly Tyr
            100                 105                 110

Gln Glu Leu Arg Ser Gly Thr Val Tyr His Asp Val Tyr Pro Ser Pro
        115                 120                 125

Gly Ala His Tyr Leu Ser Ser Glu Thr Ser Glu Thr Leu Leu Glu Phe
130                 135                 140

His Thr Glu Met Ala Tyr His Ile Leu Gln Pro Asn Tyr Val Met Leu
145                 150                 155                 160

Ala Cys Ser Arg Ala Asp His Glu Asn Arg Ala Glu Thr Leu Val Gly
                165                 170                 175

Ser Val Arg Lys Ala Leu Pro Leu Leu Asp Glu Lys Thr Arg Ala Arg
            180                 185                 190

Leu Phe Asp Arg Lys Val Pro Cys Cys Val Asp Val Ala Phe Arg Gly
        195                 200                 205

Gly Val Asp Asp Pro Gly Ala Ile Ala Asn Val Lys Pro Leu Tyr Gly
210                 215                 220

Asp Ala Asn Asp Pro Phe Leu Gly Tyr Asp Arg Glu Leu Leu Ala Pro
225                 230                 235                 240

Glu Asp Pro Ala Asp Lys Glu Ala Val Ala His Leu Ser Gln Ala Leu
                245                 250                 255

Asp Asp Val Thr Val Gly Val Lys Leu Val Pro Gly Asp Val Leu Ile
            260                 265                 270

Ile Asp Asn Phe Arg Thr Thr His Ala Arg Thr Pro Phe Ser Pro Arg
        275                 280                 285

Trp Asp Gly Lys Asp Arg Trp Leu His Arg Val Tyr Ile Arg Thr Asp
290                 295                 300

Arg Asn Gly Gln Leu Ser Gly Gly Glu Arg Ala Gly Asp Thr Ile Ser
305                 310                 315                 320

Phe Ser Pro Arg Arg Glx
                325

(2) INFORMATION FOR SEQ ID NO: 8:

(i) SEQUENCE CHARACTERISTICS:
        (A) LENGTH: 394 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8:

Met Ser Asp Ser Thr Pro Lys Thr Pro Arg Gly Phe Val Val His Thr
1               5                   10                  15

Ala Pro Val Gly Leu Ala Asp Asp Gly Arg Asp Phe Thr Val Leu
            20                  25                  30

Ala Ser Thr Ala Pro Ala Thr Val Ser Ala Val Phe Thr Arg Ser Arg
        35                  40                  45

Phe Ala Gly Pro Ser Val Val Leu Cys Arg Glu Ala Val Ala Asp Gly
    50                  55                  60

Gln Ala Arg Gly Val Val Val Leu Ala Arg Asn Ala Asn Val Ala Thr
65                  70                  75                  80

Gly Leu Glu Gly Glu Glu Asn Ala Arg Glu Val Arg Glu Ala Val Ala
                85                  90                  95

Arg Ala Leu Gly Leu Pro Glu Gly Glu Met Leu Ile Ala Ser Thr Gly
                100                 105                 110

Val Ile Gly Arg Gln Tyr Pro Met Glu Ser Ile Arg Glu His Leu Lys
            115                 120                 125

Thr Leu Glu Trp Pro Ala Gly Glu Gly Phe Asp Arg Ala Ala Arg
130                 135                 140

Ala Ile Met Thr Thr Asp Thr Arg Pro Lys Glu Val Arg Val Ser Val
145                 150                 155                 160

Gly Gly Ala Thr Leu Val Gly Ile Ala Lys Gly Val Gly Met Leu Glu
                165                 170                 175

Pro Asp Met Ala Thr Leu Leu Thr Phe Phe Ala Thr Asp Ala Arg Leu
            180                 185                 190

Asp Pro Ala Glu Gln Asp Arg Leu Phe Arg Arg Val Met Asp Arg Thr
        195                 200                 205

Phe Asn Ala Val Ser Ile Asp Thr Asp Thr Ser Thr Ser Asp Thr Ala
    210                 215                 220

Val Leu Phe Ala Asn Gly Leu Ala Gly Glu Val Asp Ala Gly Glu Phe
225                 230                 235                 240

Glu Glu Ala Leu His Thr Ala Ala Leu Ala Leu Val Lys Asp Ile Ala
                245                 250                 255

Ser Asp Gly Glu Gly Ala Ala Lys Leu Ile Glu Val Gln Val Thr Gly
            260                 265                 270

Ala Arg Asp Asp Ala Gln Ala Lys Arg Val Gly Lys Thr Val Val Asn
        275                 280                 285

Ser Pro Leu Val Lys Thr Ala His Gly Cys Asp Pro Asn Trp Gly
    290                 295                 300

Arg Val Ala Met Ala Ile Gly Lys Cys Ser Asp Thr Asp Ile Asp
305                 310                 315                 320

Gln Glu Arg Val Thr Ile Arg Phe Gly Glu Val Glu Val Tyr Pro Pro
                325                 330                 335

Lys Ala Arg Gly Asp Gln Ala Asp Ala Leu Arg Ala Ala Val Ala
            340                 345                 350

Glu His Leu Arg Gly Asp Glu Val Val Ile Gly Ile Asp Leu Ala Ile
        355                 360                 365

Ala Asp Gly Ala Phe Thr Val Tyr Gly Cys Asp Leu Thr Glu Gly Tyr
    370                 375                 380

Val Arg Leu Asn Ser Glu Tyr Thr Thr Glx
385                 390

(2) INFORMATION FOR SEQ ID NO: 9:

(i) SEQUENCE CHARACTERISTICS:
        (A) LENGTH: 556 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 9:

```
Met Glu Thr Thr Arg Ser Thr Thr Ala Asp Glu Gly Phe Asp Ala Gly
  1               5                  10                  15

Val Arg Gly Val Val Ala Pro Thr Asp Ala Pro Gly Gly Thr Leu Arg
             20                  25                  30

Leu Val Arg Thr Asp Asp Phe Asp Ser Leu Asp Pro Gly Asn Thr Tyr
         35                  40                  45

Tyr Ala Tyr Thr Trp Asn Phe Leu Arg Leu Ile Gly Arg Thr Leu Val
     50                  55                  60

Thr Phe Asp Thr Ala Pro Gly Lys Ala Gly Gln Arg Leu Val Pro Asp
 65                  70                  75                  80

Leu Ala Glu Ser Leu Gly Glu Ser Ser Glu Asp Gly Arg Val Trp Thr
                 85                  90                  95

Tyr Arg Leu Arg Glu Gly Leu Arg Tyr Glu Asp Gly Thr Pro Val Val
                100                 105                 110

Ser Ala Asp Ile Lys His Ala Ile Ala Arg Ser Asn Tyr Gly Thr Asp
            115                 120                 125

Val Leu Gly Ala Gly Pro Thr Tyr Phe Arg His Leu Leu Gly Thr Glu
        130                 135                 140

Tyr Gly Gly Pro Trp Arg Glu Pro Asp Ala Asp Gly Pro Val Thr Leu
145                 150                 155                 160

Glu Thr Pro Asp Glu Arg Thr Leu Val Phe Arg Leu Arg Glu Pro Phe
                165                 170                 175

Ala Gly Met Asp Leu Leu Ala Thr Met Pro Ser Thr Thr Pro Val Pro
            180                 185                 190

Arg Asp Arg Asp Thr Gly Ala Glu Tyr Arg Leu Arg Pro Val Ala Thr
        195                 200                 205

Gly Pro Tyr Arg Ile Val Ser Tyr Thr Arg Gly Glu Leu Ala Val Leu
    210                 215                 220

Glu Pro Asn Pro His Trp Asp Pro Glu Thr Asp Pro Val Arg Val Gln
225                 230                 235                 240

Arg Ala Ser Arg Ile Glu Val His Leu Gly Lys Asp Pro His Glu Val
                245                 250                 255

Asp Arg Met Leu Leu Ala Gly Glu Ala His Val Asp Leu Ala Gly Phe
            260                 265                 270

Gly Val Gln Pro Ala Ala Gln Glu Arg Ile Leu Ala Glu Pro Glu Leu
        275                 280                 285

Arg Ala His Ala Asp Asn Pro Leu Thr Gly Phe Thr Trp Ile Tyr Cys
    290                 295                 300

Leu Ser Ser Arg Ile Ala Pro Phe Asp Asn Val His Cys Arg Arg Ala
305                 310                 315                 320

Val Gln Phe Ala Thr Asp Lys Ala Ala Met Gln Glu Ala Tyr Gly Gly
                325                 330                 335

Ala Val Gly Gly Asp Ile Ala Thr Thr Leu Leu Pro Pro Thr Leu Asp
            340                 345                 350
```

-continued

```
Gly Tyr Lys His Phe Asp Arg Tyr Pro Val Gly Pro Glu Gly Thr Gly
        355                 360                 365

Asp Leu Glu Ala Ala Arg Ala Glu Leu Lys Leu Ala Gly Met Pro Asp
370                 375                 380

Gly Phe Arg Thr Arg Ile Ala Ala Arg Lys Asp Arg Leu Lys Glu Tyr
385                 390                 395                 400

Arg Ala Ala Glu Ala Leu Ala Ala Gly Leu Ala Arg Val Gly Ile Glu
                405                 410                 415

Ala Glu Val Leu Asp Phe Pro Ser Gly Asp Tyr Phe Asp Arg Tyr Gly
                420                 425                 430

Gly Cys Pro Glu Tyr Leu Arg Glu His Gly Ile Gly Ile Ile Met Phe
            435                 440                 445

Gly Trp Gly Ala Asp Phe Pro Asp Gly Tyr Gly Phe Leu Gln Gln Ile
        450                 455                 460

Thr Asp Gly Arg Ala Ile Lys Glu Arg Gly Asn Gln Asn Met Gly Glu
465                 470                 475                 480

Leu Asp Asp Pro Glu Ile Asn Ala Leu Leu Asp Glu Gly Ala Gln Cys
                485                 490                 495

Ala Asp Pro Ala Arg Arg Ala Glu Ile Trp His Arg Ile Asp Gln Leu
            500                 505                 510

Thr Met Asp His Ala Val Ile Val Pro Tyr Leu Tyr Pro Arg Ser Leu
        515                 520                 525

Leu Tyr Arg His Pro Asp Thr Arg Asn Ala Phe Val Thr Gly Ser Phe
530                 535                 540

Gly Met Tyr Asp Tyr Val Ala Leu Gly Ala Lys Glx
545                 550                 555
```

(2) INFORMATION FOR SEQ ID NO: 10:

(i) SEQUENCE CHARACTERISTICS:
        (A) LENGTH: 433 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10:

```
Met Glu Val Ala Arg Arg Thr Gly Val Arg His Gly Thr Val Glu Arg
1               5                   10                  15

Arg Leu Asp Arg Leu Asp Arg Ile Val Gly Leu Pro Leu Thr Leu Arg
            20                  25                  30

Ser Arg His Thr Ala Arg Leu Thr Thr Ala Gly Ser Arg Ile Leu Val
        35                  40                  45

Ala Gly Arg Arg Phe Phe His Gln Val Asp Leu Ala Ala Arg Thr His
    50                  55                  60

Ile Phe Gly His Gly Ser Glu Ala Val Asp Ala Pro Glu Val Leu Ser
65                  70                  75                  80

Leu Val Ser Thr Glu Pro Leu Leu Asp Glu Val Val Glu Asp Ala Ala
                85                  90                  95

Ala Ser Leu Asp Leu Leu Leu Ser Val Arg His Glu Ala Pro His Gln
                100                 105                 110

Val Ala Ala Gln Leu Ala Gly Tyr Gln Val Asp Ala Ala Tyr Thr Trp
            115                 120                 125

Ser Leu Gln Ser Pro Arg His Ser Leu Glu Arg Ser Val Arg Thr Cys
        130                 135                 140
```

```
Glu Val Leu Asp Asp Pro Leu Trp Val Ile Leu Pro Arg Asp His Pro
145                 150                 155                 160

Leu Ala Ala Arg Arg Glu Val Ser Leu Ala Asp Leu Arg Asp Glu Thr
                165                 170                 175

Trp Val Ser Glu Thr Gly Pro Gly Ser Glu Ile Leu Val Thr Arg Val
            180                 185                 190

Phe Gln Leu Ala Gly Leu Thr Ala Pro Thr Arg Leu His Ile Thr Gly
        195                 200                 205

Ala Ser Val Ala Arg Gly Ile Leu Arg Arg Gly Asp Ala Ile Gly Leu
    210                 215                 220

Gly Ser Pro Thr His Pro Ala Val Gln Asp Pro Ser Leu Val Arg Arg
225                 230                 235                 240

Ser Leu Ala Glu Arg Pro Arg Arg Thr Thr Ser Leu Leu Val Asp Pro
                245                 250                 255

Thr Ile Val Pro Arg Ala Leu Ala Gly Arg Leu Ala Leu Leu Ile Ala
            260                 265                 270

Glu Val Gln Leu Arg Arg Phe Ala Glu His His Arg Asp Leu Leu Asp
        275                 280                 285

Glu Pro Trp Trp Ala Gln Trp Tyr Ala Glu Arg Thr Gly Ala Asp Ala
    290                 295                 300

Arg Arg Phe Gly Ala Gly Pro Asp Gln Gly Ser Val Pro Gly Gln Ala
305                 310                 315                 320

Glu Gly Arg Lys Leu Asp Val Asp Asp Leu His Leu Leu Gln Ala Val
                325                 330                 335

Ala Arg His Gly Ser Ile Asn Arg Ala Ala Val Leu Ser Ile Ser
            340                 345                 350

Gln Ser Ala Leu Thr Arg Arg Ile His Arg Leu Glu Gln Ser Leu Gly
        355                 360                 365

Ala Arg Leu Leu Leu Arg Ser Pro Arg Gly Thr Ser Leu Thr Gly Pro
    370                 375                 380

Thr Arg Gln Phe Leu Arg Gln Leu Ala Leu Tyr Glu Ala Glu Phe Arg
385                 390                 395                 400

Glu Ala Ala Leu Ala Cys Arg Ser Val Glu Arg Pro Leu Ala Gln Gly
                405                 410                 415

His Trp Pro Ile Arg Arg Gly Val Ala Ala Gly Ala Arg Met Ser Gly
            420                 425                 430

Glx
```

(2) INFORMATION FOR SEQ ID NO: 11:

(i) SEQUENCE CHARACTERISTICS:
        (A) LENGTH: 248 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 11:

```
Met Pro Ser Ala Leu Gln Gly Lys Val Ala Leu Ile Thr Gly Ala Ser
1               5                   10                  15

Ser Gly Ile Gly Glu Ala Thr Ala Arg Ala Leu Ala Ala Glu Gly Ala
            20                  25                  30

Ala Val Ala Ile Ala Ala Arg Arg Val Glu Lys Leu Arg Ala Leu Gly
        35                  40                  45
```

-continued

```
Asp Glu Leu Thr Ala Ala Gly Ala Lys Val His Val Leu Glu Leu Asp
         50                  55                  60
Val Ala Asp Arg Gln Gly Val Asp Ala Val Ala Ser Thr Val Glu
 65                  70                  75                  80
Ala Leu Gly Gly Leu Asp Ile Leu Val Asn Asn Ala Gly Ile Met Leu
                     85                  90                  95
Leu Gly Pro Val Glu Asp Ala Asp Thr Thr Asp Trp Thr Arg Met Ile
                100                 105                 110
Asp Thr Asn Leu Leu Gly Leu Met Tyr Met Thr Arg Ala Ala Leu Pro
                115                 120                 125
His Leu Leu Arg Ser Lys Gly Thr Val Val Gln Met Ser Ser Ile Ala
            130                 135                 140
Gly Arg Val Asn Val Arg Asn Ala Ala Val Tyr Gln Ala Thr Lys Phe
145                 150                 155                 160
Gly Val Asn Ala Phe Ser Glu Thr Leu Arg Gln Glu Val Thr Glu Arg
                    165                 170                 175
Gly Val Arg Val Val Val Ile Glu Pro Gly Thr Thr Asp Thr Glu Leu
                180                 185                 190
Arg Gly His Ile Thr His Thr Ala Thr Lys Glu Met Tyr Glu Gln Arg
            195                 200                 205
Ile Ser Gln Ile Arg Lys Leu Gln Ala Gln Asp Ile Ala Glu Ala Val
210                 215                 220
Arg Tyr Ala Val Thr Ala Pro His His Ala Thr Val His Glu Ile Phe
225                 230                 235                 240
Ile Arg Pro Thr Asp Gln Val Glx
                245
```

(2) INFORMATION FOR SEQ ID NO: 12:

(i) SEQUENCE CHARACTERISTICS:
        (A) LENGTH: 409 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 12:

```
Met Met Asn Glu Ala Ala Pro Gln Ser Asp Gln Val Ala Pro Ala Tyr
 1               5                  10                  15
Pro Met His Arg Val Cys Pro Val Asp Pro Pro Gln Leu Ala Gly
                20                  25                  30
Leu Arg Ser Gln Lys Ala Ala Ser Arg Val Thr Leu Trp Asp Gly Ser
             35                  40                  45
Gln Val Trp Leu Val Thr Ser His Ala Gly Ala Arg Ala Val Leu Gly
 50                  55                  60
Asp Arg Arg Phe Thr Ala Val Thr Ser Ala Pro Gly Phe Pro Met Leu
 65                  70                  75                  80
Thr Arg Thr Ser Gln Leu Val Arg Ala Asn Pro Glu Ser Ala Ser Phe
                 85                  90                  95
Ile Arg Met Asp Asp Pro Gln His Ser Arg Leu Arg Ser Met Leu Thr
                100                 105                 110
Arg Asp Phe Leu Ala Arg Arg Ala Glu Ala Leu Arg Pro Ala Val Arg
            115                 120                 125
Glu Leu Leu Asp Glu Ile Leu Gly Gly Leu Val Lys Gly Glu Arg Pro
130                 135                 140
```

-continued

```
Val Asp Leu Val Ala Gly Leu Thr Ile Pro Val Pro Ser Arg Val Ile
145                 150                 155                 160

Thr Leu Leu Phe Gly Ala Gly Asp Asp Arg Arg Glu Phe Ile Glu Asp
                165                 170                 175

Arg Ser Ala Val Leu Ile Asp Arg Gly Tyr Thr Pro Glu Gln Val Ala
                180                 185                 190

Lys Ala Arg Asp Glu Leu Asp Gly Tyr Leu Arg Glu Leu Val Glu Glu
                195                 200                 205

Arg Ile Glu Asn Pro Gly Thr Asp Leu Ile Ser Arg Leu Val Ile Asp
210                 215                 220

Gln Val Arg Pro Gly His Leu Arg Val Glu Glu Met Val Pro Met Cys
225                 230                 235                 240

Arg Leu Leu Leu Val Ala Gly His Gly Thr Thr Thr Ser Gln Ala Ser
                245                 250                 255

Leu Ser Leu Leu Ser Leu Leu Thr Asp Pro Glu Leu Ala Gly Arg Leu
                260                 265                 270

Thr Glu Asp Pro Ala Leu Leu Pro Lys Ala Val Glu Glu Leu Leu Arg
                275                 280                 285

Phe His Ser Ile Val Gln Asn Gly Leu Ala Arg Ala Ala Val Glu Asp
290                 295                 300

Val Gln Leu Asp Asp Val Leu Ile Arg Ala Gly Glu Gly Val Val Leu
305                 310                 315                 320

Ser Leu Ser Ala Gly Asn Arg Asp Glu Thr Val Phe Pro Asp Pro Asp
                325                 330                 335

Arg Val Asp Val Asp Arg Asp Ala Arg Arg His Leu Ala Phe Gly His
                340                 345                 350

Gly Met His Gln Cys Leu Gly Gln Trp Leu Ala Arg Val Glu Leu Glu
                355                 360                 365

Glu Ile Leu Ala Ala Val Leu Arg Trp Met Pro Gly Ala Arg Leu Ala
370                 375                 380

Val Pro Phe Glu Glu Leu Asp Phe Arg His Glu Val Ser Ser Tyr Gly
385                 390                 395                 400

Leu Gly Ala Leu Pro Val Thr Trp Glx
                405
```

(2) INFORMATION FOR SEQ ID NO: 13:

(i) SEQUENCE CHARACTERISTICS:
        (A) LENGTH: 11604 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
GAATTCGAGT CATCGGGTTC GGCGACGGAT GGGCGGTTCG GCCACGCACC GTCACTCTTC      60

GTCCCCTCTT CACAAGAACT CCCGATACGT GGAGAAGAGA GCGTGAAGAG CGCGTCCGGT     120

CAGGGTTGCC GAGAACCGTC CACCATGACG GAGCCTGGTA CTGACGGAGT CTGGAGACCG     180

CTCATGTCCC GTGTATCGAC CGCCCCCAGC GGCAAGCCTA CCGCCGCTCA CGCCCTCCTG     240

TCACGGTTGC GTGATCACGG TGTGGGGAAG GTGTTTGGGG TTGTCGGCCG AGAGGCCGCG     300

TCGATTCTCT TCGACGAGGT CGAGGGGATC GACTTCGTTC TGACCCGCCA CGAGTTCACC     360

GCGGGTGTCG CCGCTGATGT CCTCGCGCGG ATCACCGGTC GCCCCAGGC GTGCTGGGCC      420

ACCCTGGGCC CCGGTATGAC CAACCTCTCC ACCGGTATCG CCACGTCCGT CCTGGACCGC     480
```

-continued

```
TCGCCGGTCA TCGCGCTCGC CGCGCAGTCG GAGTCGCACG ACATCTTCCC GAACGACACC      540
CACCAGTGCC TGGACTCGGT GGCGATCGTC GCCCCGATGT CCAAGTACGC CGTGGAGCTC      600
CAGCGGCCCC ACGAGATCAC CGACCTCGTC GACTCCGCCG TGAACGCGGC CATGACCGAG      660
CCGGTCGGGC CCTCCTTCAT CTCCCTCCCG GTGGACCTGC TCGGCTCCTC CGAGGGCATC      720
GACACCACCG TCCCCAACCC GCCGGCGAAC ACCCCGGCGA AACCGGTCGG CGTCGTCGCC      780
GACGGCTGGC AGAAGGCCGC CGACCAGGCC GCCGCCCTGC TCGCCGAGGC CAAGCACCCG      840
GTGCTCGTCG TCGGAGCGGC CGCGATCCGC TCGGGCGCCG TCCCGGCGAT CCGCGCCCTG      900
GCCGAGCGCC TGAACATCCC GGTCATCACG ACCTACATCG CCAAGGGTGT CCTGCCGGTC      960
GGCCACGAGC TGAACTACGG CGCCGTCACC GGCTACATGG ACGGCATCCT CAACTTCCCG     1020
GCGCTCCAGA CCATGTTCGC CCCGGTGGAC CTCGTCCTCA CCGTCGGCTA CGACTACGCC     1080
GAGGACCTGC GCCCGTCCAT GTGGCAGAAG GGCATCGAGA AGAAGACCGT CCGTATCTCC     1140
CCGACGGTCA ACCCGATCCC CCGGGTCTAC CGGCCCGACG TCGACGTCGT CACCGACGTC     1200
CTCGCCTTCG TGGAGCACTT CGAGACCGCG ACCGCCTCCT TCGGGGCCAA GCAGCGCCAC     1260
GACATCGAGC CGCTGCGCGC CCGGATCGCG GAGTTCCTGG CCGACCCGGA GACCTACGAG     1320
GACGGCATGC GCGTCCACCA GGTCATCGAC TCCATGAACA CCGTCATGGA GGAGGCCGCC     1380
GAGCCCGGCG AGGGCACGAT CGTCTCCGAC ATCGGCTTCT TCCGTCACTA CGGTGTGCTC     1440
TTCGCCCGCG CCGACCAGCC CTTCGGCTTC CTCACCTCGG CGGGCTGCTC CAGCTTCGGC     1500
TACGGCATCC CCGCCGCCAT CGGCGCCCAG ATGGCCCGCC GGACCAGCC GACCTTCCTC     1560
ATCGCGGGTG ACGGCGGCTT CCACTCCAAC AGCTCCGACC TGGAGACCAT CGCCCGGCTC     1620
AACCTGCCGA TCGTGACCGT CGTCGTCAAC AACGACACCA ACGGCCTGAT CGAGCTGTAC     1680
CAGAACATCG GTCACCACCG CAGCCACGAC CCGGCGGTCA AGTTCGGCGG CGTCGACTTC     1740
GTCGCGCTCG CCGAGGCCAA CGGTGTCGAC GCCACCCGCG CCACCAACCG CGAGGAGCTG     1800
CTCGCGGCCC TGCGCAAGGG TGCCGAGCTG GGTCGTCCGT TCCTCATCGA GGTCCCGGTC     1860
AACTACGACT TCCAGCCGGG CGGCTTCGGC GCCCTGAGCA TCTGATCATG GGGGCACCGG     1920
TTCTTCCGGC TGCCTTCGGG TTCCTGGCCT CCGCCCGAAC GGGCGGGGGC CGGGCCCCCG     1980
GCCCGGTCTT CGCGACCCGG GGCAGCCACA CCGACATCGA CACGCCCCAG GGGGAGCGCT     2040
CGCTCGCGGC GACCCTGGTG CACGCCCCCT CGGTCGCGCC CGACCGCGCG GTGGCGCGCT     2100
CCCTCACCGG CGCGCCCACC ACCGCGGTGC TCGCCGGTGA GATCTACAAC CGGGACGAAC     2160
TCCTCTCCGT GCTGCCCGCC GGACCCGCGC CGGAGGGGGA CGCGGAGCTG GTCCTGCGGC     2220
TGCTGGAACG CTATGACCTG CATGCCTTCC GGCTGGTGAA CGGGCGCTTC GCGACCGTGG     2280
TGCGGACCGG GGACCGGGTC CTGCTCGCCA CCGACCACGC CGGTTCGGTG CCGCTGTACA     2340
CCTGTGTGGC GCCGGGCGAG GTCCGGGCGT CCACCGAGGC CAAGGCGCTC GCCGCGCACC     2400
GCGACCCGAA GGGCTTCCCG CTCGCGGACG CCCGCCGGGT CGCCGGTCTG ACCGGTGTCT     2460
ACCAGGTGCC CGCGGGCGCC GTGATGGACA TCGACCTCGG CTCGGGCACC GCCGTCACCC     2520
ACCGCACCTG GACCCCGGGC CTCTCCCGCC GCATCCTGCC GGAGGGCGAG GCCGTCGCGG     2580
CCGTGCGGGC CGCGCTGGAG AAGGCCGTCG CCCAGCGGGT CACCCCCGGC GACACCCCGT     2640
TGGTGGTGCT CTCCGGCGGA ATCGACTCCT CCGGGGTCGC GGCCTGTGCG CACCGGGCGG     2700
CCGGGGAACT GGACACGGTG TCCATGGGCA CCGACACGTC CAACGAGTTC CGCGAGGCCC     2760
GGGCGGTCGT CGACCATCTG CGCACCCGGC ACCGGGAGAT CACCATCCCG ACCACCGAGC     2820
TGCTGGCGCA GCTCCCGTAC GCGGTGTGGG CCTCCGAGTC GGTGGACCCG GACATCATCG     2880
```

```
AGTACCTGCT CCCCCTGACA GCGCTCTACC GGGCGCTCGA CGGGCCGGAG CGCCGCATCC   2940

TCACCGGGTA CGGCGCGGAC ATCCCCCTCG GGGGCATGCA CCGCGAGGAC CGGCTGCCCG   3000

CGCTGGACAC CGTTCTCGCG CACGACATGG CCACCTTCGA CGGGCTGAAC GAGATGTCCC   3060

CGGTGCTGTC CACGCTGGCG GGGCACTGGA CCACCCACCC GTACTGGGAC CGGGAGGTCC   3120

TCGATCTGCT GGTCTCGCTG GAGGCCGGGC TCAAGCGGCG GCACGGCCGG ACAAGTGGG   3180

TGCTGCGCGC CGCGATGGCC GACGCCCTCC CGGCGGAGAC CGTCAACCGG CCCAAGCTGG   3240

GCGTCCACGA GGGCTCGGGC ACCACGTCCT CGTTCTCCCG GCTGCTGCTG GACCACGGTG   3300

TCGCCGAGGA CCGCGTCCAC GAGGCGAAGC GGCAGGTGGT GCGCGAGCTG TTCGATCTCA   3360

CGGTCGGGGG CGGACGGCAC CCCTCCGAGG TGGACACCGA CGATGTGGTG CGCTCCGTGG   3420

CCGACCGGAC CGCGCGGGGG GCGGCCTAGT CCCGCCACGG GGAGCCCGCC GGACGCCGGA   3480

CCCGCGCGGG ACCCGTACCC GGGGCCGCCC GCGGACTCCG GCGCACCGGC ACCCCTGTCC   3540

CCCACCCGTT GACGACCGTC GGCCCTCGGC CCTCGCGGCC CCTGACGACC GTCGCCCGAT   3600

TCCCAGGAGG GAGCTGAAAG CGTGGAGCGC ATCGACTCGC ACGTTTCACC CCGCTACGCA   3660

CAGATCCCCA CCTTCATGCG CCTGCCGCAC GATCCCCAGC CCCGCGGCTA TGACGTGGTG   3720

GTCATCGGAG CCCCCTACGA CGGGGGCACC AGCTACCGTC CCGGCGCCCG GTTCGGCCCC   3780

CAGGCCATCC GCAGTGAGTC GGGCCTCATC CACGGTGTCG GCATCGACCG GGGCCCCGGC   3840

ACGTTCGACC TGATCAACTG TGTCGACGCC GGGGACATCA ATCTGACGCC GTTCGACATG   3900

AACATCGCGA TCGACACGGC GCAGAGCCAT CTGTCGGGCC TGCTGAAGGC CAACGCCGCC   3960

TTTCTGATGA TCGGCGGCGA CCACTCGCTA ACGGTGGCCG CCCTGCGCGC GGTCGCGGAG   4020

CAGCACGGCC CGCTCGCCGT GGTGCACCTG GACGCGCACT CCGACACCAA CCCGGCCTTC   4080

TACGGGGGCC GGTACCACCA CGGCACCCCC TTCCGGCACG GGATCGACGA GAAGCTGATC   4140

GACCCGGCGG CGATGGTCCA GATCGGCATC CGGGGCCACA ACCCGAAGCC GGACTCGCTC   4200

GACTACGCCC GGGGCCACGG CGTCCGGGTG GTCACGGCGG ACGAGTTCGG CGAGCTGGGG   4260

GTGGGCGGGA CCGCCGACCT CATCCGCGAG AAGGTCGGCC AGCGGCCCGT GTACGTCTCG   4320

GTCGACATCG ACGTGGTCGA CCCCGCCTTC GCCCCGGTA CGGGCACGCC CGCGCCGGGC   4380

GGGCTCCTCT CGCGCGAGGT GCTGGCGCTG CTGCGCTGCG TGGGTGACCT GAAGCCGGTC   4440

GGCTTCGACG TGATGGAGGT GTCACCCCTC TACGACCACG GCGGGATCAC TTCGATCCTG   4500

GCCACGGAGA TCGGTGCGGA ACTGCTCTAC CAGTACGCCC GAGCCCACAG AACCCAGTTG   4560

TGAAGGAGAC ATCGTGTCAT GGCCTCTCCG ATAGTTGACT GCACCCCGTA CCGCGACGAG   4620

CTGCTCGCGC TCGCCTCCGA GCTTCCCGAG GTGCCGCGCG CGGACCTCCA TGGCTTCCTC   4680

GACGAGGCGA AGACGCTGGC CGCCCGTCTC CCGGAGGGGC TGGCCGCCGC TCTCGACACC   4740

TTCAACGCCG TGGGCAGCGA GGACGGTTAT CTGCTGCTGC GCGGGCTGCC CGTCGACGAC   4800

AGCGAGCTGC CCGAGACGCC GACCTCCACC CCGGCCCCGC TGGACCGCAA GCGGCTGGTG   4860

ATGGAGGCCA TGCTCGCGCT GGCCGGCCGC CGGCTCGGTC TGCACACGGG GTACCAGGAG   4920

CTGCGCTCGG GCACGGTCTA CCACGACGTG TACCCGTCGC CCGGCGCGCA CTACCTGTCC   4980

TCGGAGACCT CCGAGACGCT GCTGGAGTTC CACACGGAGA TGGCGTACCA CATCCTCCAG   5040

CCGAACTACG TCATGCTGGC CTGCTCCCGC GCGGACCACG AGAACCGGGC GGAGACGCTG   5100

GTCGGCTCGG TCCGCAAGGC GCTGCCCCTG CTGGACGAGA AGACCGGGGC CCGTCTCTTC   5160

GACCGCAAGG TGCCCTGCTG CGTGGACGTG GCCTTCCGCG GCGGGTCGA CGACCCGGGC   5220

GCGATCGCCA ACGTCAAGCC GCTCTACGGG GACGCGAACG ACCCGTTCCT CGGGTACGAC   5280
```

```
CGCGAGCTGC TGGCGCCGGA GGACCCCGCG GACAAGGAGG CCGTCGCCCA TCTGTCCCAG    5340

GCGCTCGACG ATGTGACCGT CGGGGTGAAG CTCGTCCCCG GTGACGTCCT CATCATCGAC    5400

AACTTCCGCA CCACGCACGC GCGGACGCCG TTCTCGCCCC GCTGGGACGG GAAGGACCGC    5460

TGGCTGCACC GCGTCTACAT CCGCACCGAC CGCAATGGAC AGCTCTCCGG CGGCGAGCGC    5520

GCGGGCGACA CCATCTCGTT CTCGCCGCGC CGCTGAGCCC GGCTCCCCGA GGCCCTGGGC    5580

CCCGGCGCCG GAACCGGCTC CCGGTCCTGC CCCCTCACCC GCCGCGCGGG TGAGGGGCA    5640

GGCCCCTTTG TGCCGGGTGC CGTGCGTCCT GCGAGGGTGC CGGGGCGGGG GGACGGCGG    5700

AGGTGCCCGG CGGCCGGGTG CCGTGCGCCG CCCGTGGGTG CTGTACAGCA CTCCGTGTGC    5760

CGTGCGCCAC CCCGTGCATA AATTTGCCAC TCTATGGGAA ATAATGCAGA GTGCGACGGG    5820

TGAGGCCGTC GCCGTGCCCT TTCCGTGACA GGAGACGCTG ACATGTCCGA CAGCACACCG    5880

AAGACGCCCC GGGGATTCGT GGTGCACACG GCGCCGGTGG GCCTGGCCGA CGACGGCCGC    5940

GACGACTTCA CCGTCCTCGC CTCCACCGCC CCGGCCACCG TGAGCGCCGT CTTCACCCGC    6000

TCCCGCTTCG CCGGGCCGAG CGTCGTGCTG TGCCGGGAGG CGGTGGCCGA CGGGCAGGCG    6060

CGCGGTGTGG TGGTGCTGGC CCGCAACGCG AATGTCGCGA CCGGCCTGGA GGGCGAGGAG    6120

AACGCGCGCG AGGTGCGCGA GGCCGTCGCC CGGGCCCTCG GCTGCCGGA GGGCGAGATG    6180

CTGATCGCCT CCACCGGGGT GATCGGCCGG CAGTACCCGA TGGAGAGCAT CCGGGAGCAC    6240

CTCAAGACGC TGGAGTGGCC CGCCGGGGAG GGCGGCTTCG ACCGCGCGGC CCGCGCCATC    6300

ATGACGACCG ACACCCGGCC CAAGGAGGTC CGGGTCAGCG TCGGCGGGGC GACCCTCGTG    6360

GGCATCGCCA AGGGCGTCGG CATGCTGGAG CCCGACATGG CGACGCTGCT GACCTTCTTC    6420

GCCACGGACG CCCGGCTGGA CCCGGCCGAG CAGGACCGCC TCTTCCGCCG GGTCATGGAC    6480

CGCACCTTCA ACGCGGTCAG CATCGACACC GACACCTCCA CCAGCGACAC GGCGGTGCTG    6540

TTCGCCAACG GCCTGGCGGG CGAGGTCGAC GCCGGGGAGT TCGAGGAGGC GCTGCACACG    6600

GCGGCGCTGG CCCTGGTCAA GGACATCGCG AGCGACGGCG AGGGCGCGGC CAAGCTGATC    6660

GAGGTCCAGG TCACCGGCGC CCGCGACGAC GCCCAGGCCA GCGGGTCGG CAAGACCGTC    6720

GTCAACTCCC CGTTGGTGAA GACCGCCGTG CACGGCTGCG ACCCCAACTG GGGCCGGGTC    6780

GCCATGGCGA TCGGCAAGTG CTCGGACGAC ACCGACATCG ACCAGGAGCG GGTGACGATC    6840

CGCTTCGGCG AGGTCGAGGT CTATCCGCCG AAGGCCCGGG CGACCAGGC CGACGACGCG    6900

CTGCGGGCCG CCGTCGCGGA GCATCTGCGG GGCGACGAGG TGGTCATCGG GATCGACCTC    6960

GCCATCGCGG ACGGGGCCTT CACCGTCTAC GGCTGCGACC TCACCGAGGG CTATGTCCGG    7020

CTGAACTCGG AGTACACCAC CTGATCCCCG GACAGGGAAC GGGCCGCCGC CCCGTTCCCT    7080

GTCCGCTCCC GTCCCGTGTG GTTATACCGA CCGTTCCCCG GCTATGCGCA CGGGACGGAG    7140

CGGCCCCCGC CGGGCCCCGC CCGGCCGCAC GATGAGGGGC GATGCAAGGT GACGAGGGCA    7200

GGAGGGACAT GGAGACCACT CGGTCGACGA CCGCGGACGA GGGCTTCGAC GCCGGGGTAC    7260

GGGGAGTGGT CGCGCCGACC GACGCCCGG GCGGGACGCT GCGGCTGGTC CGCACGGACG    7320

ACTTCGACTC GCTCGACCCC GGCAACACGT ACTACGCCTA CACCTGGAAC TTCCTCCGGC    7380

TCATCGGCCG GACGCTGGTC ACCTTCGACA CCGCGCCGGG CAAGGCGGGC CAGCGGCTCG    7440

TGCCCGACCT CGCCGAGTCG CTGGGCGAGT CCTCCGAGGA CGGCCGGGTC TGGACCTACC    7500

GGCTGCGCGA GGGCCTGCGC TACGAGGACG GCACGCCGGT CGTCTCGGCC GACATCAAGC    7560

ACGCCATCGC CCGCAGCAAC TACGGCACCG ATGTCCTGGG CGCCGGTCCG ACCTACTTCC    7620

GCCACCTCCT GGGCACCGAG TACGGCGGCC CCTGGCGGGA GCCGGACGCC GACGGACCGG    7680
```

```
TGACGCTGGA GACCCCGGAC GAGCGGACGC TGGTCTTCCG GCTGCGGGAG CCGTTCGCGG    7740

GGATGGATCT GCTGGCGACC ATGCCGTCCA CCACCCCCGT GCCGCGCGAC CGGGACACCG    7800

GCGCCGAGTA CCGGCTGCGG CCCGTGGCGA CCGGCCCGTA CCGGATCGTC TCGTACACCC    7860

GGGGCGAGCT GGCCGTCCTG GAGCCCAATC CGCACTGGGA CCCCGAGACC GACCCGGTGC    7920

GCGTCCAGCG CGCCTCCCGG ATCGAGGTGC ACCTCGGCAA GGACCCGCAC GAGGTGGACC    7980

GCATGCTGCT GGCGGGCGAG GCCCATGTGG ACCTCGCGGG CTTCGGTGTG CAGCCCGCGG    8040

CCCAGGAGCG CATCCTCGCC GAGCCGGAGC TGCGCGCGCA CGCGGACAAC CCGCTGACCG    8100

GCTTCACCTG GATCTACTGC CTGTCGAGCC GGATCGCCCC GTTCGACAAT GTGCACTGCC    8160

GGCGGGCCGT GCAGTTCGCC ACCGACAAAG CGGCCATGCA GGAGGCGTAC GGCGGCGCGG    8220

TGGGCGGCGA CATCGCGACC ACCCTGCTGC CCCCGACCCT CGACGGCTAC AAGCACTTCG    8280

ACCGCTACCC GGTCGGCCCC GAGGGCACCG GCGACCTGGA GGCCGCCCGC GCCGAGCTGA    8340

AGCTGGCCGG GATGCCCGAC GGCTTCCGCA CCAGGATCGC CGCCCGCAAG GACCGGCTCA    8400

AGGAGTACCG GGCCGCCGAG GCGCTGGCCG CCGGGCTCGC CCGGGTCGGC ATCGAGGCGG    8460

AGGTGCTGGA CTTCCCGTCG GGCGACTACT TCGACCGCTA CGGCGGCTGC CCGGAGTATC    8520

TGCGCGAGCA CGGGATCGGG ATCATCATGT TCGGCTGGGG CGCCGACTTC CCCGACGGAT    8580

ACGGCTTCCT CCAGCAGATC ACCGACGGGC GCGCGATCAA GGAGCGCGGC AACCAGAACA    8640

TGGGCGAGCT GGACGACCCG GAGATCAACG CGCTGCTGGA CGAGGGGCG CAGTGCGCCG    8700

ACCCGGCGCG GCGCGCGGAG ATCTGGCACC GCATCGACCA GCTCACGATG GACCACGCGG    8760

TCATCGTTCC GTATCTGTAC CCGCGGTCCC TGCTCTACCG GCACCCGGAC ACCCGCAACG    8820

CCTTCGTCAC CGGCTCCTTC GGGATGTACG ACTACGTGGC GCTCGGCGCG AAGTGAGCAC    8880

GGGGTCCGGC CCCGGGACCG TATGTCCCGG GGCCGGACCC CGCCCGTTCC CCGCCCGGTC    8940

CGGTCCGGAC CCGGTCGCGG CCCGCTCAGC CGGACATCCG GGCCCCGGCC GCGACCCCGC    9000

GCCGGATCGG CCAGTGGCCC TGCGCCAGGG GCCGTTCCAC GCTGCGGCAG GCGAGAGCGG    9060

CCTCGCGGAA CTCCGCCTCG TACAGCGCGA GCTGGCGCAG GAACTGCCGG GTCGGGCCGG    9120

TCAGGCTGGT CCCCCGCGGG CTGCGCAGCA GCAGCCGGGC GCCGAGGGAC TGCTCCAGCC    9180

GGTGAATCCG GCGGGTGAGC GCCGACTGGC TGATCGACAG CACCGCCGCG GCCCGGTTGA    9240

TGCTGCCGTG CCGGGCCACG GCCTGGAGCA GATGGAGATC GTCCACATCC AGTTTGCGGC    9300

CCTCGGCCTG GCCGGGCACG GAGCCCTGGT CGGGTCCCGC CCCGAAGCGG CGGGCGTCCG    9360

CGCCGGTGCG CTCCGCGTAC CACTGCGCCC ACCAGGGCTC GTCCAGCAGG TCGCGGTGGT    9420

GTTCGGCGAA GCGCCGGAGC TGGACCTCGG CGATCAGCGC GGCCAGCCGT CCCGCCAGCG    9480

CCCGGGGCAC GATGGTGGGG TCGACGAGCA GACTCGTGGT GCGGCGCGGG CGCTCCGCCA    9540

GGGAGCGGCG CACCAGCGAG GGGTCCTGCA CCGCCGGGTG GGTGGGCGAG CCGAGACCTA    9600

TCGCGTCCCC GCGGCGCAGG ATGCCCCGGG CAACCGATGC CCCCGTGATG TGGAGCCGGG    9660

TGGGCGCGGT GAGCCCGGCC AGCTGGAAGA CACGTGTCAC CAGGATCTCC GAGCCGGGTC    9720

CCGTCTCGGA CACCCAGGTC TCGTCCCGCA GATCGGCGAG CGAGACCTCC CGCCGGGCGG    9780

CCAGCGGATG GTCCCGGGGC AGGATCACCC ACAGCGGGTC GTCCAGCACC TCACAGGTGC    9840

GCACGGACCG CTCCAGGCTG TGCCGGGGGG ACTGGAGGCT CCAGGTGTAG GCCGCGTCCA    9900

CCTGGTAGCC CGCCAGTTGG GCGGCGACCT GGTGCGGGC CTCGTGCCGG ACCGACAGCA    9960

GCAGGTCCAG CGAGGCCGCC GCGTCCTCCA CCACCTCGTC GAGCAGGGGT TCCGTGGAGA   10020

CCAGCGACAG CACCTCCGGG GCGTCCACGG CCTCGGAGCC ATGGCCGAAG ATATGCGTCC   10080
```

```
GCGCGGCCAG GTCGACCTGG TGGAAGAACC GCCGCCCGGC GACGAGGATG CGGGAGCCCG     10140

CGGTGGTCAG CCGGGCCGTG TGGCGGCTGC GCAGGGTCAG CGGGAGGCCG ACGATCCGGT     10200

CCAGCCGGTC GAGTCTGCGC TCCACGGTGC CGTGCCGGAC ACCCGTCCGC CGGGCCACTT     10260

CCATGAGGTC TCCGCAGTGT CCCACCGCGT CCAGTAAAGA CAGATCGCAT CGGCTGACAC     10320

CAGCAGACGT CGGTTCTGAC CCGAGAGACA ATGTCGGTTC CCTTTTCCGT CAAGGACTGT     10380

ACCGCTGAAT TGTCCGAAGT GGCTCTTGAA TTGCTTCGGA ATCGATCCTA GGCAGCGCCG     10440

CTCTTCGGAT TCTCCTCGCC GGGAAGCGGA ACGCGCCCGG CCGGATGGCG GGCGCGCTCC     10500

GGGCGCCGTC CCGGGAACGG GGGACGGGGC ACGGCACGGC CGGCCACCCG GTCCGGGCGC     10560

GCGGCGTGGA CCTGGTCGGC GGACGGGTGT CAGACCTGGT CGGTGGGCG TATGAAGATC      10620

TCGTGGACGG TCGCGTGGTG CGGCGCGGTC ACGGCGTAGC GGACCGCCTC CGCGATGTCC     10680

TGGGCCTGGA GCTTGCGGAT CTGGCTGATC CGCTGCTCGT ACATCTCCTT GGTGGCGGTG     10740

TGGGTGATGT GGCCGCGCAG CTCCGTGTCG GTGGTGCCCG GCTCGATGAC GACGACCCGC     10800

ACCCCGCGCT CGGTGACCTC CTGGCGCAGC GTCTCGCTGA ACGCGTTCAC ACCGAACTTC     10860

GTGGCCTGGT AGACGGCCGC GTTGCGGACG TTCACCCGGC CCGCGATCGA GGACATCTGC     10920

ACCACGGTGC CCTTGCTGCG CAGCAGATGG GGAAGGGCCG CCCGGGTCAT GTACATCAGG     10980

CCCAGGAGAT TGGTGTCGAT CATCCGGGTC CAGTCGGTGG TGTCGGCGTC CTCCACCGGG     11040

CCGAGCAGCA TGATCCCGGC GTTGTTGACG AGGATGTCGA GGCCGCCCAG CGCCTCGACG     11100

GTGGAGGCGA CGGCGGCGTC CACCCCCTGC CGGTCGGCGA CGTCGAGTTC GAGGACATGG     11160

ACCTTCGCCC CGGCGGCGGT CAGCTCGTCA CCCAGGGCGC GCAGCTTCTC GACCCGGCGC     11220

GCGGCGATGG CCACGGCGGC GCCCTCGGCG GCCAGGGCGC GGGCCGTGGC CTCGCCGATG     11280

CCCGAGCTCG CGCCCGTGAT GAGCGCGACT TTCCCCTGGA GTGCGGATGG CATCATTTCC     11340

TCCACATGGT GCTGCGATCG TGGTGAGCGT ATGAAGAAGG GGTGAGACCT GCCGTGCCGG     11400

GGCGGGTTCC GTACGCCGGA CCGTTGCGGT GGGCACGGCC GACCGGGTAC GGATGGCCGC     11460

AGTTCCCCGG GGAGTTCCCG GGGAATGGTG AATACCGCGG CGCTCTCCGA TGGTCTTCGG     11520

AGGACACCCG GGGATTCACC GGGAATCAGC GGCCGGAGTT CTCCCCGTCC ACGGCAGACG     11580

CTATCAGCGT CGCATTCCCC GGTG                                           11604

(2) INFORMATION FOR SEQ ID NO: 14:

(i) SEQUENCE CHARACTERISTICS:
        (A) LENGTH: 1656 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

TCAGCCGGCC GCGAGGTTGC TGAGGAACTT CGCGGCGACG GGGCCCGCGT CGGCGCCGCC       60

CGACCCGCCG TCCTCCAGCA GGACCGACCA GGCGATGTTC CGGTCGCCCT GGTAGCCGAT      120

CATCCAGGCG TGCGTCTTCG GCGGCTTCTC GGTGCCGAAC TCGGCGGTAC CGGTCTTGGC      180

GTGCGGCTGT CCGCCGAGGC CCCGCAGGGC GTCGCCGGCG CCGTCGGTGA CGGTCGAACG      240

CATCATGGAA CGCAGCGAGT CGACGATGCC CGGGGCCATC CGGGGGGCCT GGTGCGGCTT      300

CTTGACCGCG TCGGGCACCA GCACGGGCTG CTTGAACTCG CCCTGCTTGA CGGTGGCGGC      360

GATGGAGGCC ATCACCAGGG GCGACGCCTC GACCCTGGCC TGTCCGATGG TGGACGCGGC      420
```

-continued

```
CTTGTCGTTC TCGCTGTTGG AGACGGGGAC GCTGCCGTCG AAGGTGGAGG CGCCGACGTC      480

CCAGGTGCCG CCGATGCCGA AGGCTTCGGC GGCCTGCTTC AGGCTGGACT CGGAGAGCTT      540

GCTGCGGGAG TTGACGAAGA ACGTGTTGCA GGAGTGGGCG AAGCTGTCCC GGAAGGTCGA      600

GCCCGCGGGC AGCGTGAACT GGTCCTGGTT CTCGAAGCTC TGGCCGTTGA CATGGGCGAA      660

CTTCGGGCAG TCGGCCCGCT CCTCCGGGTT CATCCCCTGC TGGAGCAGGG CCGCGGTGGT      720

GACCACCTTG AAGGTGGAGC CGGGCGGGTA GCGGCCCTCC AGCGCGCGGT TCATGCCGGA      780

GGGCACGTTC GCGGCGGCCA GGATGTTGCC GGTGGCGGGG TCGACGGCGA CGATCGCCGC      840

GTTCTTCTTC GAGCCCTCCA GGGCCGCCGC GGCGGCGGAC TGGACCCGCG GTCGATGGT       900

GGTCTTCACC GGCTTGCCCT CGGTGTCCTT GAGGCCGGTG AGCTTCTTGA CCACCTGGCC      960

GGACTCACGG TCCAGGATCA CGACCGAGCG CGCCGCGCCG GAGCCGCCGG TGAGCTGCTT      1020

GTCGTAGCGG GACTGGAGGC CCGCCGAGCC CTTGCCGGTC CTGGGGTCGA CCGCGCCGAT      1080

GATGGAGGCG GCCTGGAGGA CATTGCCGTT GGCGTCGAGG ATGTCCGCGC GCTCCCGCGA      1140

CTTGAGGGCA AGGGTCTGCC CCGGAACCAT CTGCGGATGG ATCATCTCGG TGTTGAACGC      1200

GACCTTCCAC TCCTTGCCGC CGCCGACGAC CTTCGCGGTG GAGTCCCAGG CGTACTCCCC      1260

GGCCCCGGGG AGGGTCATTC TGACGGTGAA CGGTATCTCC ACCTCGCCCT CGGGGTTCTT      1320

CTCCCCGGTC TTGGCGGTGA TCTCCGTCTT CGTCGGCTTG AGGTTGGTCA TGACGGATTT      1380

GATCAGCGAC TCGGCGTTGT CCGGGGTGTC CGTCAGCCCG GCGGCCGTCG GGGCGTCGCC      1440

CTTCTCCCAG GCGCCGAGGA AGGTGTCGAA CTGTCCGGCC GCCGCCTCCA CCTCGGGGTC      1500

GCCCGAATCC TTCTCGTCGG CAACCAGGCT GGTGTAACCC CAATAGCCGA GCCCCACCGT      1560

CACGGCCAGC CCGGCGACCA CCGCGGTGGC CGCCCGGCCA CGGGAGCGGC GCCTGCCCTG      1620

CGGCGGGTCA TCGCCATAGT TGTCGGAATG CGTCAT                                1656
```

(2) INFORMATION FOR SEQ ID NO: 15:

(i) SEQUENCE CHARACTERISTICS:
        (A) LENGTH: 1722 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
ATGTCCCGTG TATCGACCGC CCCCAGCGGC AAGCCTACCG CCGCTCACGC CCTCCTGTCA       60

CGGTTGCGTG ATCACGGTGT GGGGAAGGTG TTTGGGGTTG TCGGCCGAGA GGCCGCGTCG      120

ATTCTCTTCG ACGAGGTCGA GGGGATCGAC TTCGTTCTGA CCCGCCACGA GTTCACCGCG      180

GGTGTCGCCG CTGATGTCCT CGCGCGGATC ACCGGTCGCC CCCAGGCGTG CTGGGCCACC      240

CTGGGCCCCG GTATGACCAA CCTCTCCACC GGTATCGCCA CGTCCGTCCT GGACCGCTCG      300

CCGGTCATCG CGCTCGCCGC GCAGTCGGAG TCGCACGACA TCTTCCCGAA CGACACCCAC      360

CAGTGCCTGG ACTCGGTGGC GATCGTCGCC CCGATGTCCA AGTACGCCGT GGAGCTCCAG      420

CGGCCCCACG AGATCACCGA CCTCGTCGAC TCCGCCGTGA ACGCGGCCAT GACCGAGCCG      480

GTCGGGCCCT CCTTCATCTC CCTCCCGGTG GACCTGCTCG GCTCCTCCGA GGGCATCGAC      540

ACCACCGTCC CCAACCCGCC GGCGAACACC CCGGCGAAAC CGGTCGGCGT CGTCGCCGAC      600

GGCTGGCAGA AGGCCGCCGA CCAGGCCGCC GCCCTGCTCG CCGAGGCCAA GCACCCGGTG      660

CTCGTCGTCG GAGCGGCCGC GATCCGCTCG GGCGCCGTCC CGGCGATCCG CGCCCTGGCC      720
```

-continued

```
GAGCGCCTGA ACATCCCGGT CATCACGACC TACATCGCCA AGGGTGTCCT GCCGGTCGGC      780

CACGAGCTGA ACTACGGCGC CGTCACCGGC TACATGGACG GCATCCTCAA CTTCCCGGCG      840

CTCCAGACCA TGTTCGCCCC GGTGGACCTC GTCCTCACCG TCGGCTACGA CTACGCCGAG      900

GACCTGCGCC CGTCCATGTG GCAGAAGGGC ATCGAGAAGA AGACCGTCCG TATCTCCCCG      960

ACGGTCAACC CGATCCCCCG GGTCTACCGG CCCGACGTCG ACGTCGTCAC CGACGTCCTC     1020

GCCTTCGTGG AGCACTTCGA GACCGCGACC GCCTCCTTCG GGGCCAAGCA GCGCCACGAC     1080

ATCGAGCCGC TGCGCGCCCG GATCGCGGAG TTCCTGGCCG ACCCGGAGAC CTACGAGGAC     1140

GGCATGCGCG TCCACCAGGT CATCGACTCC ATGAACACCG TCATGGAGGA GGCCGCCGAG     1200

CCCGGCGAGG GCACGATCGT CTCCGACATC GGCTTCTTCC GTCACTACGG TGTGCTCTTC     1260

GCCCGCGCCG ACCAGCCCTT CGGCTTCCTC ACCTCGGCGG GCTGCTCCAG CTTCGGCTAC     1320

GGCATCCCCG CCGCCATCGG CGCCCAGATG GCCCGCCCGG ACCAGCCGAC CTTCCTCATC     1380

GCGGGTGACG GCGGCTTCCA CTCCAACAGC TCCGACCTGG AGACCATCGC CCGGCTCAAC     1440

CTGCCGATCG TGACCGTCGT CGTCAACAAC GACACCAACG GCCTGATCGA GCTGTACCAG     1500

AACATCGGTC ACCACCGCAG CCACGACCCG GCGGTCAAGT TCGGCGGCGT CGACTTCGTC     1560

GCGCTCGCCG AGGCCAACGG TGTCGACGCC ACCCGCGCCA CCAACCGCGA GGAGCTGCTC     1620

GCGGCCCTGC GCAAGGGTGC CGAGCTGGGT CGTCCGTTCC TCATCGAGGT CCCGGTCAAC     1680

TACGACTTCC AGCCGGGCGG CTTCGGCGCC CTGAGCATCT GA                        1722
```

(2) INFORMATION FOR SEQ ID NO: 16:

(i) SEQUENCE CHARACTERISTICS:
        (A) LENGTH: 1542 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
ATGGGGGCAC CGGTTCTTCC GGCTGCCTTC GGGTTCCTGG CCTCCGCCCG AACGGGCGGG       60

GGCCGGGCCC CCGGCCCGGT CTTCGCGACC CGGGGCAGCC ACACCGACAT CGACACGCCC      120

CAGGGGGAGC GCTCGCTCGC GGCGACCCTG GTGCACGCCC CCTCGGTCGC GCCCGACCGC      180

GCGGTGGCGC GCTCCCTCAC CGGCGCGCCC ACCACCGCGG TGCTCGCCGG TGAGATCTAC      240

AACCGGGACG AACTCCTCTC CGTGCTGCCC GCCGGACCCG CGCCGGAGGG GGACGCGGAG      300

CTGGTCCTGC GGCTGCTGGA ACGCTATGAC CTGCATGCCT TCCGGCTGGT GAACGGGCGC      360

TTCGCGACCG TGGTGCGGAC CGGGGACCGG GTCCTGCTCG CCACCGACCA CGCCGGTTCG      420

GTGCCGCTGT ACACCTGTGT GGCGCCGGGC GAGGTCCGGG CGTCCACCGA GGCCAAGGCG      480

CTCGCCGCGC ACCGCGACCC GAAGGGCTTC CCGCTCGCGG ACGCCCGCCG GGTCGCCGGT      540

CTGACCGGTG TCTACCAGGT GCCCGCGGGC GCCGTGATGG ACATCGACCT CGGCTCGGGC      600

ACCGCCGTCA CCCACCGCAC CTGGACCCCG GCCCTCTCCC GCCGCATCCT GCCGGAGGGC      660

GAGGCCGTCG CGGCCGTGCG GGCCGCGCTG GAGAAGGCCG TCGCCCAGCG GGTCACCCCC      720

GGCGACACCC CGTTGGTGGT GCTCTCCGGC GGAATCGACT CCTCCGGGGT CGCGGCCTGT      780

GCGCACCGGG CGGCCGGGGA ACTGGACACG GTGTCCATGG CACCGACAC GTCCAACGAG      840

TTCCGCGAGG CCCGGGCGGT CGTCGACCAT CTGCGCACCC GGCACGGGA GATCACCATC      900

CCGACCACCG AGCTGCTGGC GCAGCTCCCG TACGCGGTGT GGGCCTCCGA GTCGGTGGAC      960
```

```
CCGGACATCA TCGAGTACCT GCTCCCCCTG ACAGCGCTCT ACCGGGCGCT CGACGGGCCG    1020

GAGCGCCGCA TCCTCACCGG GTACGGCGCG GACATCCCCC TCGGGGGCAT GCACCGCGAG    1080

GACCGGCTGC CCGCGCTGGA CACCGTTCTC GCGCACGACA TGGCCACCTT CGACGGGCTG    1140

AACGAGATGT CCCCGGTGCT GTCCACGCTG GCGGGGCACT GGACCACCCA CCCGTACTGG    1200

GACCGGGAGG TCCTCGATCT GCTGGTCTCG CTGGAGGCCG GGCTCAAGCG GCGGCACGGC    1260

CGGGACAAGT GGGTGCTGCG CGCCGCGATG GCCGACGCCC TCCCGGCGGA GACCGTCAAC    1320

CGGCCCAAGC TGGGCGTCCA CGAGGGCTCG GGCACCACGT CCTCGTTCTC CCGGCTGCTG    1380

CTGGACCACG GTGTCGCCGA GGACCGCGTC CACGAGGCGA AGCGGCAGGT GGTGCGCGAG    1440

CTGTTCGATC TCACGGTCGG GGGCGGACGG CACCCCTCCG AGGTGGACAC CGACGATGTG    1500

GTGCGCTCCG TGGCCGACCG GACCGCGCGG GGGGCGGCCT AG                      1542

(2) INFORMATION FOR SEQ ID NO: 17:

(i) SEQUENCE CHARACTERISTICS:
        (A) LENGTH: 942 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

GTGGAGCGCA TCGACTCGCA CGTTTCACCC CGCTACGCAC AGATCCCCAC CTTCATGCGC      60

CTGCCGCACG ATCCCCAGCC CGCGGCTAT GACGTGGTGG TCATCGGAGC CCCCTACGAC     120

GGGGGCACCA GCTACCGTCC CGGCGCCCGG TTCGGCCCCC AGGCCATCCG CAGTGAGTCG    180

GGCCTCATCC ACGGTGTCGG CATCGACCGG GGCCCCGGCA CGTTCGACCT GATCAACTGT    240

GTCGACGCCG GGGACATCAA TCTGACGCCG TTCGACATGA ACATCGCGAT CGACACGGCG    300

CAGAGCCATC TGTCGGGCCT GCTGAAGGCC AACGCCGCCT TTCTGATGAT CGGCGGCGAC    360

CACTCGCTGA CGGTGGCCGC CCTGCGCGCG GTCGCGGAGC AGCACGGCCC GCTCGCCGTG    420

GTGCACCTGG ACGCGCACTC CGACACCAAC CCGGCCTTCT ACGGGGCCG GTACCACCAC    480

GGCACCCCCT TCCGGCACGG GATCGACGAG AAGCTGATCG ACCCGGCGGC GATGGTCCAG    540

ATCGGCATCC GGGGCCACAA CCCGAAGCCG GACTCGCTCG ACTACGCCCG GGGCCACGGC    600

GTCCGGGTGG TCACGGCGGA CGAGTTCGGC GAGCTGGGGG TGGGCGGGAC CGCCGACCTC    660

ATCCGCGAGA AGGTCGGCCA GCGGCCCGTG TACGTCTCGG TCGACATCGA CGTGGTCGAC    720

CCCGCCTTCG CCCCCGGTAC GGGCACGCCC GCGCCGGGCG GCTCCTCTC GCGCGAGGTG    780

CTGGCGCTGC TGCGCTGCGT GGGTGACCTG AAGCCGGTCG GCTTCGACGT GATGGAGGTG    840

TCACCCCTCT ACGACCACGG CGGGATCACT TCGATCCTGG CCACGGAGAT CGGTGCGGAA    900

CTGCTCTACC AGTACGCCCG AGCCCACAGA ACCCAGTTGT GA                       942

(2) INFORMATION FOR SEQ ID NO: 18:

(i) SEQUENCE CHARACTERISTICS:
        (A) LENGTH: 978 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 18:

ATGGCCTCTC CGATAGTTGA CTGCACCCCG TACCGCGACG AGCTGCTCGC GCTCGCCTCC      60
```

-continued

| | |
|---|---|
| GAGCTTCCCG AGGTGCCGCG CGCGGACCTC CATGGCTTCC TCGACGAGGC GAAGACGCTG | 120 |
| GCCGCCCGTC TCCCGGAGGG GCTGGCCGCC GCTCTCGACA CCTTCAACGC CGTGGGCAGC | 180 |
| GAGGACGGTT ATCTGCTGCT GCGCGGGCTG CCCGTCGACG ACAGCGAGCT GCCCGAGACG | 240 |
| CCGACCTCCA CCCCGGCCCC GCTGGACCGC AAGCGGCTGG TGATGGAGGC CATGCTCGCG | 300 |
| CTGGCCGGCC GCCGGCTCGG TCTGCACACG GGGTACCAGG AGCTGCGCTC GGGCACGGTC | 360 |
| TACCACGACG TGTACCCGTC GCCCGGCGCG CACTACCTGT CCTCGGAGAC CTCCGAGACG | 420 |
| CTGCTGGAGT TCCACACGGA GATGGCGTAC ACATCCTCC AGCCGAACTA CGTCATGCTG | 480 |
| GCCTGCTCCC GCGCGGACCA CGAGAACCGG GCGGAGACGC TGGTCGGCTC GGTCCGCAAG | 540 |
| GCGCTGCCCC TGCTGGACGA GAAGACCCGG GCCCGTCTCT TCGACCGCAA GGTGCCCTGC | 600 |
| TGCGTGGACG TGGCCTTCCG CGGCGGGGTC GACGACCCGG GCGCGATCGC CAACGTCAAG | 660 |
| CCGCTCTACG GGACGCGAA CGACCCGTTC CTCGGGTACG ACCGCGAGCT GCTGGCGCCG | 720 |
| GAGGACCCCG CGGACAAGGA GGCCGTCGCC CATCTGTCCC AGGCGCTCGA CGATGTGACC | 780 |
| GTCGGGGTGA AGCTCGTCCC CGGTGACGTC CTCATCATCG ACAACTTCCG CACCACGCAC | 840 |
| GCGCGGACGC CGTTCTCGCC CCGCTGGGAC GGGAAGGACC GCTGGCTGCA CCGCGTCTAC | 900 |
| ATCCGCACCG ACCGCAATGG ACAGCTCTCC GGCGGCGAGC GCGCGGGCGA CACCATCTCG | 960 |
| TTCTCGCCGC GCCGCTGA | 978 |

(2) INFORMATION FOR SEQ ID NO: 19:

(i) SEQUENCE CHARACTERISTICS:
        (A) LENGTH: 1182 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

| | |
|---|---|
| ATGTCCGACA GCACACCGAA GACGCCCCGG GGATTCGTGG TGCACACGGC GCCGGTGGGC | 60 |
| CTGGCCGACG ACGGCCGCGA CGACTTCACC GTCCTCGCCT CCACCGCCCC GGCCACCGTG | 120 |
| AGCGCCGTCT TCACCCGCTC CCGCTTCGCC GGGCCGAGCG TCGTGCTGTG CCGGGAGGCG | 180 |
| GTGGCCGACG GGCAGGCGCG CGGTGTGGTG GTGCTGGCCC GCAACGCGAA TGTCGCGACC | 240 |
| GGCCTGGAGG GCGAGGAGAA CGCGCGCGAG GTGCGCGAGG CCGTCGCCCG GGCCCTCGGG | 300 |
| CTGCCGGAGG GCGAGATGCT GATCGCCTCC ACCGGGGTGA TCGGCCGGCA GTACCCGATG | 360 |
| GAGAGCATCC GGGAGCACCT CAAGACGCTG GAGTGGCCCG CCGGGGAGGG CGGCTTCGAC | 420 |
| CGCGCGGCCC GCGCCATCAT GACGACCGAC ACCCGGCCCA AGGAGGTCCG GGTCAGCGTC | 480 |
| GGCGGGGCGA CCCTCGTGGG CATCGCCAAG GGCGTCGGCA TGCTGGAGCC CGACATGGCG | 540 |
| ACGCTGCTGA CCTTCTTCGC CACGGACGCC CGGCTGGACC CGGCCGAGCA GGACCGCCTC | 600 |
| TTCCGCCGGG TCATGGACCG CACCTTCAAC GCGGTCAGCA TCGACACCGA CACCTCCACC | 660 |
| AGCGACACGG CGGTGCTGTT CGCCAACGGC CTGGCGGGCG AGGTCGACGC CGGGGAGTTC | 720 |
| GAGGAGGCGC TGCACACGGC GGCGCTGGCC CTGGTCAAGG ACATCGCGAG CGACGGCGAG | 780 |
| GGCGCGGCCA AGCTGATCGA GGTCCAGGTC ACCGGCGCCC GCGACGACGC CCAGGCCAAG | 840 |
| CGGGTCGGCA AGACCGTCGT CAACTCCCCG TTGGTGAAGA CCGCCGTGCA CGGCTGCGAC | 900 |
| CCCAACTGGG GCCGGGTCGC CATGGCGATC GGCAAGTGCT CGGACGACAC CGACATCGAC | 960 |
| CAGGAGCGGG TGACGATCCG CTTCGGCGAG GTCGAGGTCT ATCCGCCGAA GGCCCGGGGC | 1020 |

```
GACCAGGCCG ACGACGCGCT GCGGGCCGCC GTCGCGGAGC ATCTGCGGGG CGACGAGGTG      1080

GTCATCGGGA TCGACCTCGC CATCGCGGAC GGGGCCTTCA CCGTCTACGG CTGCGACCTC      1140

ACCGAGGGCT ATGTCCGGCT GAACTCGGAG TACACCACCT GA                         1182
```

(2) INFORMATION FOR SEQ ID NO: 20:

(i) SEQUENCE CHARACTERISTICS:
        (A) LENGTH: 1668 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

```
ATGGAGACCA CTCGGTCGAC GACCGCGGAC GAGGGCTTCG ACGCCGGGGT ACGGGGAGTG        60

GTCGCGCCGA CCGACGCCCC GGGCGGGACG CTGCGGCTGG TCCGCACGGA CGACTTCGAC       120

TCGCTCGACC CCGGCAACAC GTACTACGCC TACACCTGGA ACTTCCTCCG GCTCATCGGC       180

CGGACGCTGG TCACCTTCGA CACCGCGCCG GGCAAGGCGG GCCAGCGGCT CGTGCCCGAC       240

CTCGCCGAGT CGCTGGGCGA GTCCTCCGAG GACGGCCGGG TCTGGACCTA CCGGCTGCGC       300

GAGGGCCTGC GCTACGAGGA CGGCACGCCG GTCGTCTCGG CCGACATCAA GCACGCCATC       360

GCCCGCAGCA ACTACGGCAC CGATGTCCTG GGCGCCGGTC CGACCTACTT CCGCCACCTC       420

CTGGGCACCG AGTACGGCGG CCCCTGGCGG GAGCCGGACG CCGACGGACC GGTGACGCTG       480

GAGACCCCGG ACGAGCGGAC GCTGGTCTTC CGGCTGCGGG AGCCGTTCGC GGGGATGGAT       540

CTGCTGGCGA CCATGCCGTC CACCACCCCC GTGCCGCGCG ACCGGGACAC CGGCGCCGAG       600

TACCGGCTGC GGCCCGTGGC GACCGGCCCG TACCGGATCG TCTCGTACAC CCGGGGCGAG       660

CTGGCCGTCC TGGAGCCCAA TCCGCACTGG GACCCCGAGA CCGACCCGGT GCGCGTCCAG       720

CGCGCCTCCC GGATCGAGGT GCACCTCGGC AAGGACCCGC ACGAGGTGGA CCGCATGCTG       780

CTGGCGGGCG AGGCCCATGT GGACCTCGCG GGCTTCGGTG TGCAGCCCGC GGCCCAGGAG       840

CGCATCCTCG CCGAGCCGGA GCTGCGCGCG CACGCGGACA CCCGCTGACG CGGCTTCACC       900

TGGATCTACT GCCTGTCGAG CCGGATCGCC CCGTTCGACA ATGTGCACTG CCGGCGGGCC       960

GTGCAGTTCG CCACCGACAA AGCGGCCATG CAGGAGGCGT ACGGCGGCGC GGTGGGCGGC      1020

GACATCGCGA CCACCCTGCT GCCCCCGACC CTCGACGGCT ACAAGCACTT CGACCGCTAC      1080

CCGGTCGGCC CCGAGGGCAC CGGCGACCTG GAGGCCGCCC GCGCCGAGCT GAAGCTGGCC      1140

GGGATGCCCG ACGGCTTCCG CACCAGGATC GCCGCCCGCA AGGACCGGCT CAAGGAGTAC      1200

CGGGCCGCCG AGGCGCTGGC CGCCGGGCTC GCCCGGGTCG GCATCGAGGC GGAGGTGCTG      1260

GACTTCCCGT CGGGCGACTA CTTCGACCGC TACGGCGGCT GCCCGGAGTA TCTGCGCGAG      1320

CACGGGATCG GATCATCAT GTTCGGCTGG GGCGCCGACT TCCCCGACGG ATACGGCTTC      1380

CTCCAGCAGA TCACCGACGG GCGCGCGATC AAGGAGCGCG GCAACCAGAA CATGGGCGAG      1440

CTGGACGACC CGGAGATCAA CGCGCTGCTG GACGAGGGGG CGCAGTGCGC CGACCCGGCG      1500

CGGCGCGCGG AGATCTGGCA CCGCATCGAC CAGCTCACGA TGGACCACGC GGTCATCGTT      1560

CCGTATCTGT ACCCGCGGTC CCTGCTCTAC CGGCACCCGG ACACCCGCAA CGCCTTCGTC      1620

ACCGGCTCCT TCGGGATGTA CGACTACGTG GCGCTCGGCG CGAAGTGA                   1668
```

(2) INFORMATION FOR SEQ ID NO: 21:

(i) SEQUENCE CHARACTERISTICS:
        (A) LENGTH: 1299 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

```
TCAGCCGGAC ATCCGGGCCC CGGCCGCGAC CCCGCGCCGG ATCGGCCAGT GGCCCTGCGC      60

CAGGGGCCGT TCCACGCTGC GGCAGGCGAG AGCGGCCTCG CGGAACTCCG CCTCGTACAG     120

CGCGAGCTGG CGCAGGAACT GCCGGGTCGG GCCGGTCAGG CTGGTCCCCC GCGGGCTGCG     180

CAGCAGCAGC CGGGCGCCGA GGGACTGCTC CAGCCGGTGA ATCCGGCGGG TGAGCGCCGA     240

CTGGCTGATC GACAGCACCG CCGCGGCCCG GTTGATGCTG CCGTGCCGGG CCACGGCCTG     300

GAGCAGATGG AGATCGTCCA CATCCAGTTT GCGGCCCTCG GCCTGGCCGG GCACGGAGCC     360

CTGGTCGGGT CCCGCCCCGA AGCGGCGGGC GTCCGCGCCG GTGCGCTCCG CGTACCACTG     420

CGCCCACCAG GGCTCGTCCA GCAGGTCGCG GTGGTGTTCG GCGAAGCGCC GGAGCTGGAC     480

CTCGGCGATC AGCGCGGCCA GCCGTCCCGC CAGCGCCCGG GGCACGATGG TGGGGTCGAC     540

GAGCAGACTC GTGGTGCGGC GCGGGCGCTC CGCCAGGGAG CGGCGCACCA GCGAGGGGTC     600

CTGCACCGCC GGGTGGGTGG GCGAGCCGAG ACCTATCGCG TCCCCGCGGC GCAGGATGCC     660

CCGGGCAACC GATGCCCCCG TGATGTGGAG CCGGGTGGGC GCGGTGAGCC CGGCCAGCTG     720

GAAGACACGT GTCACCAGGA TCTCCGAGCC GGGTCCCGTC TCGGACACCC AGGTCTCGTC     780

CCGCAGATCG GCGAGCGAGA CCTCCCGCCG GGCGGCCAGC GGATGGTCCC GGGGCAGGAT     840

CACCCACAGC GGGTCGTCCA GCACCTCACA GGTGCGCACG GACCGCTCCA GGCTGTGCCG     900

GGGGACTGG AGGCTCCAGG TGTAGGCCGC GTCCACCTGG TAGCCCGCCA GTTGGGCGGC     960

GACCTGGTGC GGGGCCTCGT GCCGGACCGA CAGCAGCAGG TCCAGCGAGG CCGCCGCGTC    1020

CTCCACCACC TCGTCGAGCA GGGGTTCCGT GGAGACCAGC GACAGCACCT CCGGGGCGTC    1080

CACGGCCTCG GAGCCATGGC CGAAGATATG CGTCCGCGCG GCCAGGTCGA CCTGGTGGAA    1140

GAACCGCCGC CCGGCGACGA GGATGCGGGA GCCCGCGGTG GTCAGCCGGG CCGTGTGGCG    1200

GCTGCGCAGG GTCAGCGGGA GGCCGACGAT CCGGTCCAGC CGGTCGAGTC TGCGCTCCAC    1260

GGTGCCGTGC CGGACACCCG TCCGCCGGGC CACTTCCAT                          1299
```

(2) INFORMATION FOR SEQ ID NO: 22:

(i) SEQUENCE CHARACTERISTICS:
        (A) LENGTH: 744 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

```
TCAGACCTGG TCGGTGGGGC GTATGAAGAT CTCGTGGACG GTCGCGTGGT GCGGCGCGGT      60

CACGGCGTAG CGGACCGCCT CCGCGATGTC CTGGGCCTGG AGCTTGCGGA TCTGGCTGAT     120

CCGCTGCTCG TACATCTCCT TGGTGGCGGT GTGGGTGATG TGGCCGCGCA GCTCCGTGTC     180

GGTGGTGCCC GGCTCGATGA CGACGACCCG CACCCCGCGC TCGGTGACCT CCTGGCGCAG     240

CGTCTCGCTG AACGCGTTCA CACCGAACTT CGTGGCCTGG TAGACGGCCG CGTTGCGGAC     300
```

```
GTTCACCCGG CCCGCGATCG AGGACATCTG CACCACGGTG CCCTTGCTGC GCAGCAGATG    360

GGGAAGGGCC GCCCGGGTCA TGTACATCAG GCCCAGGAGA TTGGTGTCGA TCATCCGGGT    420

CCAGTCGGTG GTGTCGGCGT CCTCCACCGG GCCGAGCAGC ATGATCCCGG CGTTGTTGAC    480

GAGGATGTCG AGGCCGCCCA GCGCCTCGAC GGTGGAGGCG ACGGCGGCGT CCACCCCCTG    540

CCGGTCGGCG ACGTCGAGTT CGAGGACATG GACCTTCGCC CCGGCGGCGG TCAGCTCGTC    600

ACCCAGGGCG CGCAGCTTCT CGACCCGGCG CGCGGCGATG GCCACGGCGG CGCCCTCGGC    660

GGCCAGGGCG CGGGCCGTGG CCTCGCCGAT GCCCGAGCTC GCGCCCGTGA TGAGCGCGAC    720

TTTCCCCTGG AGTGCGGATG GCAT                                          744
```

(2) INFORMATION FOR SEQ ID NO: 23:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

```
ATGATGAACG AGGCAGCGCC TCAGTCCGAC CAGGTGGCAC CGGCGTATCC GATGCACCGG     60

GTCTGCCCGG TCGACCCGCC GCCGCAACTG GCCGGGCTGC GGTCCCAGAA GGCCGCGAGC    120

CGGGTGACGG TGTGGGACGG CAGCCAGGTG TGGCTGGTGA CCTCGCACGC CGGGGCCCGG    180

GCCGTCCTGG GCGACCGCCG CTTCACCGCG GTGACGAGCG CGCCCGGCTT CCCGATGCTG    240

ACCCGCACCT CCCAACTGGT GCGCGCCAAC CCGGAGTCGG CGTCGTTCAT CCGCATGGAC    300

GACCCGCAGC ACTCCCGGCT GCGCTCGATG CTCACCCGGG ACTTCCTGGC CCGCCGCGCC    360

GAGGCGCTGC GCCCCGCGGT GCGGGAGCTG CTGGACGAGA TCCTGGGCGG GCTGGTGAAG    420

GGGGAGCGGC CGGTCGACCT GGTCGCCGGA CTGACGATCC CGGTGCCCTC GCGGGTCATC    480

ACCCTGCTCT TCGGCGCCGG TGACGACCGC CGGGAGTTCA TCGAGGACCG CAGCGCGGTC    540

CTCATCGACC GCGGCTACAC CCCGGAGCAG GTCGCCAAGG CCCGGGACGA ACTCGACGGC    600

TATCTGCGGG AGCTGGTCGA GGAGCGGATC GAGAACCCGG GCACCGACCT GATCAGCCGG    660

CTCGTCATCG ACCAGGTGCG GCCGGGGCAT CTGCGGGTCG AGGAGATGGT CCCGATGTGC    720

CGGCTGCTGC TGGTGGCCGG TCACGGCACC ACCACCAGCC AGGCGAGCCT GAGCCTGCTC    780

AGCCTGCTCA CCGACCCGGA GCTGGCCGGG CGCCTCACCG AGGACCCGGC CCTGCTGCCC    840

AAGGCGGTCG AGGAGCTGCT GCGCTTCCAC TCCATCGTGC AGAACGGGCT GGCCCGTGCC    900

GCGGTGGAGG ACGTCCAGCT CGACGATGTG CTCATCCGGG CGGGCGAGGG CGTGGTGCTG    960

TCGCTGTCGG CGGGCAACCG GGACGAGACG GTCTTCCCCG ACCCGGACCG GGTGGACGTG   1020

GACCGCGACG CCCGCCGCCA TCTCGCCTTC GGCCACGGCA TGCACCAGTG CCTGGGCCAG   1080

TGGCTGGCCC GGGTGGAGCT GGAGGAGATC CTCGCCGCGG TGCTGCGCTG GATGCCCGGT   1140

GCCCGGCTCG CGGTGCCCTT CGAGGAGCTG GACTTCCGTC ATGAGGTGTC CAGTTACGGC   1200

CTCGGCGCCC TCCCGGTGAC CTGGTGA                                      1227
```

(2) INFORMATION FOR SEQ ID NO: 24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear -continued

```
    (ii) MOLECULE TYPE: other nucleic acid
         (A) DESCRIPTION:   /desc = "hypothetical sequence"

(xi) SEQUENCE DESCRIPTION: SEQ ID NO: 24:

TAYGCNCARA THCCNACNTT YATG                                         24

(2) INFORMATION FOR SEQ ID NO: 25:

(i) SEQUENCE CHARACTERISTICS:
         (A) LENGTH: 24 base pairs
         (B) TYPE: nucleic acid
         (C) STRANDEDNESS: single
         (D) TOPOLOGY: linear (ii) MOLECULE TYPE: other nucleic acid
         (A) DESCRIPTION:   /desc = "DNA probe"

(xi) SEQUENCE DESCRIPTION: SEQ ID NO: 25:

TACGCSCAGA TCCCSACSTT CATG                                         24
```